US010093956B2

(12) United States Patent
Hirschel et al.

(10) Patent No.: US 10,093,956 B2
(45) Date of Patent: Oct. 9, 2018

(54) METHOD AND APPARATUS FOR ANTIBODY PRODUCTION AND PURIFICATION

(71) Applicant: BIOVEST INTERNATIONAL, INC., Tampa, FL (US)

(72) Inventors: Mark Hirschel, Blaine, MN (US); Robert J. Wojciechowski, Forest Lake, MN (US); Grant Adams, Coon Rapids, MN (US); Darrell P. Page, East Bethel, MN (US); Kimberly Arneson, Minneapolis, MN (US); Jeff Jorgensen, Brooklyn Park, MN (US); Scott Waniger, Minneapolis, MN (US)

(73) Assignee: BIOVEST INTERNATIONAL, INC., Tampa, FL (US)

( * ) Notice: Subject to any disclaimer, the term of this patent is extended or adjusted under 35 U.S.C. 154(b) by 92 days.

(21) Appl. No.: 14/516,868

(22) Filed: Oct. 17, 2014

(65) Prior Publication Data
US 2015/0111252 A1    Apr. 23, 2015

Related U.S. Application Data

(63) Continuation of application No. 14/122,327, filed as application No. PCT/US2012/041949 on Jun. 11, 2012, now abandoned.

(60) Provisional application No. 61/495,832, filed on Jun. 10, 2011.

(51) Int. Cl.
*C12P 21/00* (2006.01)
*A61K 39/00* (2006.01)
*C07K 16/06* (2006.01)
*C12M 1/36* (2006.01)

(52) U.S. Cl.
CPC ............. *C12P 21/00* (2013.01); *A61K 39/00* (2013.01); *C07K 16/065* (2013.01); *C12M 41/48* (2013.01)

(58) Field of Classification Search
None
See application file for complete search history.

(56) References Cited

U.S. PATENT DOCUMENTS

| | | |
|---|---|---|
| 3,148,624 A | 9/1964 | Baldwin |
| 4,047,844 A | 9/1977 | Robinson |
| 4,282,902 A | 8/1981 | Haynes |
| 4,417,861 A | 11/1983 | Tolbert |
| 4,604,038 A | 8/1986 | Belew |
| 4,804,628 A | 2/1989 | Cracauer et al. |
| 4,973,558 A | 11/1990 | Wilson et al. |
| 5,113,906 A | 5/1992 | Högner |
| 5,318,413 A | 6/1994 | Bertoncini |
| 5,330,915 A | 7/1994 | Wilson et al. |
| 5,416,022 A | 5/1995 | Amiot |
| 5,541,105 A | 7/1996 | Melink et al. |
| 5,554,123 A | 9/1996 | Herskowitz |
| 5,571,720 A | 11/1996 | Grandics et al. |
| 5,622,857 A | 4/1997 | Goffe |
| 5,631,006 A | 5/1997 | Melink et al. |
| 5,656,421 A | 8/1997 | Gebhard et al. |
| 5,958,763 A | 9/1999 | Goffe |
| 5,998,184 A | 12/1999 | Shi |
| 6,001,585 A | 12/1999 | Gramer |
| 6,733,252 B2 | 5/2004 | Feygin et al. |
| 7,377,686 B2 | 5/2008 | Hubbard |
| 7,654,982 B2 | 2/2010 | Carlisle et al. |
| 7,935,504 B2 | 5/2011 | Chen |
| 8,133,042 B2 | 3/2012 | Yajima |
| 8,383,397 B2 | 2/2013 | Wojciechowski et al. |
| 8,540,499 B2 | 9/2013 | Page et al. |
| 9,441,195 B2 | 9/2016 | Wojciechowski et al. |
| 9,534,198 B2 | 1/2017 | Page et al. |
| 2003/0040104 A1 | 2/2003 | Barbera-Guillem |
| 2003/0217957 A1 | 11/2003 | Bowman, Jr. et al. |
| 2004/0057856 A1 | 3/2004 | Saxer et al. |
| 2006/0016487 A1 | 1/2006 | Lin |
| 2006/0141623 A1 | 6/2006 | Smith et al. |
| 2006/0257998 A1 | 11/2006 | Klaus et al. |

(Continued)

FOREIGN PATENT DOCUMENTS

| | | |
|---|---|---|
| EP | 0 164 020 | 8/1989 |
| EP | 1 400 691 | 3/2004 |

(Continued)

OTHER PUBLICATIONS

Schubert et al., Comparison of ceramic hydroxy- and fluoroapatite versus Protein A/G-based resins in the isolation of a recombinant human antibody from cell culture supernatant, Journal of Chromatography A, 1142 (2007) 106-113.*
Gharderi et al., Preparation of Anion-Exchange Resin from Styrene-Divinylbenzene Copolymer Obtained by Concentrated Emulsion Polymerizatin Method, Iranian Polymer Journal, 15 (6), 2006, pp. 497-504.*
International Search Report dated Nov. 7, 2007 for International Patent Application No. PCT/US2007/012053, filed May 21, 2007 (2 pp.).
International Search Report dated Oct. 4, 2007 for International Patent Application No. PCT/US2007/012042, filed May 21, 2007 (2 pp.).
International Search Report dated Oct. 4, 2007 for International Patent Application No. PCT/US2007/012052, filed May 21, 2007 (2 pp.).

(Continued)

*Primary Examiner* — Karen Cochrane Carlson
*Assistant Examiner* — Jennifer M. H. Tichy
(74) *Attorney, Agent, or Firm* — Saliwanchik, Lloyd & Eisenschenk

(57) ABSTRACT

The subject invention pertains to methods and apparatus for the production and purification of cell products, such as immunoglobulins. One aspect of the invention is an integrated cell culture and purification apparatus for the growth and maintenance of cells and the harvest and purification of cell products, such as immunoglobulins. Thus, the apparatus integrates a cell culture function with a purification function. Other aspects of the invention pertain to an automated method for producing immunogenic compositions such as vaccines.

16 Claims, 37 Drawing Sheets

(56) References Cited

U.S. PATENT DOCUMENTS

| | | |
|---|---|---|
| 2007/0062872 A1 | 3/2007 | Parker et al. |
| 2007/0148010 A1 | 6/2007 | Michels et al. |
| 2007/0292410 A1 | 12/2007 | Cashman et al. |
| 2008/0017194 A1 | 1/2008 | Hassanein et al. |
| 2009/0215022 A1 | 8/2009 | Page et al. |
| 2009/0269841 A1 | 10/2009 | Wojciechowski et al. |
| 2010/0015696 A1 | 1/2010 | Claes et al. |
| 2010/0105138 A1 | 4/2010 | Dodd et al. |
| 2011/0212493 A1 | 9/2011 | Hirschel et al. |
| 2012/0086657 A1 | 4/2012 | Stanton, IV et al. |
| 2012/0114634 A1 | 5/2012 | Stergiou et al. |
| 2013/0058907 A1 | 3/2013 | Wojciechowski et al. |
| 2014/0024012 A1 | 1/2014 | Page et al. |
| 2015/0225685 A1 | 8/2015 | Hirschel et al. |
| 2016/0362650 A1 | 12/2016 | Wojciechowski et al. |
| 2016/0362652 A1 | 12/2016 | Page et al. |

FOREIGN PATENT DOCUMENTS

| | | |
|---|---|---|
| EP | 1 286 696 | 11/2006 |
| WO | WO-2002/087662 | 11/2002 |
| WO | WO-2003/087292 | 10/2003 |
| WO | WO-2005/031167 | 4/2005 |
| WO | WO 2005/087915 | 9/2005 |
| WO | WO 2005/090403 | 9/2005 |
| WO | WO-2005/116186 | 12/2005 |
| WO | WO 2007/136821 | 11/2007 |
| WO | WO 2007/139742 | 12/2007 |
| WO | WO 2007/139746 | 12/2007 |
| WO | WO 2007/139747 | 12/2007 |
| WO | WO 2007/139748 | 12/2007 |
| WO | WO 2010/042644 | 4/2010 |
| WO | WO 2010/048417 | 4/2010 |
| WO | WO 2012/021840 | 2/2012 |
| WO | WO 2012/064760 | 5/2012 |
| WO | WO 2012/171026 | 12/2012 |
| WO | WO 2012/171030 | 12/2012 |
| WO | WO 2013/086418 | 6/2013 |
| WO | WO-2014/036187 | 3/2014 |

OTHER PUBLICATIONS

International Search Report dated Oct. 5, 2007 for International Patent Application No. PCT/US2007/012051, filed May 21, 2007 (2 pp.).

International Search Report dated Sep. 25, 2007 for International Patent Application No. PCT/US2007/012054, filed May 21, 2007 (3 pp.).

Knazek, R. et al., "Cell Culture on Artificial Capillaries: An Approach to Tissue Growth in vitro," *Science*, 1972, vol. 178, No. 4056, pp. 65-67.

Natsume A et al., "Engineered Antibodies of IgG1/IgG3 Mixed Isotype with Enhanced Cytotoxic Activities" *Cancer Research*, 2008, 68(10):3863-3872.

* cited by examiner

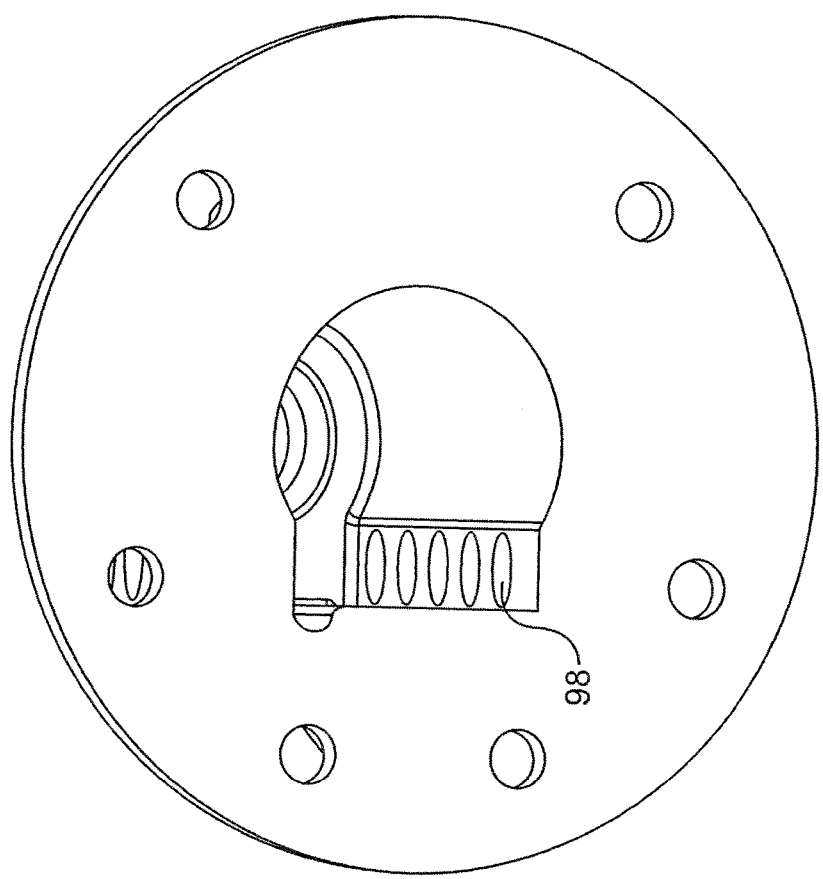

| | | PH | GAS | ICP | ECP | ECS | REF.T | MED.T | INC.T | OUT | MED | FACT | HARV | CIRC |
|---|---|---|---|---|---|---|---|---|---|---|---|---|---|---|
| OCT. 01, 2004 9:47.43 | AIR INLET PRESSURE LOW | | | | | | | | | | | | | |
| OCT. 01, 2004 9:47.43 | | 6.65 | 0.0 | 0 | 0 | FALL | 1.6 | 25.0 | 26.1 | 0 | 100 | 0 | 0 | 200 |
| OCT. 01, 2004 9:47.49 | FALL CYCLE COMPLETE IN 0:03 | | | | | | | | | | | | | |
| OCT. 01, 2004 9:48.26 | STARTUP, DOWN TIME: 0-00:00 | | | | | | | | | | | | | |
| OCT. 01, 2004 9:49.48 | RISE CYCLE COMPLETE IN 0:02 | | | | | | | | | | | | | |
| OCT. 01, 2004 9:52.44 | | 7.10 | 50.8 | 0 | 51 | FALL | 5.2 | 38.1 | 48.7 | 125 | 100 | 0 | 0 | 200 |
| OCT. 01, 2004 9:54.53 | FALL CYCLE COMPLETE IN 5:05 | | | | | | | | | | | | | |
| OCT. 01, 2004 9:55.29 | RISE CYCLE COMPLETE IN 0:36 | | | | | | | | | | | | | |
| OCT. 01, 2004 9:57.45 | | 7.10 | 49.8 | 0 | 51 | FALL | 5.0 | 37.4 | 48.7 | 125 | 100 | 0 | 0 | 200 |
| OCT. 01, 2004 9:58.59 | INSTRUMENT HOLD, PUMPS STOPPED | | | | | | | | | | | | | |
| OCT. 01, 2004 9:59.00 | INSTRUMENT RESUMED FROM HOLD | | | | | | | | | | | | | |

TOTAL: 278    RECORDS 158 THRU 168    FREE: 0.0 MB

TOP    PG UP    ◁    ▷    PG DN    END

HOLD    EXIT    HELP

FIG. 28

METHOD AND APPARATUS FOR ANTIBODY PRODUCTION AND PURIFICATION

CROSS-REFERENCE TO RELATED APPLICATIONS

The present application is a continuation of U.S. application Ser. No. 14/122,327, filed Nov. 26, 2013, which is the National Stage of International Application No. PCT/US2012/041949, filed Jun. 11, 2012, which claims the benefit of U.S. Provisional Application Ser. No. 61/495,832, filed Jun. 10, 2011, each of which is hereby incorporated by reference herein in its entirety, including any figures, tables, or drawings.

BACKGROUND OF THE INVENTION

The anticipated growth of personalized medicine will require new paradigms for the manufacture of therapies tailored to the needs of individual patients. The greatest challenge is expected to come in the area of cell based therapies, especially when such therapies are autologous in nature. In such cases, each cell or cell based product will need to be manufactured from scratch for each patient. Manual methods for mammalian cell culture, by their nature, are prone to technician error or inconsistency leading to differences between supposed identical cultures. This becomes especially evident as more and more autologous cells are expanded for personalized therapies. Patient-specific cells, or cell products such as proteins, are subject to variation, especially when scaled beyond levels that can be managed efficiently with manual methods.

With the increased use of proteins, such as antibodies, in clinical diagnostics and therapy, the need has arisen for more efficient, rapid and sterile purification methods. Conventional purification techniques typically involve manually passing mixtures containing proteins through a suitable column to selectively adsorb the proteins from the mixture. The adsorbed proteins are then eluted from the column in purified form.

Manual methods for purifying proteins have their drawbacks. For example, these methods can be labor intensive, time consuming and typically use multiple columns which are manually packed with resin and sterilized prior to each purification run. The manual steps involved in these methods also include a high risk of contamination.

In addition to being labor intensive, the stringent requirements for segregation of each patient's materials from that of every other patient will mean that manufacturing facilities will be large and complex, containing a multitude of isolation suites each with its own equipment (incubators, tissue culture hoods, centrifuges) that can be used for only one patient at a time. Because each patient's therapy is a new and unique product, patient specific manufacturing will also be labor intensive, requiring not just direct manufacturing personnel but also disproportionately increased manpower for quality assurance and quality control functions.

Moreover, conventional approaches and tools for manufacturing cells or cell based products typically involve numerous manual manipulations that are subject to variations even when conducted by skilled technicians. When used at the scale needed to manufacture hundreds or thousands of different cells, cell lines and patient-specific cell based therapies, the variability, error or contamination rate may become unacceptable for commercial processes.

Small quantities of cell-secreted product are produced in a number of different ways. T-flasks, roller bottles, stirred bottles or cell bags are manual methods using incubators or warm-rooms to provide environments for cell growth and production. These methods are very labor intensive, subject to mistakes and difficult for large-scale production.

Another method for producing cell secreted products is by ascites production, which requires injecting the peritoneum of a host animal (usually a mouse) with the cells that express the product, which are thereby parasitically grown and maintained. The animals are sacrificed and the peritoneal fluid with the product is collected. This method is also very labor intensive, difficult for large scale production, and objectionable because of the use of animals.

Another method for producing cell secreted products involves inoculating and growing the cells in a small stirred tank or bioreactor or bag-type chamber. The tank provides the environmental and metabolic needs and the cell secretions are allowed to accumulate. This method is costly in terms of facility support in order to accommodate a large number of unique cells and produces product at low concentration.

Another method for the production of cell secreted products is to use a bioreactor (hollow fiber, ceramic matrix, fluidizer bed, etc.) in lieu of the stirred tank. This can bring facilities costs down and increases product concentration. The systems currently available are general purpose in nature and require considerable time from trained operators to setup, load, flush, inoculate, run, harvest, and unload. Each step typically requires manual documentation, which is labor intensive and subject to errors.

Cell culturing devices or cultureware for culturing cells in vitro are known. As disclosed in U.S. Pat. No. 4,804,628, the entirety of which is hereby incorporated by reference, a hollow fiber culture device includes a plurality of hollow fiber membranes. Medium containing oxygen, nutrients, and other chemical stimuli is transported through the lumen of the hollow fiber membranes or capillaries and diffuses through the walls thereof into an extracapillary (EC) space between the membranes and the shell of the cartridge containing the hollow fibers. The cells that are to be maintained collect in the extracapillary space. Metabolic wastes are removed from the bioreactor. The cells or cell products can be harvested from the device.

Known EC reservoirs have typically been rigid. They are a pressure vessel and therefore require a sealed compartment with tubing ports adding to costs. A gas, typically air, is introduced through a sterile barrier, generally a membrane filter, to control pressure in the vessel. Fluid level control has been limited to ultrasonic, conductive or optical trip points, or by a load cell measuring the weight of the fluid. Reservoirs are expensive and difficult to manufacture. There is limited EC fluid level measurement accuracy-ultrasonic, conductive or optical monitoring of fluid levels are commonly fouled by cell debris in the reservoir. Alternatively, load cells are not a rugged design for reliable fluid level sensing.

Another problem with the prior systems is the inability to control lactate and sense pH in the system. One method takes samples of the culture medium and analyzes it using an off-line analyzer. The operator adjusts the perfusion medium rate based on values obtained to maintain the lactate concentration at the level desired. The operator must attempt to predict future lactate levels when adjusting media feed rates. This is labor intensive, presents potential breech of sterility, and the level of lactate control accuracy is dependent on operator skill.

Another method is to connect an automated sampler/analyzer to periodically withdraw sample of the culture media, analyze it and provide feedback for a media feed controller. This method requires additional equipment and increases the risk of sterility breech.

Yet another method is to use an invasive lactate sensor to directly read the lactate level and provide feedback for a media feed controller. In line lactate sensors need to be sterilizable, biocompatible, typically have low reliability and need periodic maintenance.

These methodologies rely on costly, labor intensive off-line sampling and analysis or additional equipment to interface with the instrument or require the addition of a lactate probe and electronics to the culture.

Disposable cultureware generally cannot be autoclaved, so a pH sensor is historically sterilized separately and then added to the cultureware. However, adding the probe risks compromising the sterility of the cultureware. Probe addition is performed in a sterile environment (laminar flow hood) and increases the manpower needed.

The previous methodologies that utilize off-line sampling are subject to contamination problems and depend on the skill of the operator in predicting future lactate levels and influence of media dilution rate. Sampling equipment need interfacing to the culture fluidic circuit, an interface for the feedback signal and periodic calibration of the probes used for sampling. The lactate probe requires interface with the fluid circuit, a method for sterilization or a sterile barrier, interface electronics to convert the probe signal to a useful feedback and a method to calibrate in the fluid circuit.

Preparing conventional systems to start the cell culture is also very labor intensive. The cultureware must be assembled and sterilized or probes must be prepared, sterilized and aseptically inserted into the pre-sterilized portion of the cultureware. The cultureware assembly is then loaded onto the instrument. A series of manual operations are needed to check the integrity of the assembly, introduce fluid into the cultureware flow path, flush the toxic residuals (e.g., surfactants) from the cultureware, start the cultureware in a pre-inoculation mode, introduce factors into the flow path getting it ready for the cells, inoculating the cells into the bioreactor and starting the run (growth of the cell mass and eventual harvest of product).

Two methods are generally used for sterilization. One method places an electrode in a holder, steam sterilizes the assembly (probe) and then aseptically inserts the probe into the pre-sterilized cultureware. The second method involves placing a non-sterile probe into a holder and then using steam to sterilize the electrode in place, referred to as steam in place. Both methods are labor intensive, prone to failure and the procedures need to be validated.

Other methods exist which are less common. Cold sterilants can be used to sterilize the holder and electrode before aseptic insertion. A permeable membrane can be used to isolate the non-sterile probe from the sterile fluid being sensed. A holder with the membrane is placed in the fluid path, either before sterilization or after if the holder and membrane is sterilized separately, and then the sensor is placed against or close to the membrane and the fluid on both sides of the membrane is assumed to be equilibrated.

Glass electrodes have not been included with the cultureware in the past because it was unknown if the probes could survive EtO sterilization and being stored dry. Filled glass electrodes are normally stored hydrated in a liquid buffer.

Each unique cell or cell line must be cultured, with cell products harvested and purified separately. In order to accommodate a large number of unique cells or cell lines, a considerable number of instruments would be needed. If application of the cells or products for therapeutic purposes is contemplated, strict segregation of each cell production process would be required. Consequently, compactness of the design and the amount of ancillary support resources required will become an important facilities issue. Moreover, the systems currently available are general purpose in nature and require considerable time from trained operators to setup, load, flush, inoculate, run, harvest and unload. Each step usually requires manual documentation.

Moreover, production tracking mandates generation of a batch record for each cell culture run. Historically, this is done with a paper-based system and relies on the operator inputting the information. This is labor intensive and subject to errors.

Current purification techniques also involve cleaning and reuse of components. This requires Standard Operational Procedures (SOPs) to be written and the cleaning and reuse process to be validated. This is a time intensive activity.

Accordingly, there is a need for an apparatus and method whereby cells and/or cell products can be cultured and purified in a fully automated, rapid and sterile manner.

BRIEF SUMMARY OF THE INVENTION

One aspect of the invention is an integrated cell culture and purification apparatus for the growth and maintenance of cells and the harvest and purification of cell products such as cell secreted products (if required). Thus, the apparatus integrates a cell culture function with a purification function. The apparatus can be used for short production runs (e.g., less than 45 days) of a large number of unique cell lines, or longer production runs. The apparatus is designed such that it can be incorporated into a production facility, and to support centralized batch information gathering. Advantageously, the apparatus's design minimizes operator time needed to setup and run the apparatus. Purification of cell-secreted product is exemplified herein; however, if cell production is the product, a cell harvest unit can be used in place of the purification unit.

The integrated apparatus of the invention has the capacity for a high degree of automation. This reduces the amount of operator's time needed and reduces operator-induced errors. Cultureware modules (disposable portions of the cell culture unit and purification unit) are highly integrated and easy to load/unload. The control process is designed to complete sequences without the need for operator's intervention. The apparatus is modularized into a cell culture unit and purification unit. The purification unit uses the resources of the cell culture module for coordination and control. A single purification unit can support multiple cell culture units. The apparatus is designed to facilitate a central electronic records system operated in a current good manufacturing practice (CGMP) facility. Instrument support is provided for operator and consumables code identification (e.g., bar code identification, radio frequency identification (RFID) tag identification, bokode, identification or quick response (QR) code identification).

The integrated apparatus of the invention includes two units: a cell culture unit and a purification unit. The two units are physically separate but designed to be placed together (e.g., adjacent to one another). The cell culture unit and purification unit can transfer data and coordinate activity with each other using methods known in the art, such as through an infrared communication port. The purification unit can be placed next to the cell culture unit towards the end of the production period. A tubing line from each unit's cultureware connects together to provide a fluid path for the collected harvest fluid in the cell culture unit to be transferred to the purification unit. The operator initiates the purification sequence through a user interface such as a touch screen interface on the cell culture unit. The end product of the system can be a purified and neutralized product in a buffered solution suitable for further processing.

The cell culture unit of the integrated apparatus includes two individual parts: a reusable instrumentation base device (also referred to herein as a "first" reusable instrumentation base device, to distinguish it from the reusable instrumentation base device of the purification unit), and at least one disposable cell cultureware module that is used for a single production run and is disposable (also referred to herein as a "first" disposable cell cultureware module, to distinguish it from the at least one disposable cultureware of the purification unit). The instrumentation base device provides the hardware to support cell culture growth and production in a compact package, which is advantageous in a facility handling a large number of unique cell lines, for example. A pump, such as an easy-load 4 channel peristaltic pump, moves fresh basal media into the cultureware, removes spent media, adds high molecular weight factor and removes product harvest. An integrated cool storage area maintains the factor and harvest at a low temperature (preferably, approximately 4° C.). A heating mechanism maintains the cell environment to promote growth and production. The gas blending mechanism, in conjunction with the cultureware pH sensor controls the pH of the cell culture medium. A plurality of automated tube valving drives (e.g., three automated tube valving drives) are used to control the cultureware flowpath configuration to accomplish the fluidic functions necessary to initiate and carryout a successful run. Valves and sensors in the instrumentation base device control the fluid cycling in the cultureware. Drive for fluid circulation is provided. An identification code reader, such as a barcode reader, is preferably included to facilitate operator and lot tracing. A communication port preferably ties the instrumentation device to a facilities data management system (LIMS). Preferably, the instrumentation device of the cell culture unit includes a user interface, such as a flat panel display with touch screen, for user interaction.

The one-time use cultureware is provided pre-sterilized, designed for rapid loading onto the instrumentation base device ("quick-load"). The loading of the cultureware body makes connections to the instrumentation base device. The pump cassette, which is physically attached to the tubing, allows the user to quickly load the pump segments. The design and layout minimizes loading errors. The cultureware enclosure provides an area that is heated to maintain cell fluid temperature. Reservoirs to maintain fluid volumes and cycling are included in the cultureware. Sensors for fluid circulation rate and pH and thermal well for the instrument's temperature sensor are included. The blended gas from the instrumentation device is routed to the gas exchange cartridge that provides oxygen and adds or removes carbon dioxide to the circulated fluid to support cell metabolism. The cultureware module also includes a bioreactor (e.g., hollow fiber bioreactor or other bioreactor type), which provides the cell space and media component exchange. Disposable containers for harvest collection and flushing are provided. The operator attaches a media source, factor bag and spent media container to the cultureware before running. The media and spent media container is disconnected, pump cassette is unloaded, cultureware body is unloaded and the used cultureware is placed in a biohazard container for disposal.

The purification unit of the integrated apparatus includes two individual parts: a reusable instrumentation base device (also referred to herein as a "second" reusable instrumentation base device, to distinguish it from the reusable instrumentation base device of the cell culture unit), and at least one disposable cell cultureware module that is used for a single production run and is disposable (also referred to herein as a "second" disposable cell cultureware module, to distinguish it from the at least one disposable cultureware of the cell culture unit).

The instrumentation base device of the purification unit provides the hardware to extract the fluid with the cell product from the cell culture unit and process it. An air detector checks the cultureware line which carries the fluid from the cell culture module to determine when fluid is available to run through the column and when no more fluid is available. Drives for a plurality of switching valves (e.g., nine switching valves) control the disposable valve portions to route fluids to complete the processes. A peristaltic pump is used to move the fluids to accomplish the process. A cooler lowers the disposable column temperature to minimize product degradation. An optical density detector is used in the process to determine when final product should be collected. The purification unit relies on the cell culture unit for user interface and communications with the facilities data management system. One or more pressure sensors may be included for monitoring fluid pressure for excessive pressures, or for control of peristaltic pump speed, e.g., to maintain the pump speed at a desired pressure (a feedback mechanism). In some embodiments, the pressure sensor is placed in the purification flow path, on the output of the pumps.

In some embodiments, one or more correction sensors are employed for monitoring back-pressure. In some embodiments, one or more conductivity sensors may be used to monitor fluid exchange, and/or product harvest. In some embodiments, one or more optical density sensors are used to monitor proteins in the fluid.

As is the case with the cultureware of the cell culture unit, the cultureware of the purification unit is for one-time use. The selection device (e.g., purification column(s)) is loaded into the cultureware just before use. The reservoirs are filled at that time with the correct buffers for the cell product type. That information is tied to the cultureware's identifying code (e.g., bar code, radio frequency identification (RFID) tag, bokode, or quick response (QR) code) in the facilities data management system when the operation is done and is used to verify the proper purification cultureware is loaded for the cell product that is to be purified. A plurality of disposable switch valves (e.g., three disposable switch valves) are used to prepare the cultureware and route the fluids. An easy-load peristaltic pump cassette is provided. A flow cell for measuring optical density is provided on the outlet of the selection device. A removable container holds the finished product (e.g., cell-derived product, such as antibody). The pump cassette and cultureware body is unloaded from the instrumentation base device of the purification unit and placed in a biohazard container for disposal.

As an enclosed apparatus, the safety provided by complete segregation facilitates direct applicability to therapies or diagnoses that require autologous cell culture. This self-contained, automated cell culture and purification apparatus allows for simultaneous culture of numerous cell cultures within a compact facility, without the need for individual, segregated cell culture suites. The integrated apparatus of the present invention provides a compact, sealed containment apparatus that will enable the cost effective manufacture of cells, cell lines, cell products, including patient-specific cells and patient-specific cell products, and purification of the foregoing, on an industrial scale.

Another aspect of the present invention is to provide a method and apparatus that incorporates disposable cultureware, which eliminates the need for cleaning and reuse.

Yet another aspect of the present invention is an apparatus that has the stand-alone integration of a large apparatus in a bench top device (pumps, controls, incubator, refrigerator, cultureware, etc.).

Still another aspect of the present invention is an apparatus that incorporates an identification code reader, such as a barcode reader, and data gathering software that, when used with an information management system (such as a manufacturing execution system or MIMS), allows for automating generation of the batch record.

Another aspect of the present invention is to provide an EC cycling unit that costs less than rigid reservoirs. Moreover, due to the sealed EC circuit design, without vented reservoir, the chance of cell contamination is minimized.

Still another aspect of the present invention is to provide an apparatus that controls lactate concentration in a perfusion cell culture system using measurement of $CO_2$ and pH.

Yet another aspect of the present invention is to eliminate preparation, autoclaving, and insertion of pH electrodes aseptically in the cultureware which requires a significant amount of time and may breach the sterile barrier of the cultureware set.

The apparatus of the present invention incorporates features that greatly reduce the operator's time needed to support the operations (e.g., integrated pump cassette, pre-sterilized cultureware with pH sensors, quick-load cultureware) and designed automated procedures and apparatuses which allow the apparatus to sequence through the operations (e.g., automated fluid clamps, control software).

The apparatus integrates the cell culture product production and purification process. The design of the cultureware and instrument simplifies and reduces labor needed to produce product. This reduces sources of error in the process.

The present invention provides an integrated, automated cell culture and purification apparatus which creates a self-contained culture environment. The apparatus incorporates perfusion culture with sealed, pre-sterilized disposable cultureware, such as hollow fiber or other bioreactors, programmable process control, automated fluid valving, pH feedback control, lactic acid feedback control, temperature control, nutrient delivery control, waste removal, gas exchange mechanism, reservoirs, tubing, pumps and harvest vessels. Accordingly, the cell culture unit (referred to as AutovaxID Cell Culture Module™) is capable of expanding cells in a highly controlled, contaminant-free manner. Cells to which this approach are applicable include transformed or non-transformed cell lines, primary cells including somatic cells such as lymphocytes or other immune cells, chondrocytes, myocytes or myoblasts, epithelial cells and patient specific cells, primary or otherwise. Included also are cells or cell lines that have been genetically modified, such as both adult and embryonic stem cells. Specifically, the automated cell culture apparatus allows for production and harvest of cells or cell-secreted protein in a manner that minimizes the need for operator intervention and minimizes the need for segregated clean rooms for the growth and manipulation of the cells. Further, the apparatus provides a culture environment that is completely self-contained and disposable. This eliminates the need for individual clean rooms typically required in a regulated, multi-use facility. Control of fluid dynamics within the bioreactor allows for growth conditions to be adjusted, e.g. changing growth factor concentrations, to facilitate application of unique culture protocols or expansion of unique cells or cell lines. As a result, there is less variation and less labor required for consistent, reproducible production of cells for applications to expansion of autologous cells and their use in personalized medicine applications.

According to these and other aspects of the present invention, there is provided a cell culture unit for the production of cells and cell derived products including a reusable instrumentation base device incorporating hardware to support cell culture growth. A disposable cultureware module including a cell growth chamber is removably attachable to the instrumentation base device.

According to these and other aspects of the present invention, there is also provided a method for the production of cells and cell products in a highly controlled, contaminant-free environment comprising the steps of providing a disposable cultureware module including a cell growth chamber, and a reusable instrumentation base device incorporating hardware to support cell culture growth. The base device includes microprocessor control and a pump for circulating media through the cell growth chamber. The cultureware module is removably attached to the instrumentation base device. Cells are introduced into the cell growth chamber. A source of media is fluidly attached to the cultureware module. Operating parameters are programmed into the microprocessor control. The pump is operated to circulate the media through the cell growth chamber to grow cells or cell products therein. The grown cells or cell products are harvested from the cell growth chamber. The cultureware module is then disposed of.

In some embodiments, the cell products comprise immunoglobulin, such as IgM, IgG, IgD, IgE, IgA, or an immunoglobulin of mixed (chimeric) isotypes (e.g., IgM/IgD, IgM/IgA, IgM/IgG, or IgG/IgA; see, for example, Natsume A. et al., *Cancer Res.*, 2008, 68(10):3863-3872).

In a particular embodiment, the present invention provides an automated method of producing a vaccine by purifying a protein, such as an antibody (immunoglobulin), and conjugating the protein to an adjuvant, such as keyhole limpet hemocyanin (KLH). In some embodiments, the protein is an antibody that targets a B-cell antigen expressed on B cell tumors. In some embodiments, the antibody is an IgM, IgG, or mixed isotype.

BRIEF DESCRIPTION OF THE DRAWINGS

FIG. 14C is a rear view of the valve body.

FIGS. 26-31 are views of the touch screen associated with the automatic control of the cell culture unit of the present invention.

DETAILED DESCRIPTION OF THE INVENTION

Figure 33A:
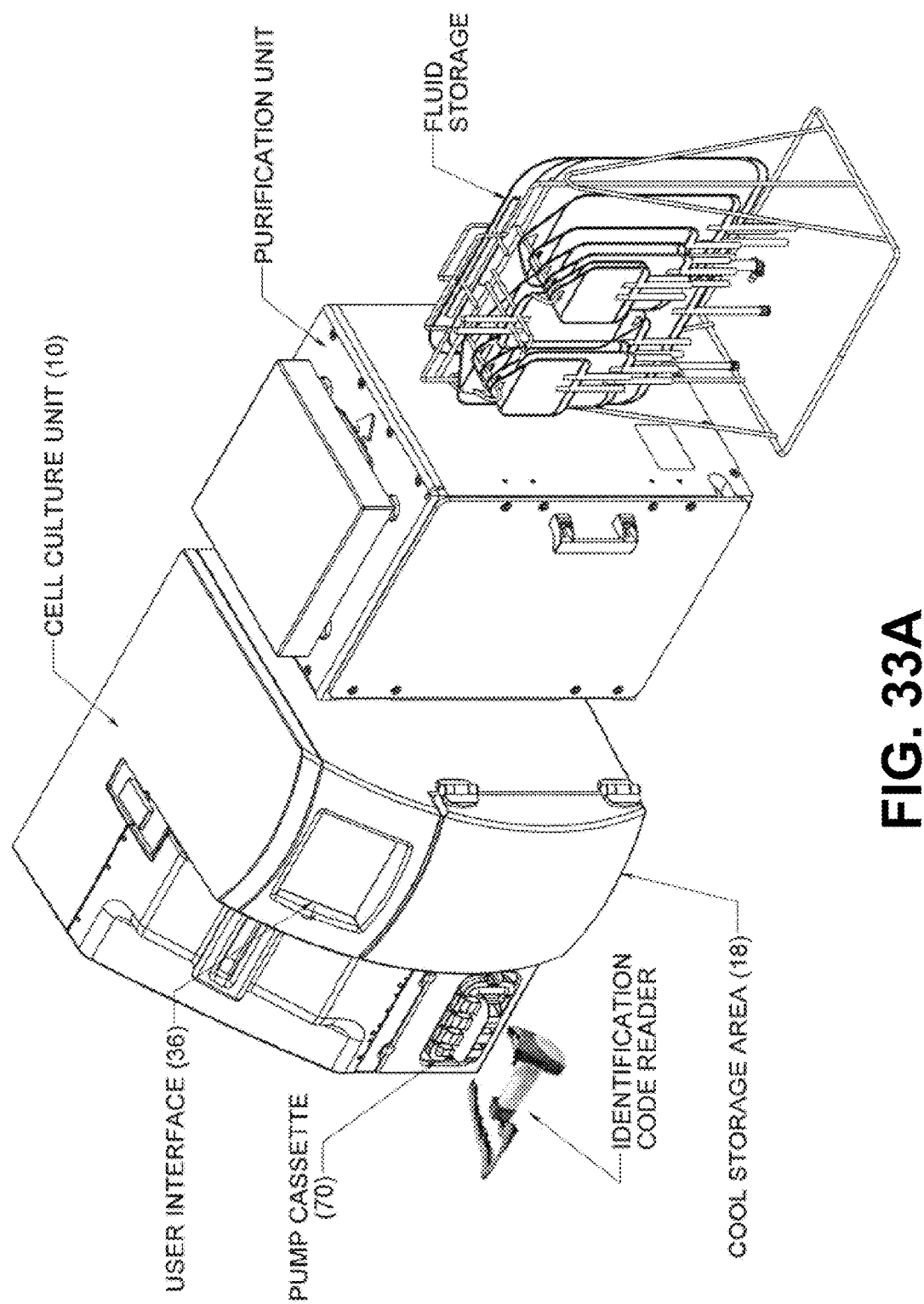
FIGS. 33A and 33B are isometric and front views of an embodiment of the integrated cell culture and purification apparatus of the invention, including the cell culture unit and purification unit adjacent thereto.
Figure 33B:
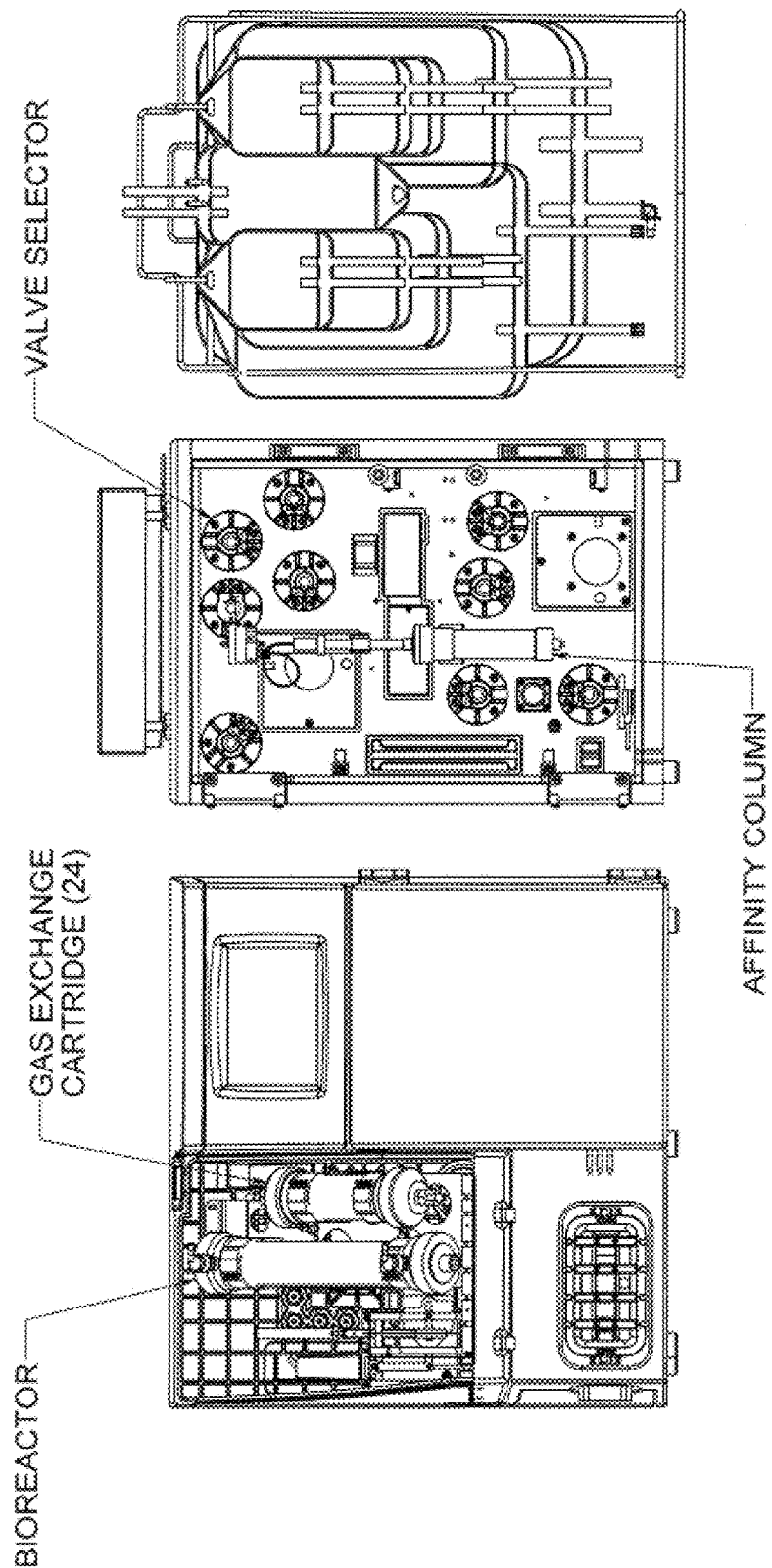
Figure 34:
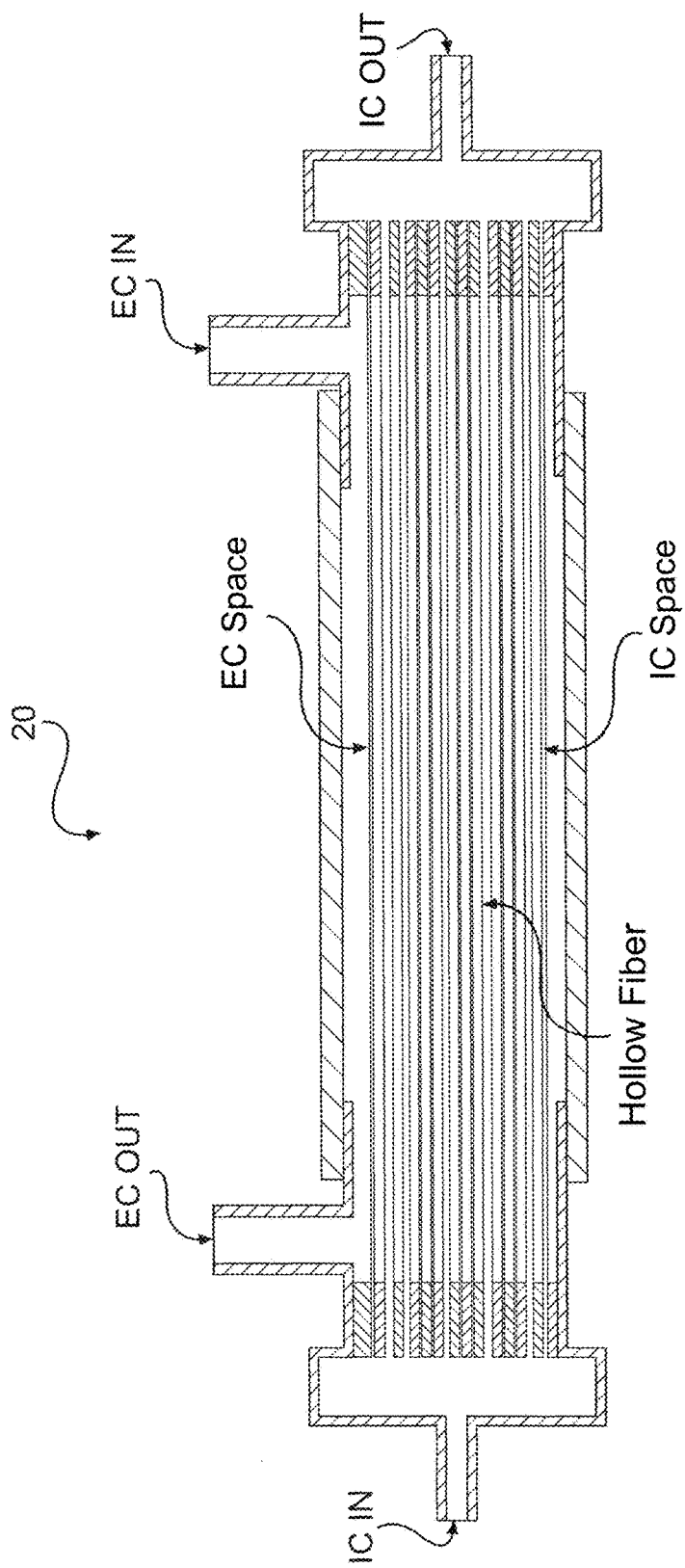
FIG. 34 shows an embodiment of a hollow fiber perfusion bioreactor of the Autovaxid instrument, with hollow fibers and in and out ports for the intracapillary space and extra-capillary space indicated. As will be appreciated by those skilled in the art, the sidedness and orientation of the ports on the bioreactor are not critical.

The integrated apparatus of the invention includes two units: a cell culture unit and a purification unit (FIG. 33). The two units are physically separate but designed to be placed together (e.g., adjacent to one another). The cell culture unit and purification unit can transfer data and coordinate activity with each other using methods known in the art such as a communication port (e.g., an infrared communication port, desktop or laptop computer, etc.). The purification unit can be placed next to the cell culture unit toward the end of the production period, or before. A tubing line from each unit's cultureware connects together to provide a fluid path for the collected harvest fluid in the cell culture unit to be transferred to the purification unit. The operator initiates the purification sequence through a user interface such as a touch screen interface on the cell culture unit. Advantageously, the end product of the apparatus can be a purified and neutralized product in a buffered solution suitable for further processing.

Integrating components, functions, and operations greatly reduces manpower and cost needed to produce a cell-derived product. Integrated cultureware reduces preparation and loading time. Cultureware simplification reduces the number of operator induced errors which can cause failure. Process sequencing reduces operator time needed and allows sequential operations to be automatically. Modularizing the functions into a cell culture unit and a purification unit allows higher utilization of hardware and lower costs. One purification unit can service multiple cell culture units. Utilizing the resources of the cell culture unit allows for reduced costs of the purification unit and logistically ties the two processes together. A CGMP facility is required to generate a batch record documenting the individual cell product production. The apparatus can facilitate record generation by utilizing a central electronic records system operated in a CGMP facility.

Some examples for which the apparatus of the present invention can be used are:

The production of monoclonal antibodies from hybridoma cell lines.

The expansion of autologous patient-derived blood cells including immune cells for therapeutic application.

The expansion of patient derived somatic cells for subsequent re-infusion back into patients for therapeutic purposes. A specific example already available for therapeutic application in patients is the harvesting and expansion of patient specific cartilage cells (chondrocytes) followed by re-infusion of those cells back into a region containing damaged articular cartilage.

The expansion of patient derived or non-patient-derived multipotent cells, including embryonic stem cells, adult stem cells, hematopoeitic stem or progenitor cells, multi or pluripotent cells derived from cord blood for therapeutic purposes.

The expansion of somatic or germline cells in which the cells have been genetically modified to express novel cellular components or to confer on them other beneficial properties such as novel receptors, altered growth characteristics or genetic features, followed by introduction of the cells into a patient for therapeutic benefit. An example is the expansion of patient specific fibroblasts genetically modified to express growth factors, clotting factors, or other biologically active agents to correct inherited or acquired deficiencies of such factors.

In the methods and apparatus of the invention, harvesting can be carried out by various methods, such as batch harvest, timed batch harvest, or continuous harvest. In batch harvesting, a single harvest of the bioreactor may be initiated by the operator based on product (e.g., antibody) concentration. All product is collected at this time. In timed batch harvesting, the harvest is initiated by the operator based on product concentration. A predetermined volume is harvested from the bioreactor. After a defined interval, another volume is harvested. This is repeated for a predetermined number of cycles or until the operator terminates the harvesting. In continuous harvesting, the instrument harvests a given volume per unit of time (e.g., hour) continuously. The harvest can be initiated by the operator based on product concentration. Harvest continues until a time interval has passed or until the operator terminates the harvesting.

Definitions

In order to more clearly and concisely describe the subject matter of the claims, the following definitions are intended to provide guidance as to the meaning of specific terms used herein.

It is to be noted that the singular forms "a," "an," and "the" as used herein include "at least one" and "one or more" unless stated otherwise. Thus, for example, reference to "a cultureware module" includes more than one cultureware module, reference to "an affinity column" or "a purification column" includes more than one column, and the like.

As used herein, the term "adjuvant" refers to any substance which enhances the immune-stimulating properties of an antigen.

The term "antibody," as referred to herein, includes whole antibodies and any antigen binding fragment (i.e., "antigen-binding portion") or single chain thereof. As used herein, the terms "automation" and "automated" are used interchangeably and refer to the controlled operation of an apparatus, process, or system by mechanical or electronic devices. Automated methods of the invention include sequential, pre-determined steps, which are internally controlled by software driven servo-actuators. Thus, the methods are standardized, efficient and free of human error.

As used herein, the terms "comprising", "consisting of" and "consisting essentially of" are defined according to their standard meaning. The terms may be substituted for one another herein in order to attach the specific meaning associated with each term.

As used herein, the term "computer system" generally includes one or more computers, peripheral equipment, and software that perform data processing. A "user" or "operator" in general includes a person, that utilizes the system of the invention such as through a user interface. A "computer" is generally a functional unit that can perform substantial computations, including numerous arithmetic operations and logic operations without human intervention. The apparatus and methods of the invention can be computer-implemented via a computer system.

As used herein, "cultureware" refers to components which come in contact with the cell product-containing aqueous medium (e.g., protein-containing aqueous medium), the purified cell product (e.g., the purified protein), or any liquid involved in the cell culture and/or purification process. The purification cultureware (i.e., the cultureware of the purification unit) includes a pre-packed, disposable, pre-sanitized or pre-sterilized selection device, e.g., a column packed with resin, which separates the protein from the contaminants contained in the protein-containing aqueous medium. The purification cultureware can further include a pre-sanitized or pre-sterilized diafiltration module which further serves to purify the protein, as well as pre-sanitized or pre-sterilized, disposable liquid reservoirs, valves, tubing, and collection vessels.

As used herein, the terms "diafiltration module" and "tangential flow filtration cassette" are used interchangeably and generally refer to membrane-based ultrafiltration devices. The diafiltration module works on the tangential flow filtration principle whereby molecules over 50,000 daltons, such as proteins (e.g., antibodies such as IgG and IgM), cannot pass through the membrane but small molecules, such as buffers, can pass through. The diafiltration module is used to exchange one buffer for another and is a more efficient substitute for dialysis. In one embodiment, the diafiltration module contains a membrane having about 50 $cm^2$ area and a normal molecular weight limit or cutoff of 50,000 daltons.

As used herein, the terms "pre-sanitized" and "sanitized" are used interchangeably and generally refer to components which have been cleaned to reduce the presence of contaminating substances and typically packaged (to remain sanitized), before use. Components which have been pre-sanitized may also be pre-sterilized or sterile. As used herein, the term "pre-sterilized" or "sterile" are used interchangeably and generally refer to components which are free from viable contaminating organisms and typically packaged (to remain sterile), before use. Accordingly, the pre-sanitized cultureware utilized in the present invention is free of contaminants which can contaminate the culture and purification process, such contaminants can include viable microorganisms. Moreover, the method of the invention does not require the steps of sanitizing or sterilizing the cultureware to be used, since the cultureware is already or has previously been sanitized/sterilized and is ready for use.

Still further, because the cultureware is disposable, the method does not require re-sanitizing or re-sterilizing components after use. As used herein, the term "disposable" refers to components which are designed to be used and then thrown away. For example, the pre-sanitized cultureware of the present invention can be designed to be used for a single purification run and then thrown away. Accordingly, the present invention provides the advantage of eliminating the time-consuming and labor intensive steps of pre-sanitizing or pre-sterilizing and pre-assembling the cultureware used to purify the biological product (e.g., protein).

By "solid phase" is meant a non-aqueous matrix to which the ligand can adhere, such as a solid phase comprising a glass or silica surface. The solid phase may be a purification column or a discontinuous phase of discrete particles. In a particular embodiment, the solid phase is a controlled pore glass column or a silicic acid column. Optionally, the solid phase is coated with a reagent (such as glycerol) which prevents nonspecific adherence of contaminants to the solid phase. Affinity ligands and methods of binding them to solid support materials are well known in the purification art. See, e.g., Affinity Separations: A Practical Approach (Practical Approach Series), Paul Matejtschuk (Editor), Irl Pr: 1997; and Affinity Chromatography, Herbert Schott, Marcel Dekker, New York: 1997.

As further used herein, "tumor antigen" describes a polypeptide expressed on the cell surface of specific tumor cells, e.g., an idiotypic tumor antigen expressed on the surface of B cells, and which can serve to identify the type of tumor. In some embodiments, the idiotypic tumor antigen is an IgM, IgG, or mixed isotype.

Cell Culture Unit

The cell culture unit of the integrated apparatus includes two individual parts: a reusable instrumentation base device (also referred to herein as a "first" reusable instrumentation base device, to distinguish it from the reusable instrumentation base device of the purification unit), and at least one disposable cell cultureware module that is used for a single production run and is disposable (also referred to herein as a "first" disposable cell cultureware module, to distinguish it from the at least one disposable cultureware of the purification unit). The instrumentation base device provides the hardware to support cell culture growth and production in a compact package, which is advantageous in a facility handling a large number of unique cell lines, for example. A pump, such as an easy-load 4 channel peristaltic pump, moves fresh basal media into the cultureware, removes spent media, adds high molecular weight factor and removes product harvest. An integrated cool storage area maintains the factor and harvest at a low temperature (preferably, approximately 4° C.). A heating mechanism maintains the cell environment to promote growth and production. The gas blending mechanism, in conjunction with the cultureware pH sensor controls the pH of the cell culture medium. A plurality of automated tube valving drives (e.g., three automated tube valving drives) are used to control the cultureware flowpath configuration to accomplish the fluidic functions necessary to initiate and carryout a successful run. Valves and sensors in the instrumentation base device control the fluid cycling in the cultureware. Drive for fluid circulation is provided. An identification code reader, such as a barcode reader, is preferably included to facilitate operator and lot tracing. A communication port preferably ties the instrumentation device to a facilities data management system (LIMS). Preferably, the instrumentation device of the cell culture unit includes a user interface, such as a flat panel display with touch screen, for user interaction.

The one-time use cultureware is provided pre-sterilized, designed for rapid loading onto the instrumentation base device ("quick-load"). The loading of the cultureware body makes connections to the instrumentation base device. The pump cassette, which is physically attached to the tubing, allows the user to quickly load the pump segments. The design and layout minimizes loading errors. The cultureware enclosure provides an area that is heated to maintain cell fluid temperature. Reservoirs to maintain fluid volumes and cycling are included in the cultureware. Sensors for fluid circulation rate and pH and thermal well for the instrument's temperature sensor are included. The blended gas from the instrumentation device is routed to the gas exchange cartridge that provides oxygen and adds or removes carbon dioxide to the circulated fluid to support cell metabolism. The cultureware module also includes a bioreactor (e.g., hollow fiber bioreactor or other bioreactor type), which provides the cell space and media component exchange. Disposable containers for harvest collection and flushing are provided. The operator attaches a media source, factor bag and spent media container to the cultureware before running. The media and spent media container is disconnected, pump cassette is unloaded, cultureware body is unloaded and the used cultureware is placed in a biohazard container for disposal.

Figure 1:
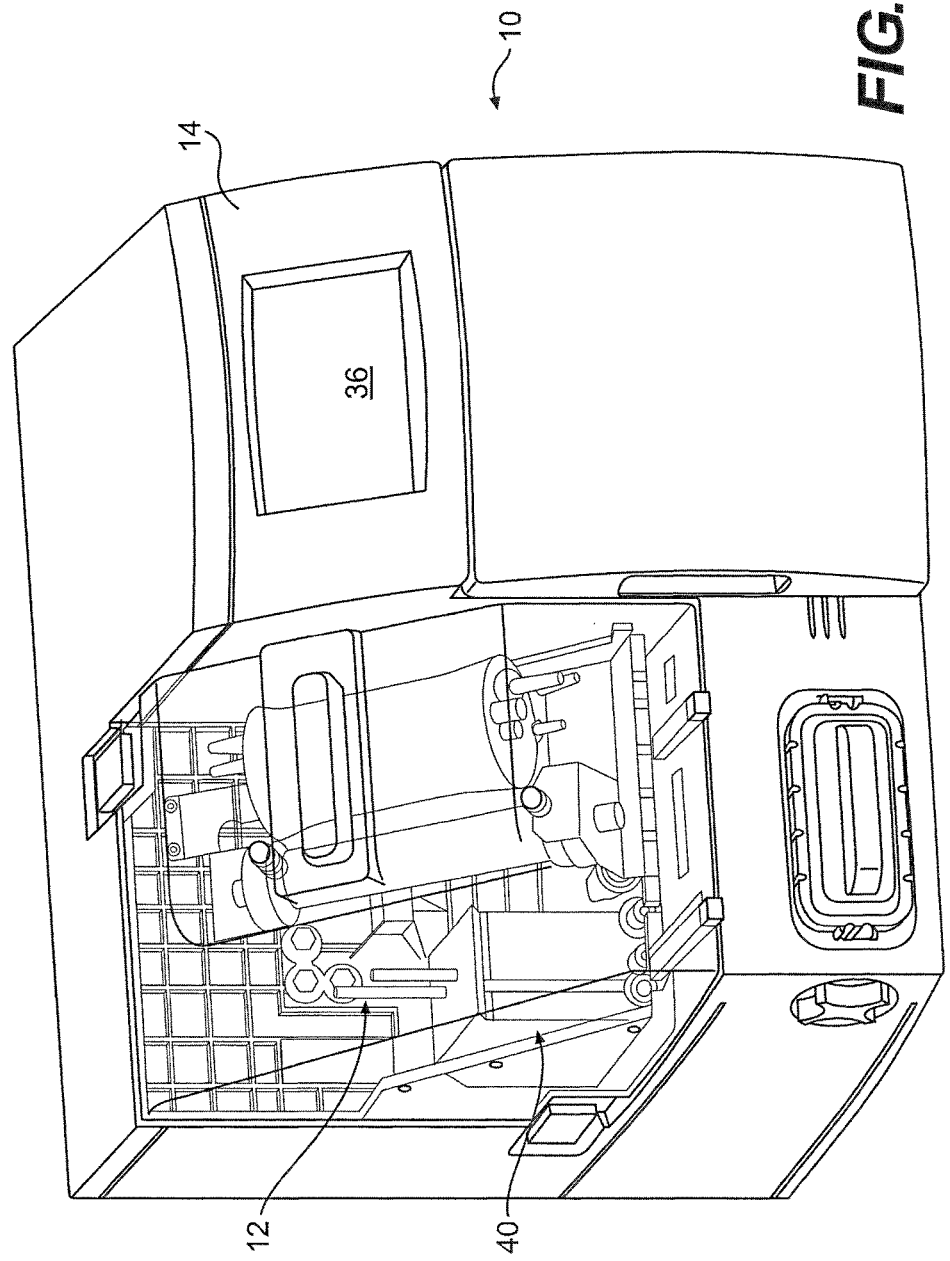
FIG. 1 is a perspective view of the cell culture unit for producing cells and/or cell derived products according to the present invention.

Referring to FIG. 1, the present invention provides a fully integrated cell culture unit 10 for producing cells and cell derived products in a closed, self-sufficient environment. More specifically, the cell culture unit allows for cell expansion and harvest of cells and their products with minimal need for technician interaction. As will be described further herein, the device incorporates cell culture technology, for example, hollow fiber or similar bioreactor perfusion technology, with all tubing components, harvest tubing and tubes threaded through the pump cassette, encased in a single-use, disposable incubator 12. Following bioreactor inoculation with cells, the apparatus follows pre-programmed processes to deliver media, maintain pH, maintain lactate levels, control temperature and harvest cells or cell-secreted protein. Standard or unique cell culture growth parameters can be programmed, such that, various cell types can be expanded and such that cells or cell products can be harvested in an efficient, reproducible manner with minimal chance of human error. The cell culture system and method described in International Publication No. WO 2007/139742, "Method and System for the Production of Cells and Cell Products and Applications Thereof" (Wojciechowski R. et al.), is hereby incorporated by reference in its entirety.

The cell culture unit is based on cell growth chamber technology. For example, bioreactors that have a plurality of semi-permeable hollow fibers or other type of semi-permeable membrane or substrate potted in a housing to create a space inside the fiber or one side of the membrane (referred to as intracapillary or IC space) separate from that outside the fibers or on the other side of the membrane (referred to as extracapillary or EC space). Fluid distribution between the IC and EC space occurs through the fiber pores which can range in size from 10 MW(Kd) to 0.2 µm. Cells are placed on one side of the fiber or membrane, usually in the EC space, in a complete cell culture medium, which is usually the same medium used to expand cells prior to bioreactor inoculation (serum containing, serum-free, or protein-free medium). Cells are usually placed in the EC space when secreted protein is the desired product. In some instances, when cells are the desired product, it may be beneficial to place cells in the IC space.

Medium is perfused through a bioreactor 20 by circulating through the IC space at a fast rate. The medium can be a liquid containing a well defined mixture of salts, amino acids, and vitamins that often contain one or more protein growth factors. This serves to deliver nutrients to the cell space and conversely, removes or prevents a toxic build-up of metabolic waste. During this circulation, medium is passed through an oxygenator or gas exchanger cartridge 24 which serves to provide pH control and oxygen for the cells and conversely, remove carbon dioxide from the culture. When the bioreactor 20 contains a smaller number of cells, just after inoculation, the oxygenator or gas exchange cartridge is used to provide $CO_2$ and subsequently control pH of the culture environment. As cell number increases, the oxygenator is used to remove $CO_2$ which serves to enhance acid neutralization and control the pH of the culture. Other bioreactor configurations, in addition to hollow fibers, that are designed and optimized for the growth and production of cells and production of cell-derived products may also be used.

The cell culture unit 10 provides significant efficiencies and cost reduction through its disposable component and enclosed operation. As such, cells are contained in a closed system and continuously cultured without the need for specialized, segregated clean rooms. This fully integrated apparatus eliminates the need for cleaning and sterilization validations, as well as the need for hard plumbing associated with conventional cell culture facilities.

Figure 2:
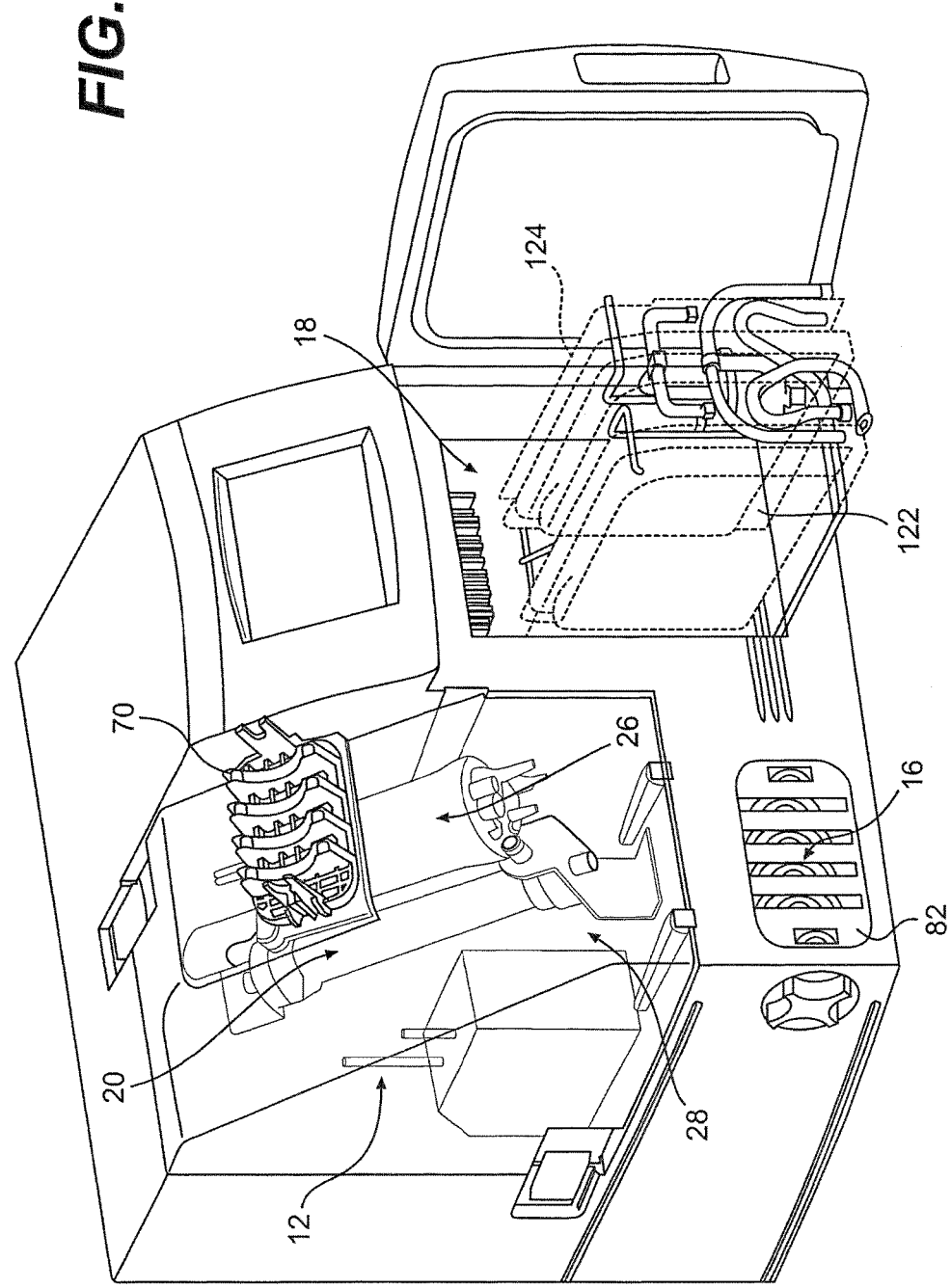
FIG. 2 is another perspective view of the cell culture unit of the present invention.
Figure 5:
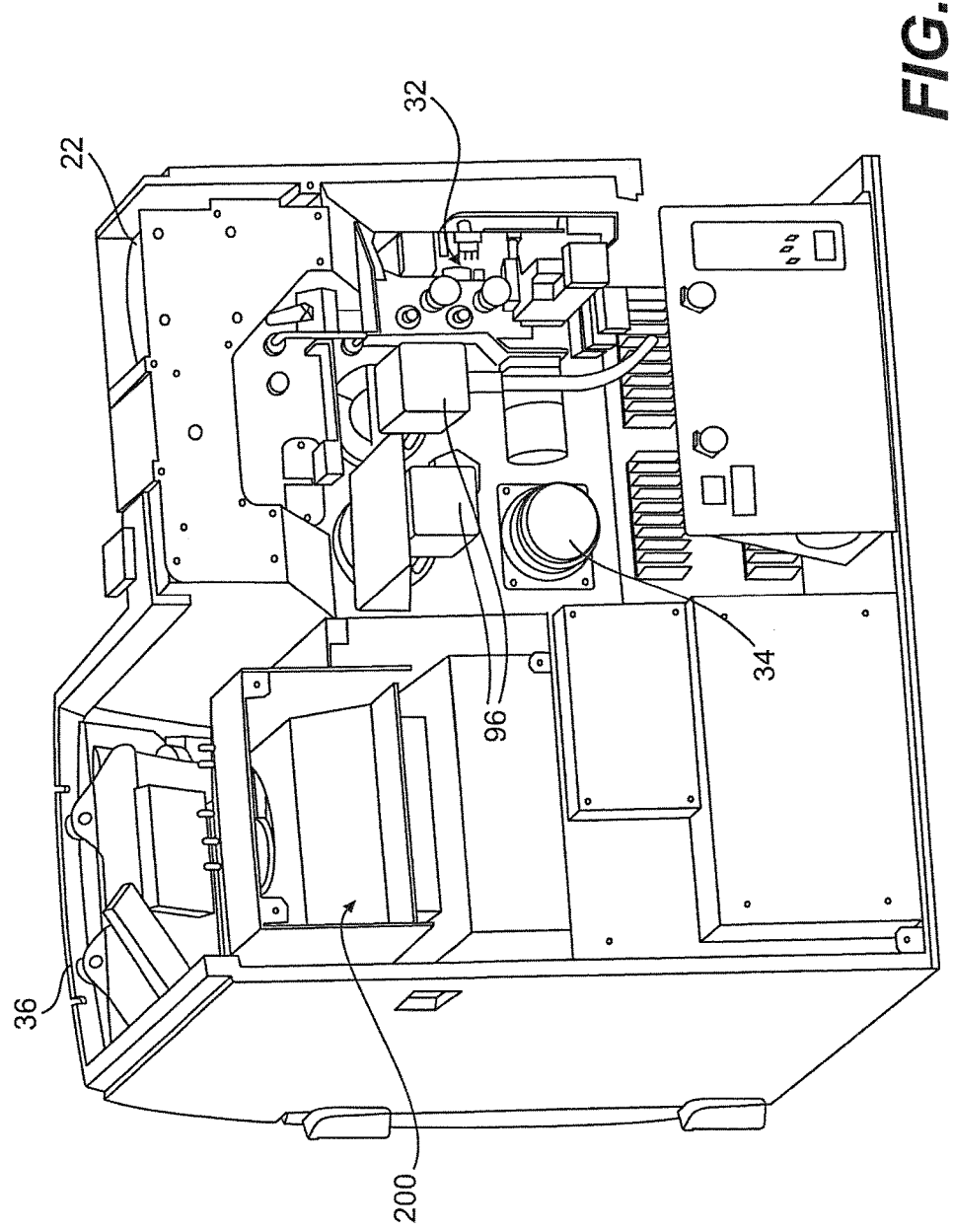
FIG. 5 is a rear view of the instrumentation device of the cell culture unit of FIG. 3, with covers removed.
Figure 6:
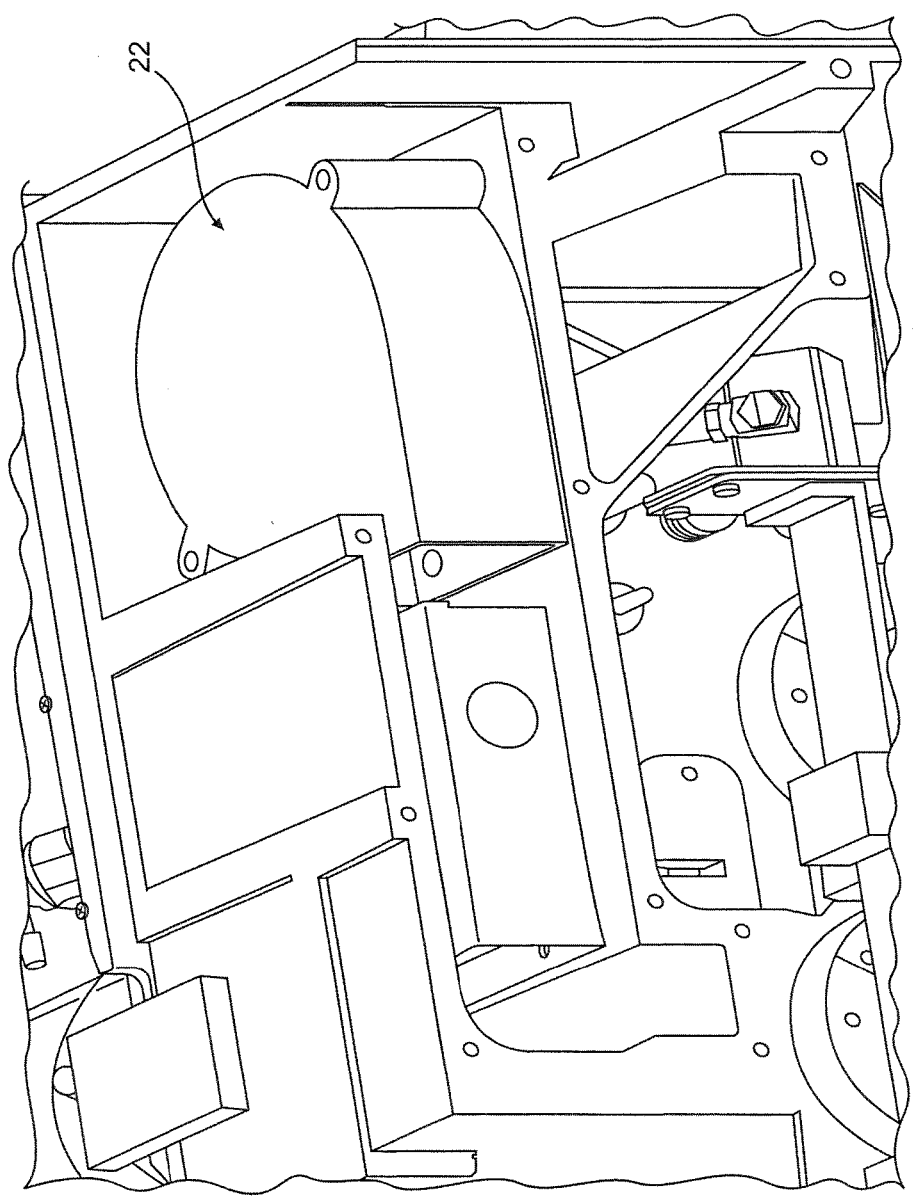
FIG. 6 is an enlarged view of the heating system of the instrumentation device of the cell culture unit of FIG. 3.

Referring again to FIG. 1, the cell culture unit includes two individual parts: an instrumentation base device 14 that is reusable and an enclosed cultureware module 12 that is used for a single production run and is disposable. Numerous modules 12 can be used on a single device 14. The instrument provides the hardware to support cell culture growth and production in a compact package. As shown in FIG. 2, and as will be described in further detail herein, an easy-load multiple channel peristaltic pump drive 16 located in base device 14 and a pump cassette 70 move fresh basal media into the cultureware, removes spent media, adds growth factors or other supplements and removes product harvest. An integrated cool storage area 18 maintains the factor and harvest at a low temperature (approximately 4° C.). An integrated heating mechanism 22 (FIG. 6) maintains the cell environment to promote growth and production. Gas exchange cartridge 24 (FIG. 5), in conjunction with a cultureware pH sensor 26 controls the pH of the cell culture medium. Two automated tube valving drives 90 (FIG. 3) are used to control the cultureware flow path configuration to accomplish the fluidic switching functions needed to initiate and do a successful run. Valves 90 and sensors 32 (FIGS. 3, 5, 13) in the instrument control the fluid cycling in the cultureware module 12. A pump drive 34 (FIGS. 3, 5) for fluid circulation is provided. A wireless or tethered (attached) identification code reader (such as a barcode reader), shown in FIG. 33, facilitates operator and lot tracing. An identification code comprises an identifier on or made part of a surface such as cultureware module or user identification tag, and which may include, but is not limited to, a bar code, a number, a series of numbers, a color, a series of colors, a letter, a series of letters, a symbol, a series of symbols, and a combination of one or more of the foregoing. Other examples include radio frequency identification (RFID) tags, bokodes, and quick response (QR) codes. A communication port ties the instrument to a data information management system (such as a MES). A user interface 36, such as a flat panel display (shown in FIGS. 1 and 33) with touch screen capability, is available for user interaction.

The one-time use cultureware module 12 of the cell culture unit is provided pre-sterilized. It is designed for quick loading onto the instrument ("quick-load"), as will be described further herein. The loading of the cultureware body makes connections to the instrument. Pump cassette 70 (FIG. 2), which is physically attached to the tubing, allows the user to quickly load the pump segments. This design and layout minimizes loading errors. The cultureware enclosure 12 provides an area that is heated to maintain cell fluid temperature. A fluid cycling unit 40 (FIGS. 1, 18) maintains fluid volumes and cycling and is included in the cultureware. Sensors for fluid circulation rate, pH and a thermal well for the instrument's temperature sensor are provided. The blended gas from the instrument is routed to gas exchange cartridge 24 that provides oxygen and adds or removes carbon dioxide to the circulated fluid to support cell metabolism. A magnetically coupled pump drive 34 (FIGS. 11-12) circulates fluid thru the bioreactor 20 and gas exchange cartridge 24. The bioreactor 20 that provides the cell space and media component exchange is also in the cultureware. Disposable containers for harvest collection are provided. Prior to the beginning of the culture, the operator (also referred to herein as the user) attaches a media source, factor bag and spent media container to the cultureware before running. At the conclusion of the run the harvest containers are removed or drained, media and spent media container is disconnected, pump cassette is unloaded, harvest bag disconnected, cultureware body is unloaded and the used cultureware is placed in a biohazard container for disposal.

Cell expansion and subsequent process tracking mandates generation of a batch record for each culture. Historically, this is done with a paper-based system that relies on operator input of the information. This is labor intensive and subject to errors. The fully integrated apparatus of the invention can incorporate an identification code reader, such as a barcode reader, and data gathering software which, when used with the information management system (MES), allows for automatic generation of the batch record.

The apparatus of the present invention has application in a regulated cell culture environment. It is anticipated that autologous whole cell therapies or patient-specific proteins (vaccines) therapies, would by their nature, require the simultaneous culture of numerous cell lines in a single facility. In addition to the segregation created through this closed culture approach, the apparatus is designed to support a standard information management system (such as a LIMS or MES) protocol. This capability contributes to the creation of thorough batch records and verification of culture conditions to ensure standardization, tracking and safety of each product. This capability facilitates the multi-product concept that is pivotal to facilities involved with autologous or patient-specific products.

Figure 10:
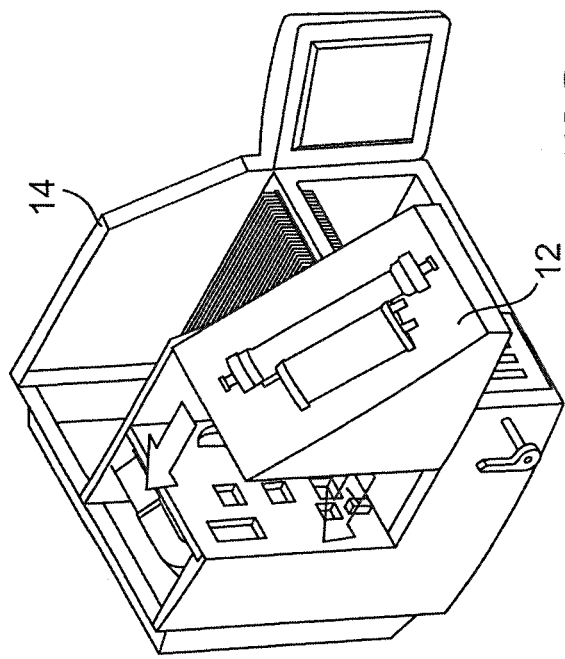
FIG. 10 illustrates the installation method of the cell culture module and instrumentation device of the cell culture unit of the present invention.

Referring to FIG. 1, disposable cell culture module 12 is removably attachable to instrumentation base device 14. The module requires multiple mechanical and electrical interfaces to the control instrumentation of device 14. Module 12 has interface features integrated into the module that mate with instrument interface features in the device to allow for a single motion installation (FIG. 10). As modules 12 are to be disposed of after use, it should be appreciated that numerous modules can be used in conjunction with a single base device 14.

Figure 3:
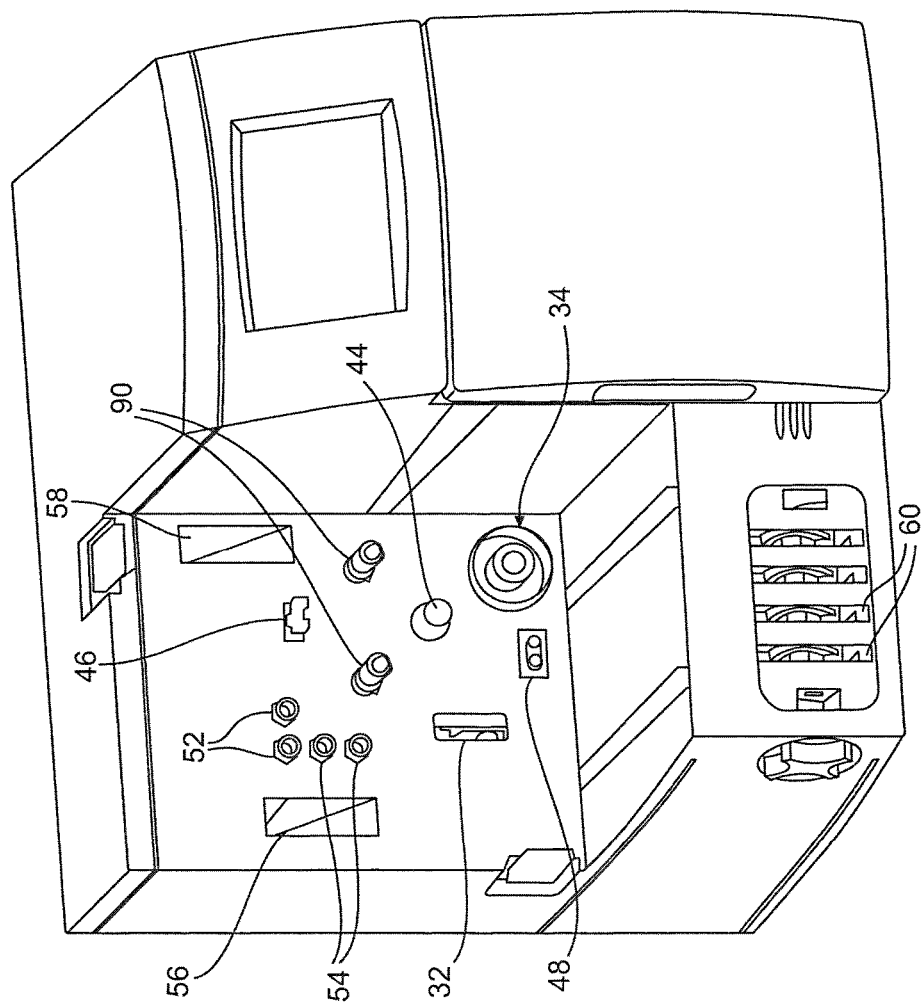
FIG. 3 is a perspective view of the instrumentation device of the cell culture unit of the present invention.
Figure 4:
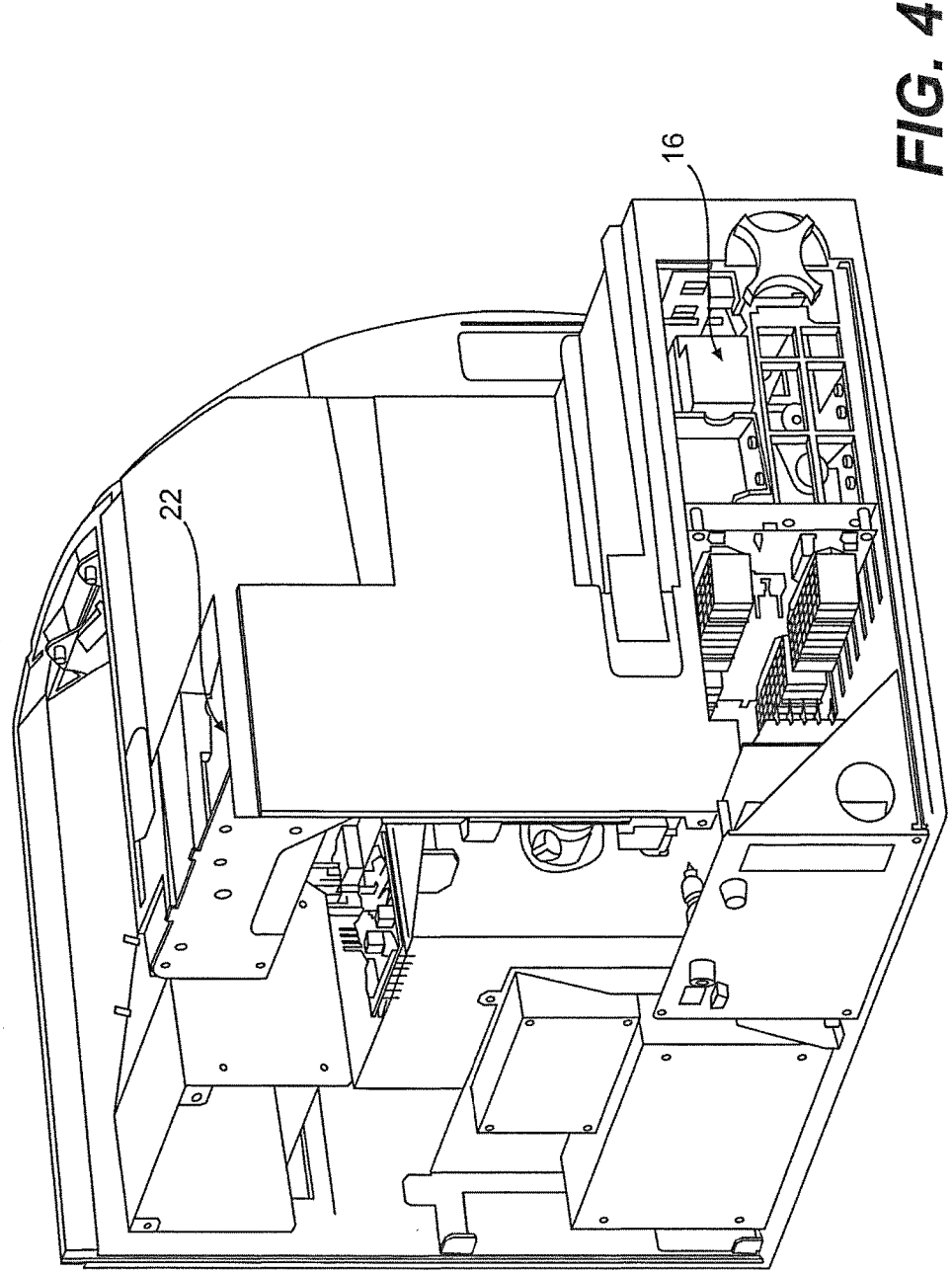
FIG. 4 is a rear and partial side view of the instrumentation device of the cell culture unit of FIG. 3, with covers removed.

As shown in FIG. 3, the interface features of device 14 include circulation pump drive 34, actuator valves 90 and cycling sensor 32. In addition, a temperature probe 44 and a flow sensor 46 interface with the components of module 12. Device 14 also includes an electrical connection 48 for pH probe 26 disposed within module 12.

Gas ports 52 communicate with gas exchanger 24. One port 52 communicates with the input to exchanger 24 and the other port 52 communicates with the output of the exchanger. Gas ports 54 control pressure to the cycling fixture 40. One port 54 communicates with the IC chamber and the other port 54 communicates with the EC space. As viewed from the front, the left port 52 is the exchanger output and the right port 52 is the exchanger input. The top port 54 is the IC reservoir pressurization port, and the lower port 54 is the EC reservoir pressurization port.

As described above, module 12 is heated to maintain cell fluid temperature. Heating mechanism 22 (FIG. 6) maintains the cell environment to promote growth and production. The cell culture, disposable modules 12 requiring elevated temperatures are warmed by fully encapsulating the module and attaching the module to the controlling instrument device 14, such that air ports are aligned and warmed air is forced into the module from the instrument at one location and allowed to escaped at another. Instrument device 14 has a heated air outlet 58 and a return heated air inlet 56.

When disposable module 12 is installed onto the controlling instrument device 14, the air inlet 88 (FIG. 19) of the disposable module aligns with the air outlet 58 of the controlling instrument. Heating mechanism 22 forces warmed air through outlet 58 and into the warmed air inlet 88 and into disposable module 12. The warmed air elevates the temperature of the components inside of the module. The exhaust air exits through air outlet 86 and into air inlet 56 of instrument device 14 where it is circulated.

Figure 19:
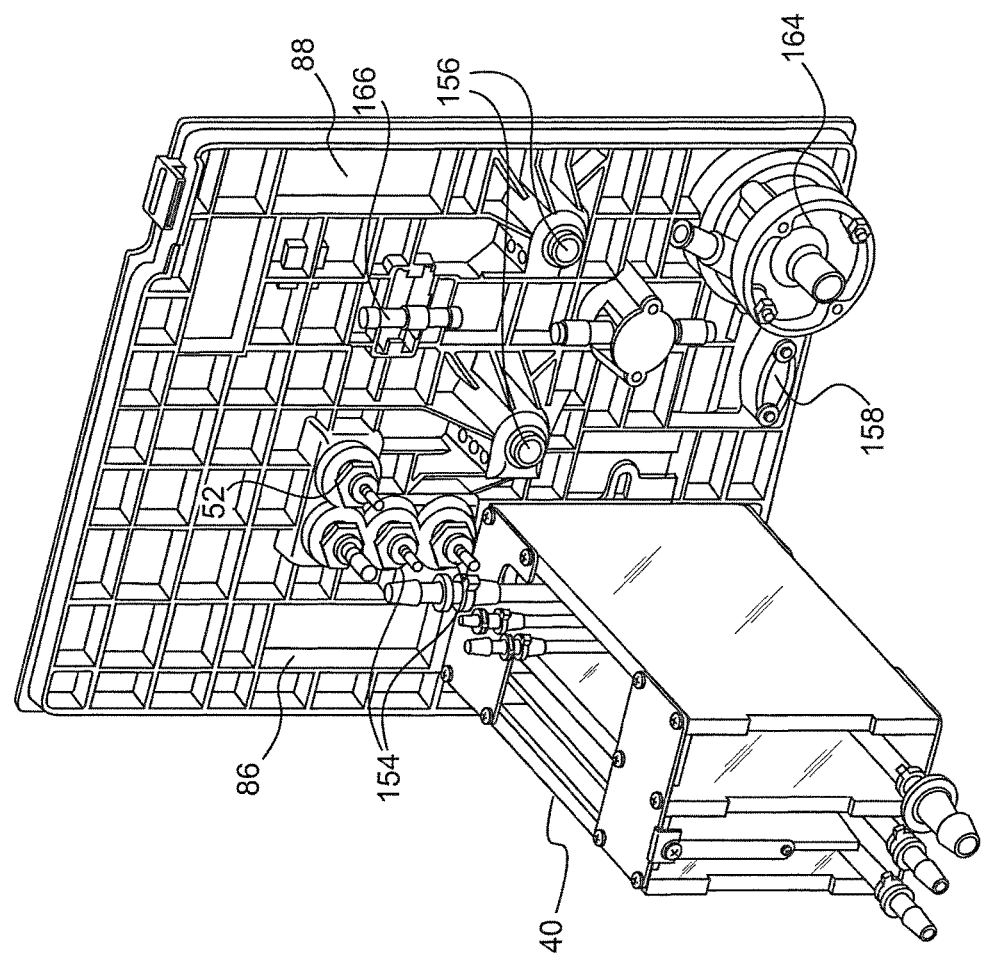
FIG. 19 is a perspective interior view of the back of the module of FIG. 17.

During installation, module 12 is aligned with the connections of the device 14 and the module is placed into the operating position as shown in FIG. 10. All mating interface features are functional. Referring to FIG. 19, when installed, certain features of the module 12, formed in a back panel 148 of the module, interface with device 14. Module air outlet 86 aligns with device air inlet 56 and module air inlet 88 aligns with device air outlet 58 to circulate heated air through module 12 as described herein. Gas connectors 152 and 154 engage device gas ports 52 and 54, respectively, to allow gas to enter and exit module 12. Valve bodies 156 receive actuator valves 90. Hub 158 receives pH probe 26 interface and aligns with electrical connector 48. Module 12 is connected to circulation pump drive 34 via module pump connection 164. Cycling unit 40 also communicates with cycling sensor 32 when the module is installed. The flow sensor 46 of device 12 mates with flow sensor connection 166. The temperature sensor 44 of device 14 mates with a non invasive receptacle in module 12 that is in contact with the IC media to provide control feed back to the control mechanism to regulate the thermal output of heater 22. The above mating connections facilitate the one-motion installation of the module 12 on the device.

Figure 7:
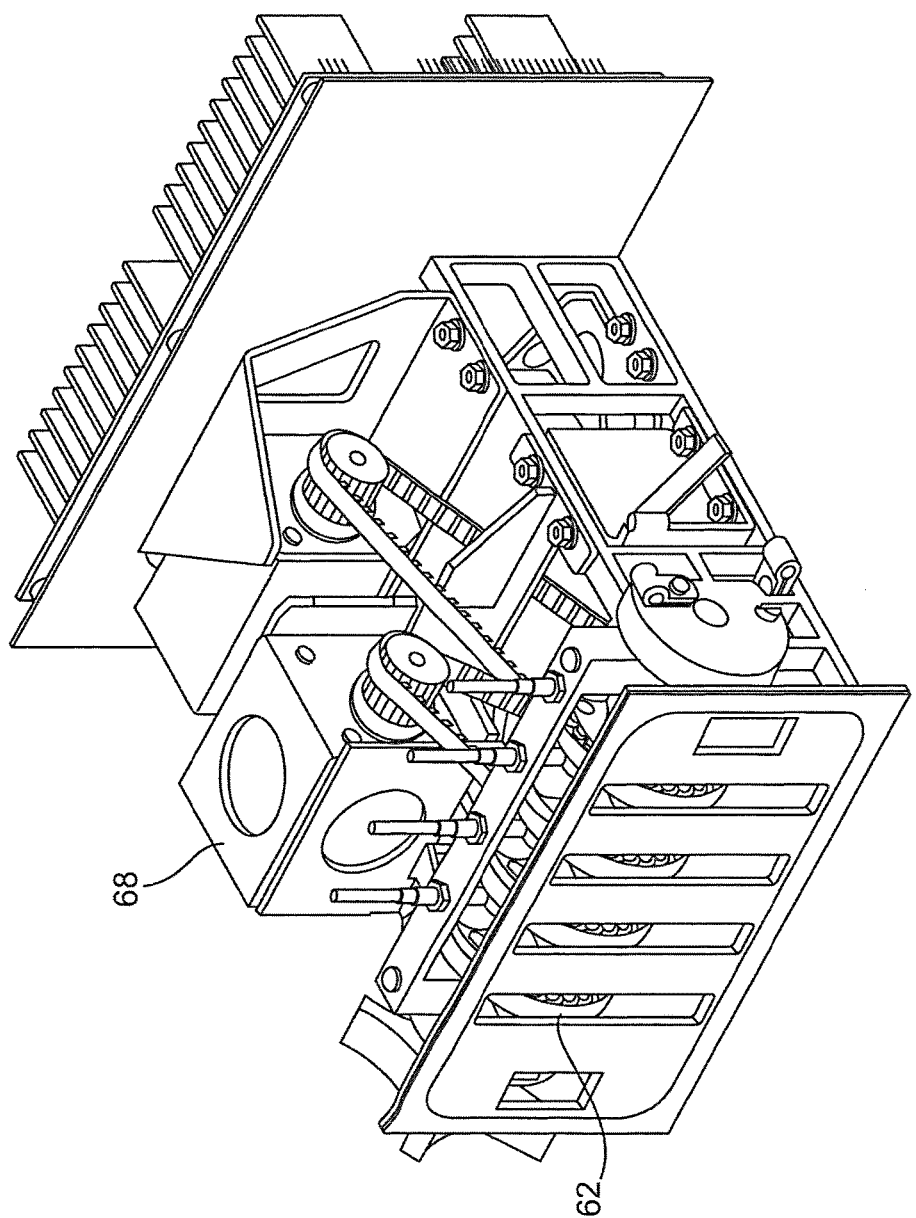
FIG. 7 is a perspective view of the variable output pump of the cell culture unit of the present invention.
Figure 8:
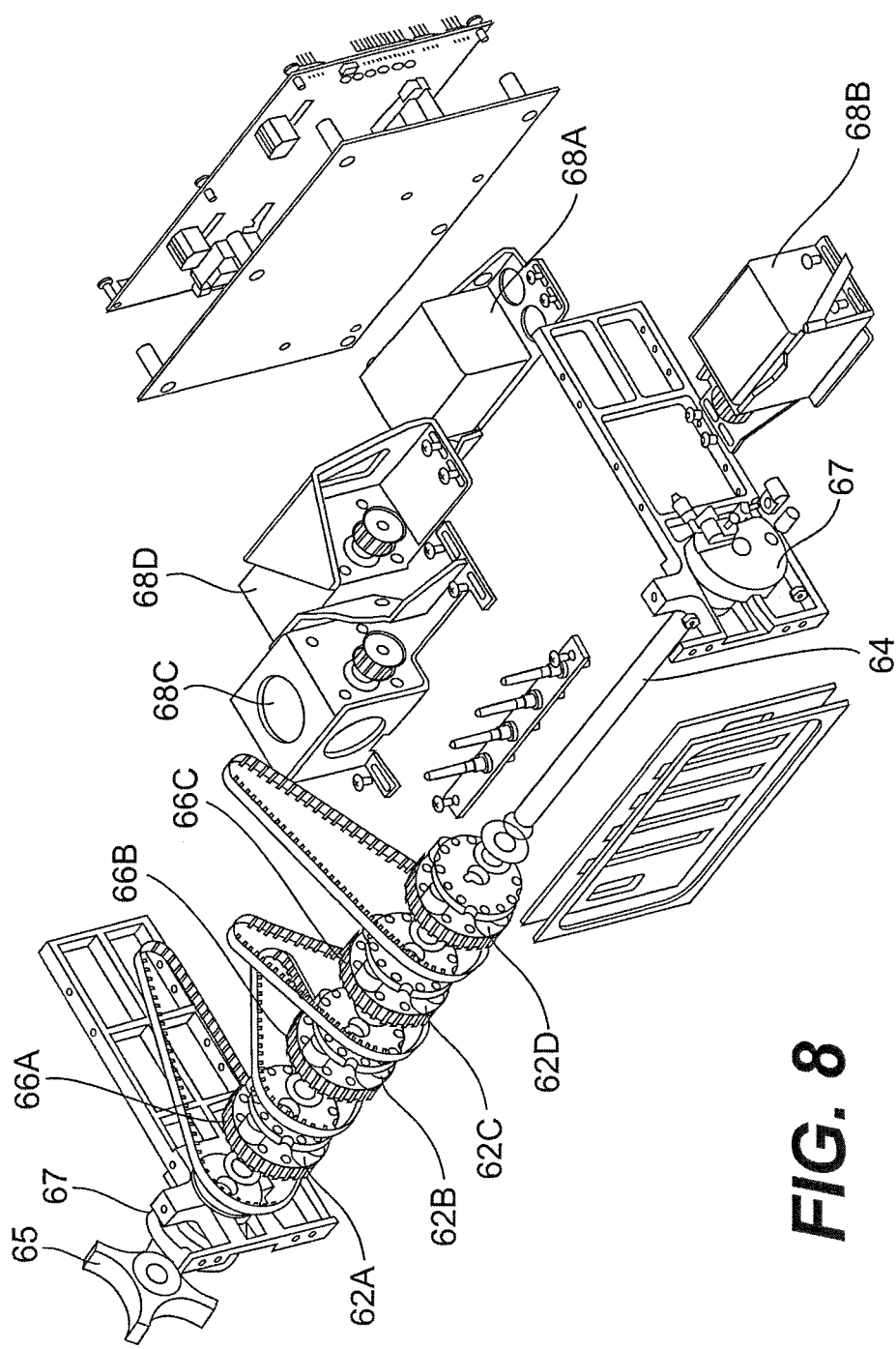
FIG. 8 is an exploded view of the pump of FIG. 7.
Figure 9:
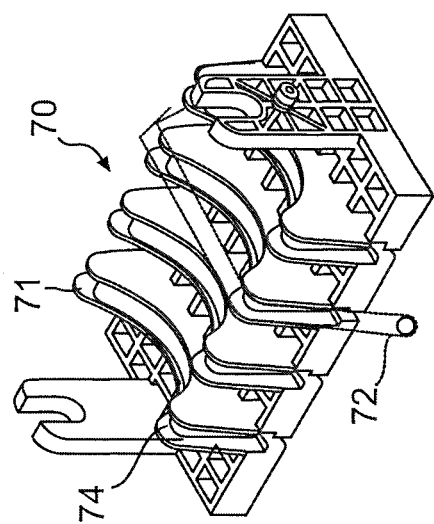
FIG. 9 is a perspective view of the pump cassette of the apparatus of the present invention.

Referring to FIGS. 7-9, the present invention incorporates a multi-position, cassette loading, and peristaltic pump 16 (FIG. 2) with discrete, variable output control for each channel. A plurality of channels 60 (FIG. 3) are located in device 14. Although four channels are shown, it should be appreciated that pump 16 could have more or less channels.

As shown in FIG. 8, the pump has individual, variable control of the output of each channel. Pump rotors 62A-62D have a common fixed axial shaft 64 with individual servo drive. The occlusion rotors 66A to 66D are mounted to the pump rotors 62A-62D, which in turn are mounted on the single shaft 64 with internal bearings that allow for independent functional control by a respective reacting servo drive 68A-D. The single shaft minimizes tolerance accumulations typically caused by misalignment of individual rotors and shafts mating with a multi-channel cassette. Feedback sensors are included to verify rotation of the pump rotors.

Typical multi-channel peristaltic pump applications operate using a rotating drive shaft that is common to all rotors. This causes all rotors to turn at the same revolution per minute (RPM), yielding the same fluid output. Different inside diameter tubing may be used to give a fixed ratio delta output from one rotor to another. To obtain a variable output of the peristaltic pump segments, individual pump heads and drives are used. This requires individual tubing cassettes that must be loaded individually and does not allow for close center to center distance between pump heads.

As shown in FIG. 9, a multi-channel cassette 70 is featured with pre-loaded peristaltic tubing 72 to reduce loading errors and to reduce installation time. The mechanism includes a cam operated cassette insertion feature 74) that interfaces with 67 on pump 16. As shown in FIG. 8, a knob 65 is rotated to move cam feature 74 into position to aid initial tubing occlusion during loading.

The cassette configuration is structured to hold multiple peristaltic tubing segments. A gripping feature 76 on the top and the bottom prevents the tubing from creeping during operation. The design allows for all tubing segments to be loaded into the pump drive mechanism at the same time. A latching feature 74 is also included to provide a bearing surface for the cam-operated latch 67 to react upon.

Figure 24:
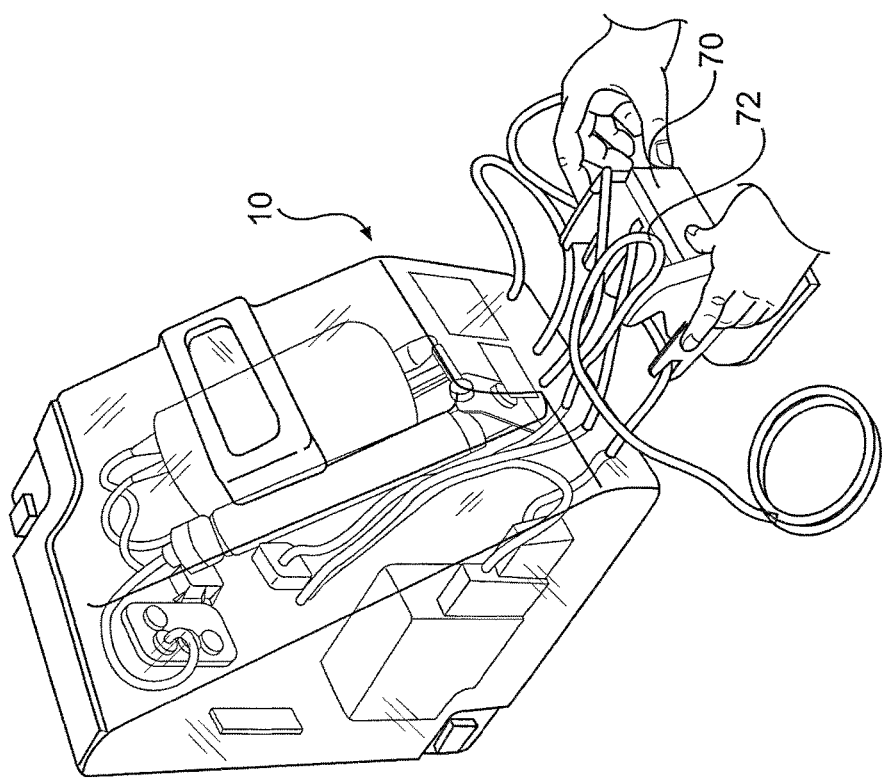
FIG. 24 is another perspective view of the cell culture unit of the present invention.

Referring back to FIGS. 1 and 2, cassette 70 is pre-loaded with peristaltic tubing (FIG. 24) and positioned in groove 80 on module 12. After module 12 is positioned on device 14, cassette 70 is removed and inserted into interface or plate 82. Each cassette section 71 (FIG. 9) supporting the tubing is inserted into a respective channel 60 (FIG. 3) of the interface 82. This configuration reduces tubing segment loading errors with pre-loaded multi-position cassettes, and reduces installation time.

Figure 11:
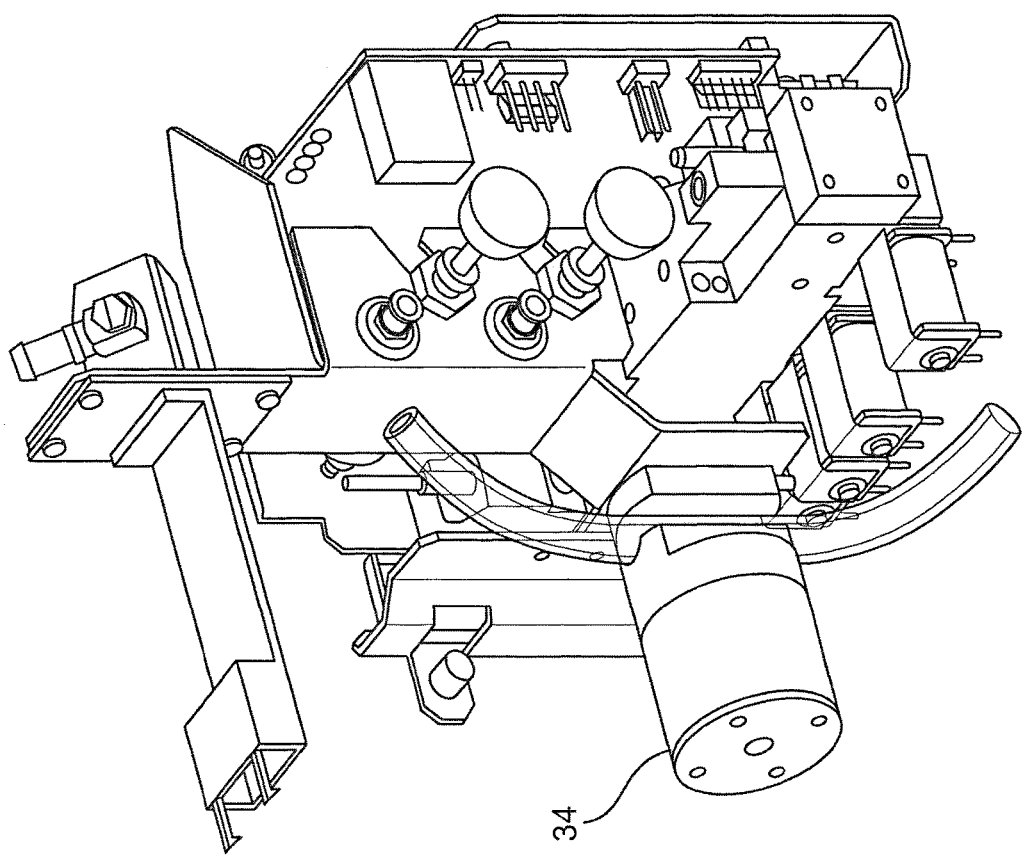
FIG. 11 is a perspective view of the gas blending and fluid cycling control of the module of the present invention.
Figure 12:
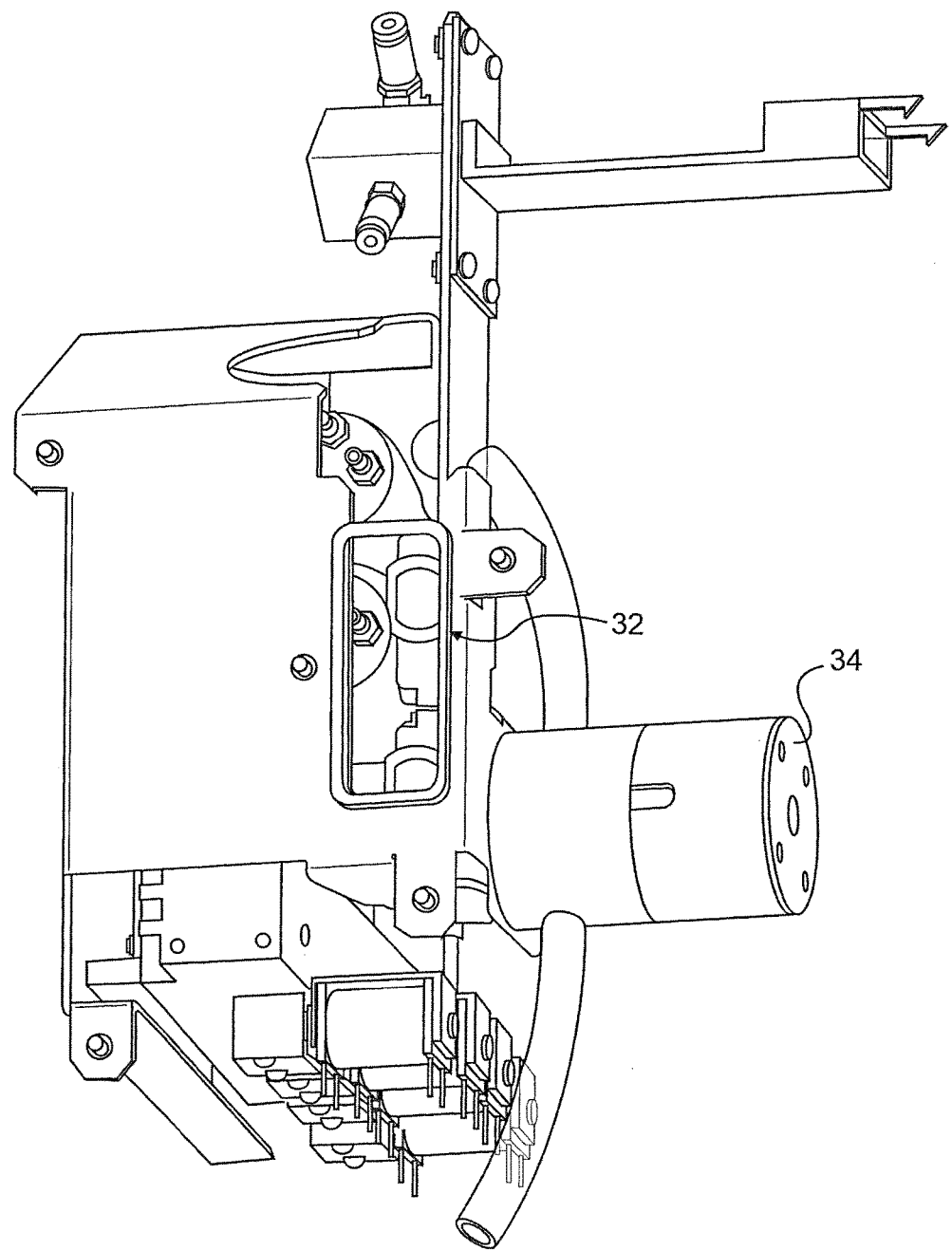
FIG. 12 is a front view of the fluid cycling control of FIG. 11.
Figure 20:
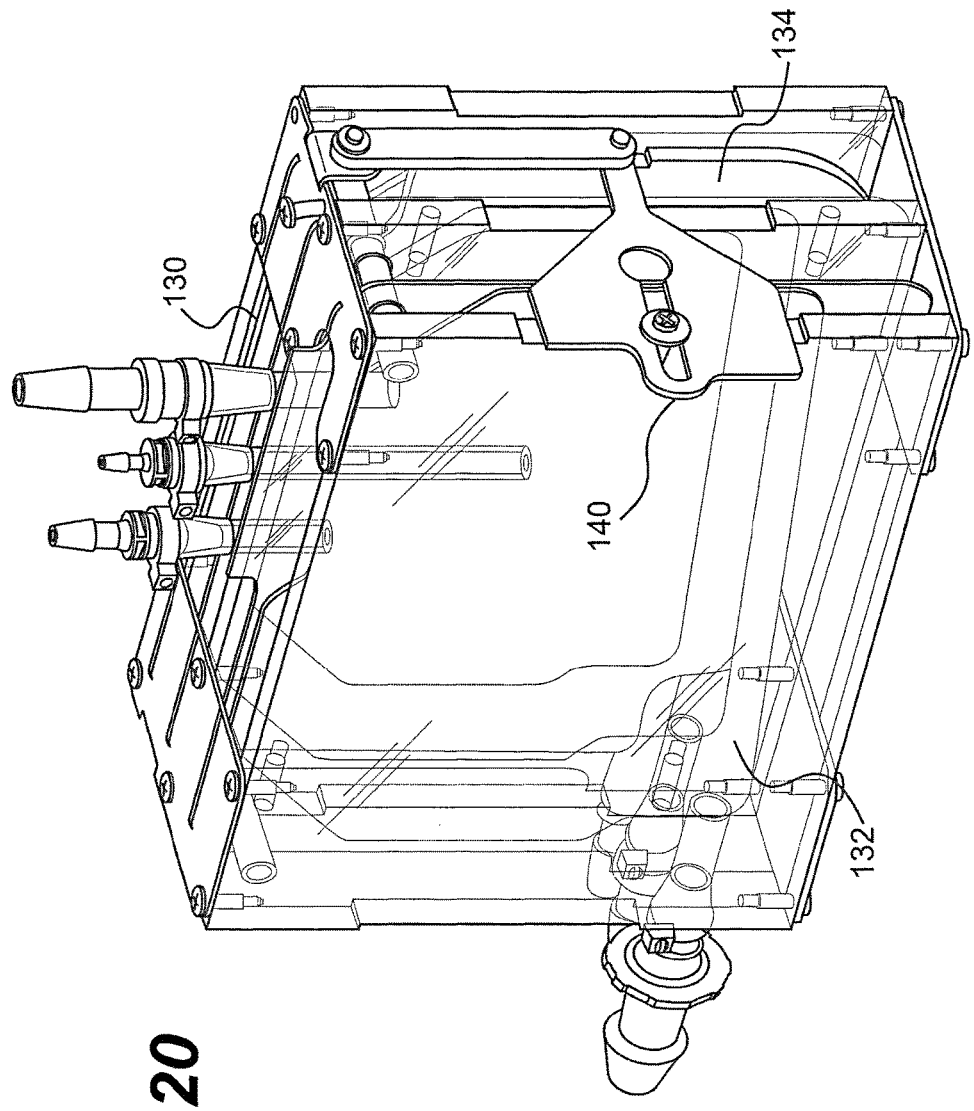
FIG. 20 is a perspective view of the extra-capillary cycling unit of the present invention.
Figure 21A:
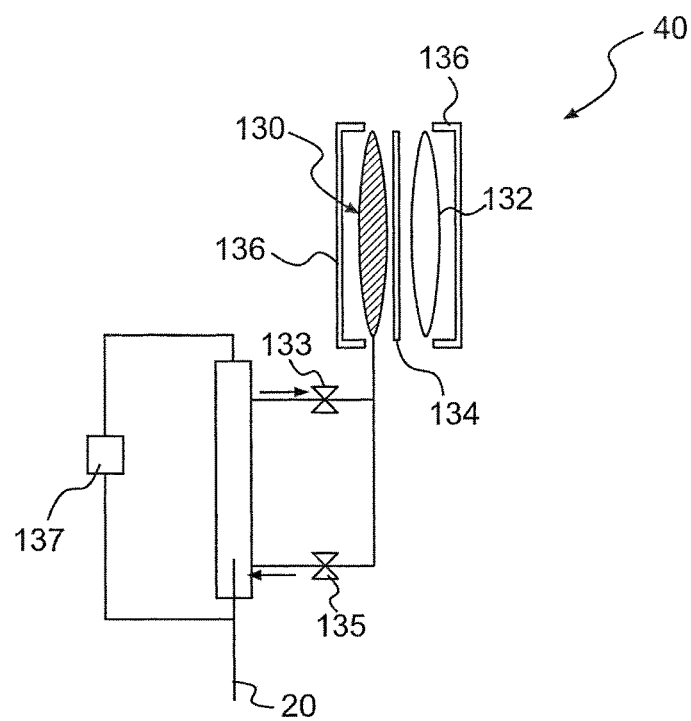
FIG. 21A is a flow diagram of the cycling unit of FIG. 20.
Figure 21B:
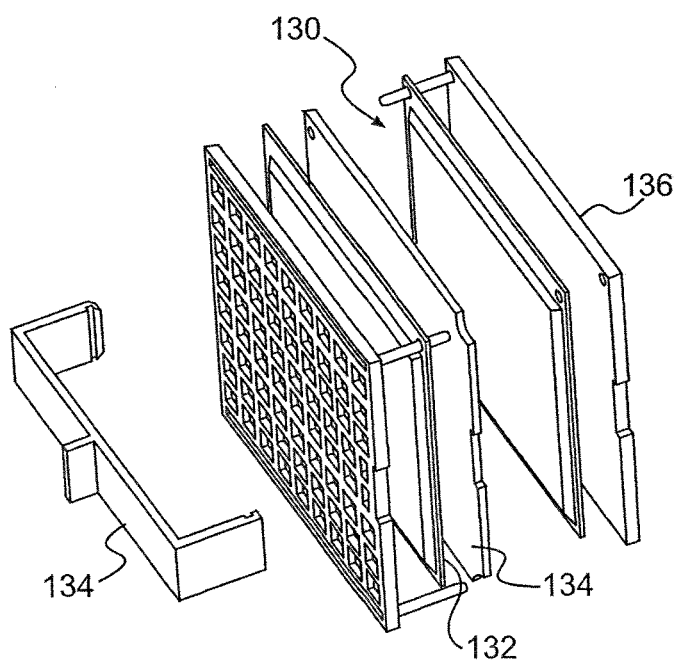
FIG. 21B is an exploded view of the cycling unit.

Referring to FIGS. 11 and 12, valves and sensors 32 in the instrument control the fluid cycling in the cultureware module 12. Two optical sensors detect the low or high position of the cycling position sensor flag 140 (FIG. 20). This information is used by a predictive algorithm to control the pressures applied to the IC chamber and EC pressure bag to effect cycling.

Figure 13:
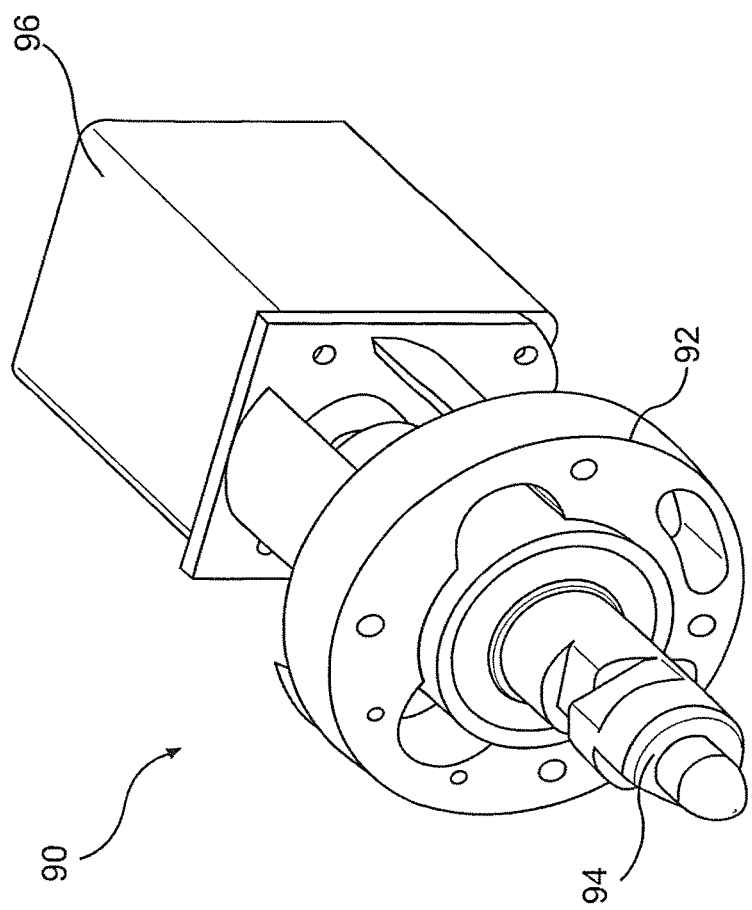
FIG. 13 is a perspective view of a rotary selection valve drive of the present invention.
Figure 14A:
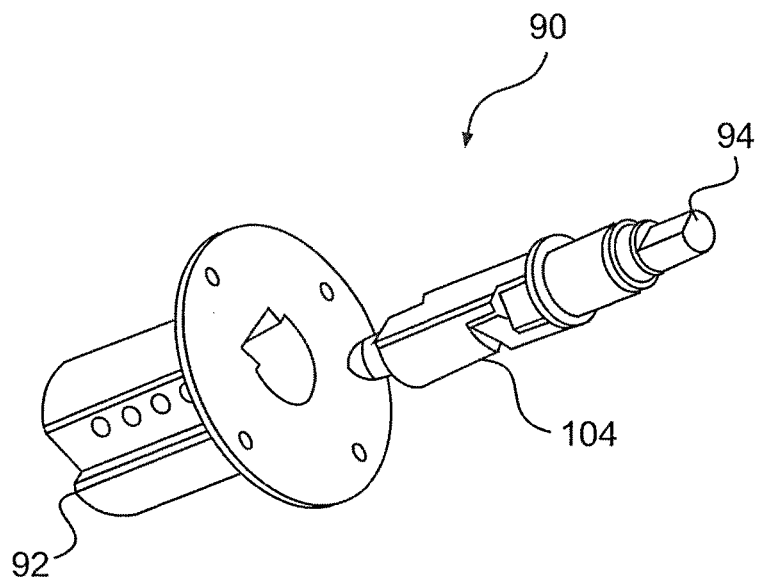
FIGS. 14A and 14B are exploded views of the valve rotor of FIG. 13, and the body used with it.
Figure 14B:
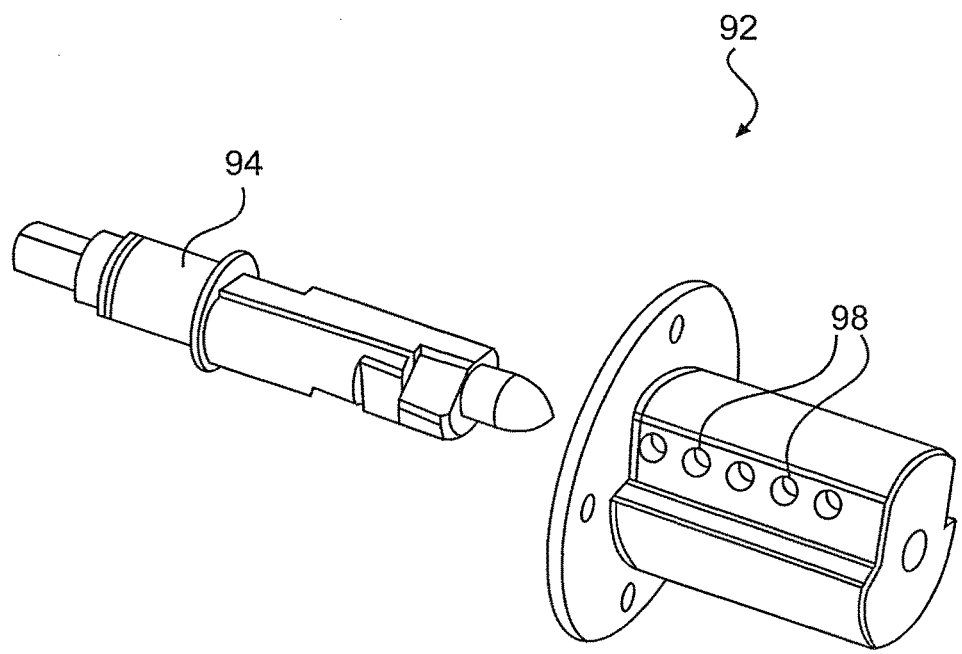

Sterilizable, disposable, actuator driven, rotary selection valves 90 are shown in detail in FIGS. 13-14C. Valve 90 comprises a valve housing 93 and valve cam 94. The elastomer tubing (not shown) is insertable through openings 98 in valve body 92 and is occluded by a rotating cam 94 that compresses the tubing against the valve body. This is accomplished by using a controlled, incremental, servo drive 96 (actuator and position feed back loop) to move cylindrical cam that reacts against immobile valve body 92 that holds the tubing in a constrained state. The cam design allows for a high area of the cam 104 to occlude the tubing and a low area of the cam 106 not to occlude, resulting in a closed and open condition respectively. Cam rotational positioning features may also be added to move cam 94 to predetermined positions. Configurations can be structured to accommodate multiple tubing segments in one device. The two piece design allows for fluid contact portion of the valve to be molded into the backpanel 148 (FIG. 19) as a hub 156 and to be sterilized (EtO, chemical or radiation) with the rest of the fluid circuit and eliminates the need to be added separately.

The design of this clamp is meant to be used in an automated cell culture application where a disposable cultureware module interfaces with an electro-mechanical instrument. The combined unit is to be automated, which required various tubing lines of the disposable to be occluded/open to provide automated process control. The selector valve is used to automatically open and close tubing lines to direct fluid or gas flow during process control. Minimizing operator set-up is also a requirement. The disposable cultureware must be inserted into the instrument in an operating position with no special operator procedures required for loading the tubing into the clamps. Existing technologies did not meet these requirements, because the manual clamps were not automated, and solenoid valves required a special operator loading procedure.

In the cell culture and purification units of the present invention, the fluid path must be free of unwanted organisms (sterilized). Commercially available selector valves are not gas sterilizable. Sealing surfaces of the selected position may be unexposed to the gas sterilant and those surfaces may be "non-sterile" when the valve is repositioned. Valve 90 provides automated actuation of the cam, compactness, multiple lines, maintains valve position even with loss of actuator power, the disposable valve body is less costly than an equivalent switching valve, and can be incorporated into the back panel of 12. Offset occluded/open cam positioning of two tubing lines can insure a make-before-break switching of fluids. No power is required to maintain any operating position, and tubing segments used in the valve body can be sterilized.

It should be appreciated that a solenoid driven pinch mechanism, can be used in place of the actuator valve. This application may utilize a piston plunger actuated by an electrical coil to provide linear motion to pinch the tubing. A manual pinch clamp could also be used. The clamping position is manually activated by a mechanical bearing surface compressing the tubing and then held in position by a detent feature. This clamp type requires manual deactivation. A membrane over the series of ports could also be used. The membrane is actuated against the port to seal it. Multiple ports are configured for use as a selector mechanism.

Figure 15B:
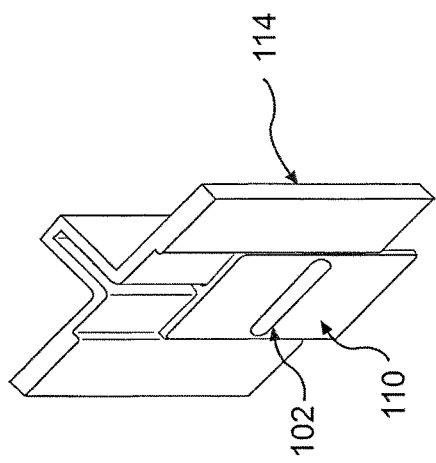
FIGS. 15A-15C are perspective views of a tubing slide clamp of the present invention
Figure 15C:
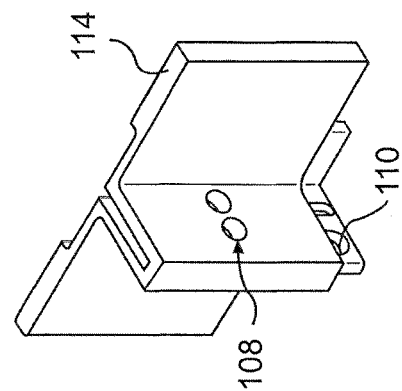
Figure 15A:
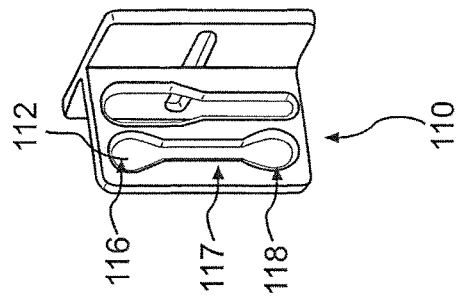

In another embodiment shown in FIGS. 15A-15C, an actuator driven tubing slide clamp 110 with multiple positions and multiple tubing can be used as an alternative to valves 90. Elastomer tubing is occluded by sliding the tubing into a narrow slot 112 that compresses the tubing wall against itself. This is accomplished by using a servo drive (actuator and position feed back loop) to move a plate 110 with slot 112 in it and reacting against another plate or slide body 114 that holds the tubing in an immobile state. The moveable plate is designed with varying width slots to allow for position/positions to be inactive. This allows for normally open 116 or 118 and normally closed 117 positions. Configurations can be structured to accommodate multiple tubing segments in one clamp.

In operation, slide 110 is positioned into slide body 114. Tubing is inserted through tubing ports 108 and slide 110 at position 116 where both tubes are not occluded. A remote servo (not shown) engages into server drive slot 102 and moves the slide to position 117 where one tube is occluded and one tube is not occluded. The remote Servo than moves the slide to position 118 where the occluded tube from the previous step is not occluded, and the tube from the not occluded tube from the previous step is now occluded. When moving the slide from position 117 to position 118, both tubes are occluded to insure that one tube is occluded before the other tube is opened. It should be appreciated that the number of tubes and configuration of the slide can be modified to meet customized applications.

The clamp is meant to be used in an automated cell culture application where a disposable cultureware module interfaces with an electro-mechanical instrument. The combined unit is to be automated, which required various tubing lines of the disposable to be occluded/open to provide automated process control. During process control the clamps are open/closed to simulate the function of an expensive, "disposable" switching valve. Minimizing operator set-up is also a requirement. The disposable cultureware must be inserted into the instrument in an operating position with no special operator procedures required for loading the tubing into the clamps. It provides automated actuation of slide clamp, compactness, multiple lines, maintains clamp position even with loss of actuator power, less costly than an equivalent switching valve. Offset occluded/open position of two tubing lines can insure a make-before-break switching of fluids. No power required to maintain any operating position.

Figure 16:
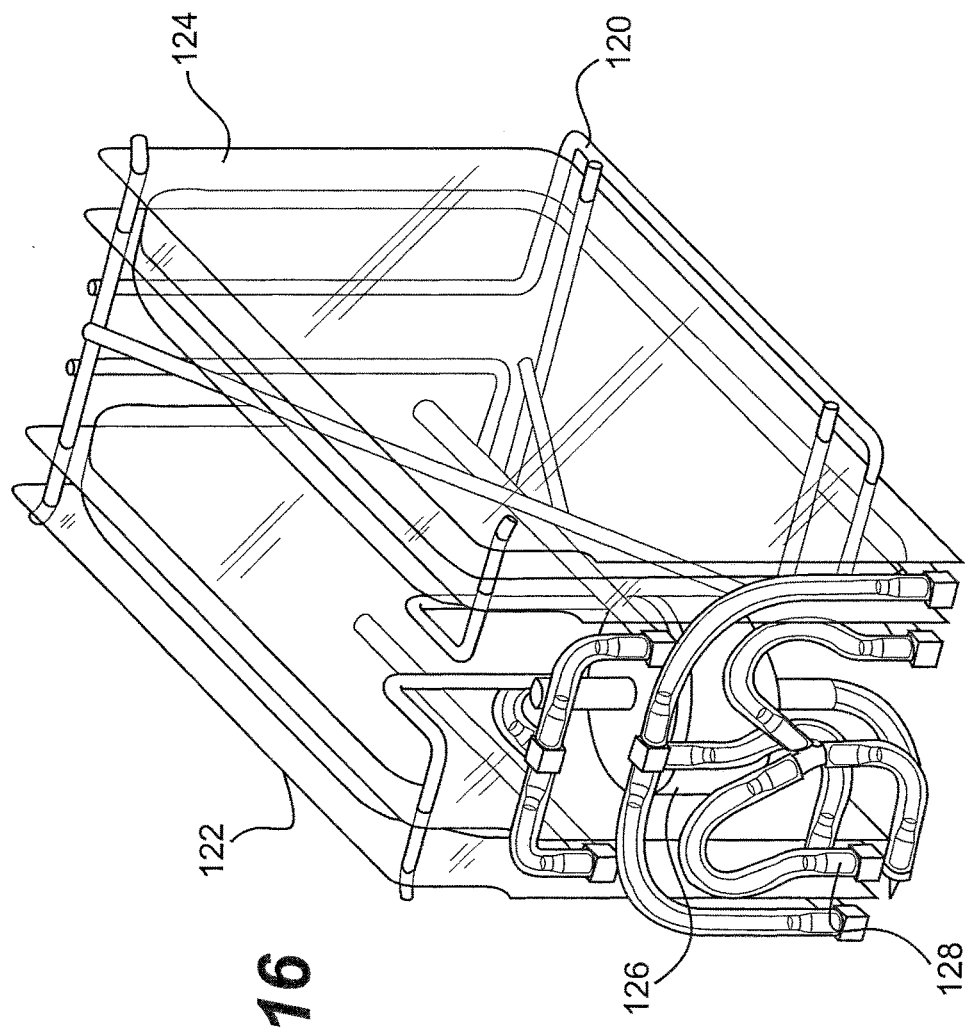
FIG. 16 is a perspective view of the factor and harvest bags of the present invention.

As described above, integrated cool storage area 18 maintains growth factors and harvested cells or cell products at a low temperature (approximately 4° C.). Referring to FIGS. 2 and 16, a rack 120 is removably positionable within cool storage area 18. Rack 120 is designed to support a plurality of bags 122, 124. The bags are used to contain the smaller quantities of product or growth factors. It should be appreciated that other solutions can be disposed with the bags. For example, high molecular weight growth factor can be located with bag 122. This factor is connected via tubing 128 to the bioreactor or cell growth chamber 20 and the flow controlled by pump 16. Harvested cells or cell products can be stored in bag 124. A cell filter 126 is provided to provide additional filtration. A filter bypass line is included if filtering of the harvest is not desired as in the case of cell collection. After the process is complete the cells can be removed from the cell culture chamber via the tubing and stored in bag 124 until use.

Figure 17:
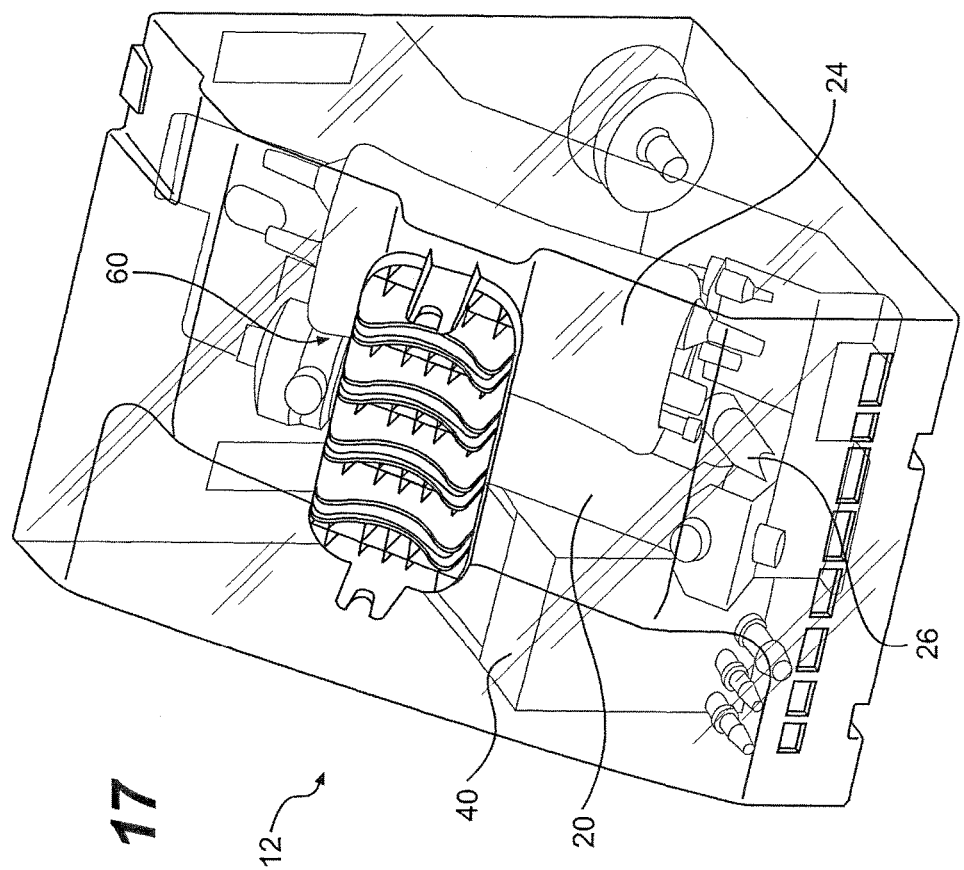
FIG. 17 is a perspective view of the disposable culture medium module of the present invention.
Figure 18:
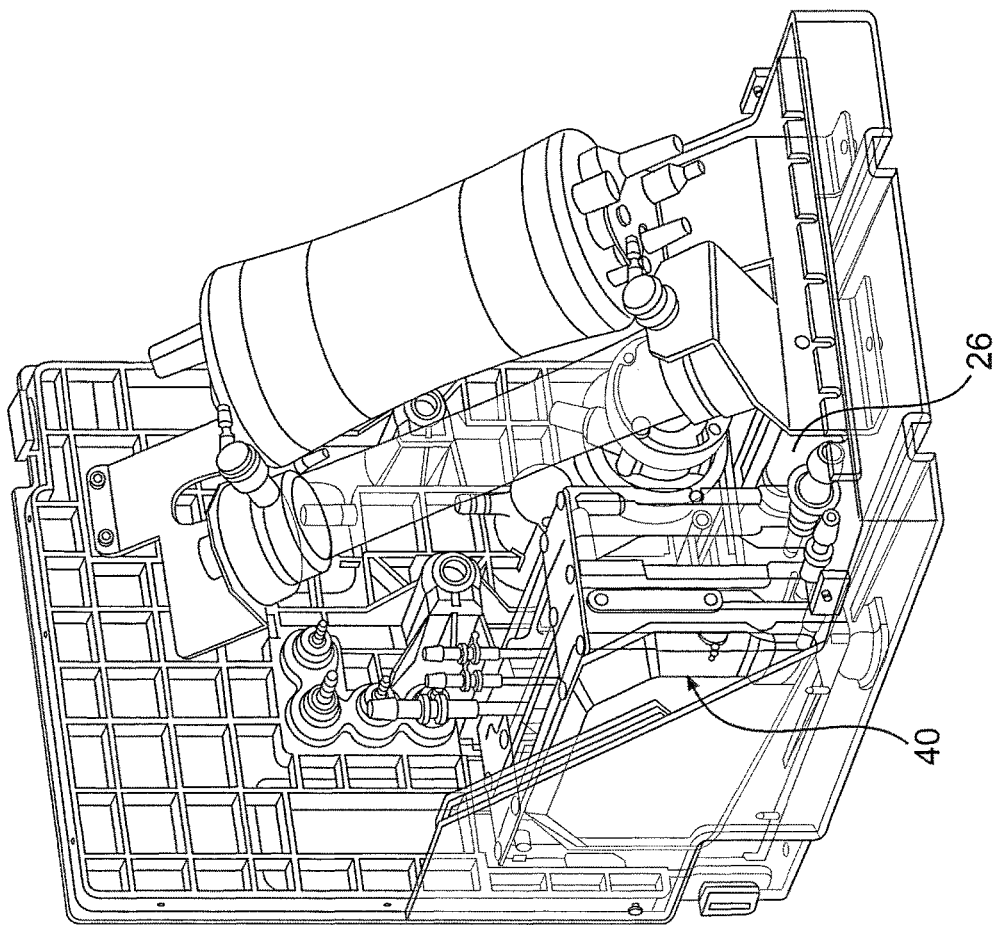
FIG. 18 is an interior view of the module of FIG. 17.

As shown in FIGS. 17-19, disposable cultureware module 12 includes fluid cycling unit 40 to maintain fluid volumes and cycling in the cell growth chamber. Referring to FIGS. 18-21, the present invention utilizes extra-capillary (EC) cycling in cell culture growth chamber 20 (FIG. 17) utilizing a non-rigid, EC reservoir 130 and mechanical or a second flexible reservoir 132 to cause elevated EC pressure. Reservoirs 130, 132 are separated by a sensor plate 134. Reservoirs 130, 132 are restricted in the maximum amount of expansion by a rigid mechanical housing 136. EC cycling is achieved by utilizing a non-rigid reservoir to retain the varying fluid volume associated with an EC circuit. Flexible reservoir 130 is fluidly connected to the bioreactor or hollow fiber device 20. Second flexible reservoir 132 is pressurized to apply force against the flexible reservoir 130 to provide an elevated EC pressure to cause an ultra-filtrative condition and force fluid into an intra-capillary (IC) circuit 138. A mechanical feed back position indicator 140 is physically connected to sensor plate 134 and moves with the physical expansion and contraction of the first flexible reservoir. The position of indicator 140 is sensed by the position sensors 32 and is used to control the force that is applied by second flexible reservoir 132. It should be appreciated that an alternate mechanical force apparatus may be used instead of a second flexible reservoir to cause pressure changes.

During operation the pressure is increased in the IC circuit 138 by pressurizing an IC reservoir 137. This pressure causes an ultra-filtrative condition that forces fluid transmembrane across the semi-permeable matrix of the bioreactor 20. The fluid is then forced through the connect tubing, through a flow control valve 133 and into the EC reservoir 130. Externally controlled pressure in the pressure reservoir 132 is allowed to vent. The expanding EC reservoir 130 forces the sensor plate 134 toward the pressure reservoir 132 and compresses it. Sensor plate 134 moves external position flag 140 and this is sensed when EC reservoir 130 has filled enough to expand to the EC upper level. The external position sensor 32 senses this position and the pressure in the IC reservoir 137, is decreased and the pressure in the pressure reservoir 132 is increased. This causes an ultra-filtrative condition and forces fluid out of the EC reservoir through a control valve 135, transmembrane across the matrix of the bioreactor 20 and into the IC circuit 138. The sensor plate 134 moves the external position flag 140 and the sensor 32 senses when the EC reservoir 130 has contracted to the EC low level.

The EC cycling unit of the present invention offers fluid dynamics to cause fluid flow in the EC space thus minimizing nutrient and metabolic waste gradients that may be detrimental to the cells. It provides fluid level control without the use of ultrasonics or load cells that is not affected by cell debris. The flexible reservoirs are considerably less expensive and are suited for disposable applications. The sealed EC reservoir with cycling also limits contamination and isolates the cells.

The present invention also includes an indirect lactate control method for perfusion culture using $CO_2$ and pH sensing. The method predicts open system, perfusion culture, lactate levels in the circulatory medium by monitoring the pH and off-gas $CO_2$ level. This is accomplished by calculating the initial bicarbonate level of the media then utilizing the liquid pH and gas level of $CO_2$ to calculate current lactate concentration. This is used to control media dilution rate of the cell culture. The resulting calculated lactate value is used to set the perfusion rate of media dilution to maintain a pre-determined lactate level. Thus, an invasive sensing system or multiple off-line sampling is not required.

A physical relationship exists between bicarbonate buffer, dCO2, and pH.

$$pH=pK+\log([HCO_3^-]/dCO_2])\qquad \text{Equation (1):}$$

where:
pH=the pH of the solution
pK=the acid ionization constant for bicarbonate
$HCO_3^-$=the current bicarbonate concentration (mM)
$dCO_2$=the concentration of dissolved $CO_2$ Lactic acid production by the cells appears to be the dominant driving force for pH changes in cell culture media. Based on this observation, each mole of lactic acid produced results in consumption of one mole of bicarbonate as described by the following equation:

$$[HCO_3^-]=[HCO_3^-]_0-[\text{Lactate}]\qquad \text{Equation (2)}$$

where:
$[HCO_3^-]_0$=the initial bicarbonate concentration in the medium (mM)
Lactate=the lactate concentration (mM)

Equation (3) provides a simple relationship—Henry's Law, that equilibrium $dCO_2$ is proportional to the gas phase concentration of CO2.

$$dCO_2=a(\% CO_2)\qquad \text{Equation (3):}$$

where:
a=$CO_2$ solubility conversion (mM/%)
% $CO_2$=concentration of $CO_2$) in the gas phase that is in equilibrium with $dCO_2$(%).

Equation (4) is derived by substituting Equation 2 in Equation 1 as follows:

$$pH=pK+\log\{([HCO_3^-]_0-[\text{Lactate}])/[dCO_2]\}\qquad \text{Equation (4)}$$

Equation 5 is derived by combining Equations 3 and 4:

$$pH=pK+\log\{([HCO_3^-]_0-[\text{Lactate}])/[a(\% CO_2)]\}\qquad \text{Equation (5)}$$

The operating equation, Equation (6) is derived by solving for Lactate in Equation (5):

$$\text{Lactate}=[HCO_3^-]_0-(a)*(\% CO_2)*10^{(pH-pK)}\qquad \text{Equation (6):}$$

The values of pK and (a) were found to be 6.38 and 0.39, respectively.

Upon taking a lactate and pH reading, the value of (a) is calculated. The initial bicarbonate concentration is calculated as the calibration constant. The advantage is that the bicarbonate concentration does not have to be known when using the present calibration method.

Figure 22:
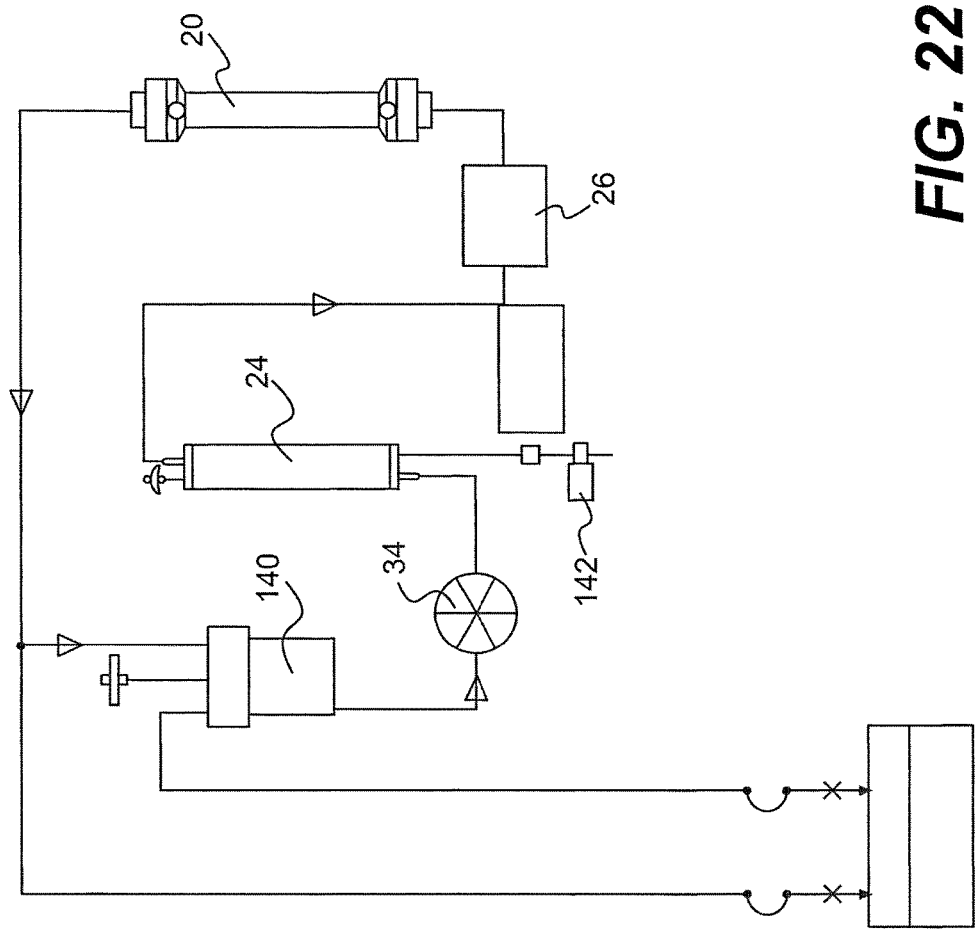
FIG. 22 is a flow diagram of the lactate control system of the present invention.

The application is shown in FIG. 22. In a bioreactor perfusion loop, the growth media is pumped from an IC reservoir 137 via pump drive 34, 164, circulated to the gas exchange cartridge (GEX) 24, pH sensor 26, bioreactor 20, and then back to reservoir 137. Blended gases are passed through the membrane gas exchange cartridge that oxygenates the media and regulates $CO_2$. Per Henry's Law, the $CO_2$ levels in the gas phase or air side of the GEX 24 is in equilibrium with the liquid phase of the media. The discharge end of the GEX is monitored with a $CO_2$ sensor 142 that resides in the device 14 and the lactate is calculated per Equation (6). When the media lactate level is known, the instrument uses automatic, media dilution, control to maintain the predetermined set point.

The present invention utilizes existing signals and with the addition of a non-invasive gas $CO_2$ sensor incorporates lactate control to control media feed rate for cell growth and production. Utilizing the invention reduces materials and labor associated with recurring off-line testing. Utilizing the invention allows for continual adjustment of the dilution rate that would otherwise be inefficient and costly if step increases were used as in previous technologies.

Utilizing the present invention increases the predictability of cell culture metabolics and allows a perfusion cell culture unit to have an increased level of automation. The lactate and media dilution rate can be used to determine the state of cell growth and production.

The present invention also utilizes a novel approach for pH sensing in a cell culture unit. Referring back to FIGS. 2, 18 and 19, pH probe 26 and a holder are built into cell culture disposable 12, thus the user is not required to add the probe to the cultureware. Probe 26 is intended to be a one-time use device that is disposed of with the cultureware. The probe is disposed of with the used cultureware, no time is spent recovering the probe for cleaning, revalidating and reuse.

In operation, the probe 26, for example, a solid gel filled electrode, is mounted in a holder 28 (FIG. 23) through which the media to be sensed flow. The electrode in the holder is fluidically connected to the cultureware circuit, mounted in the cultureware module, the circuit is checked for fluidic integrity, and sterilized with the completed cultureware (ethylene oxide, EtO). After sterilization, QC checks are performed on the EtO process to provide high confidence of sterilization. When an operator wishes to culture cells, the cultureware is removed from the pouch, loaded on the instrument and fluid is introduced into the cultureware. A period of time is given to re-hydrate the electrode. The cultureware is brought to operating conditions, the electrode is calibrated and then used to control pH in the cultureware. When the cell culture is complete, the operator disposes of the cultureware and the probe. Although the probe has been described as a solid gel electrode other probe types could be used (e.g., an ISFET, liquid filled, immobilized phenol matrix, fluorescence, etc.).

Figure 23:
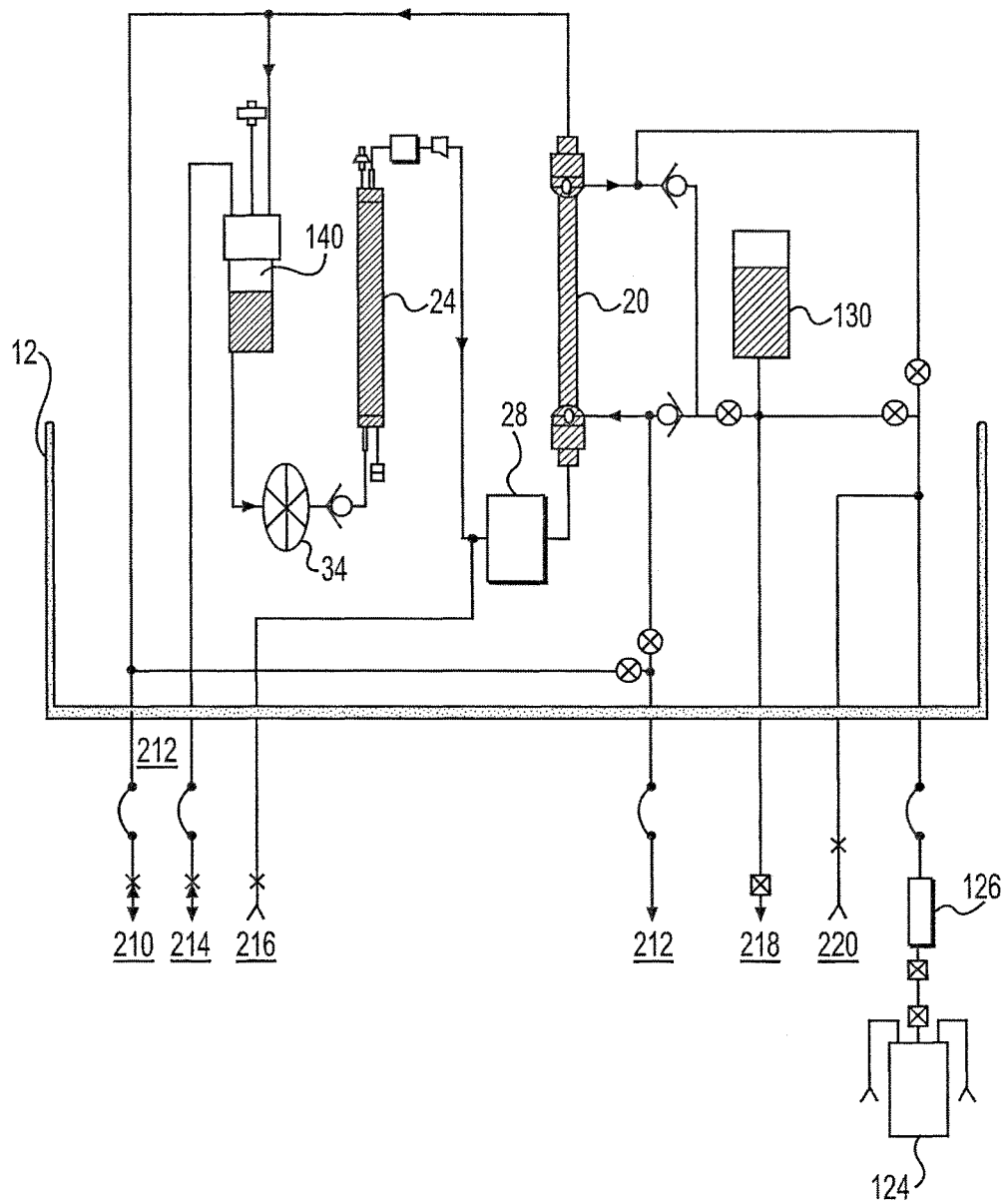
FIG. 23 is a flow diagram of the apparatus of the present invention.

Referring to the flow diagram of FIG. 23, pump 16 moves fresh basal media into the cultureware at media line 210. Media line 210 is connected to a user provided container of fresh media to provide the growth nutrients to the cell culture that are pumped into the disposable. Outflow line 214 is connected to a user provided container to collect the waste or spent media being pumped out of the disposable. Factor line 212 is connected to a user provided container of growth factors that are pumped into the disposable. EC inoculate can be added at 220 and IC sample at 216. Product harvest is removed at 126. The cells are harvested at 218. Harvest line 218 is a pre-attached container that is part of the disposable that is used to collect the product that is pumped out of the disposable. Pump 16 has multiple lines 210, 214, 212 and 126. Because the pump of the present invention has a common fixed axial shaft and individual servo driven rotors, the control of the flow of each can be independent, allowing one channel or flow to be increased while another decreased.

Figure 25:
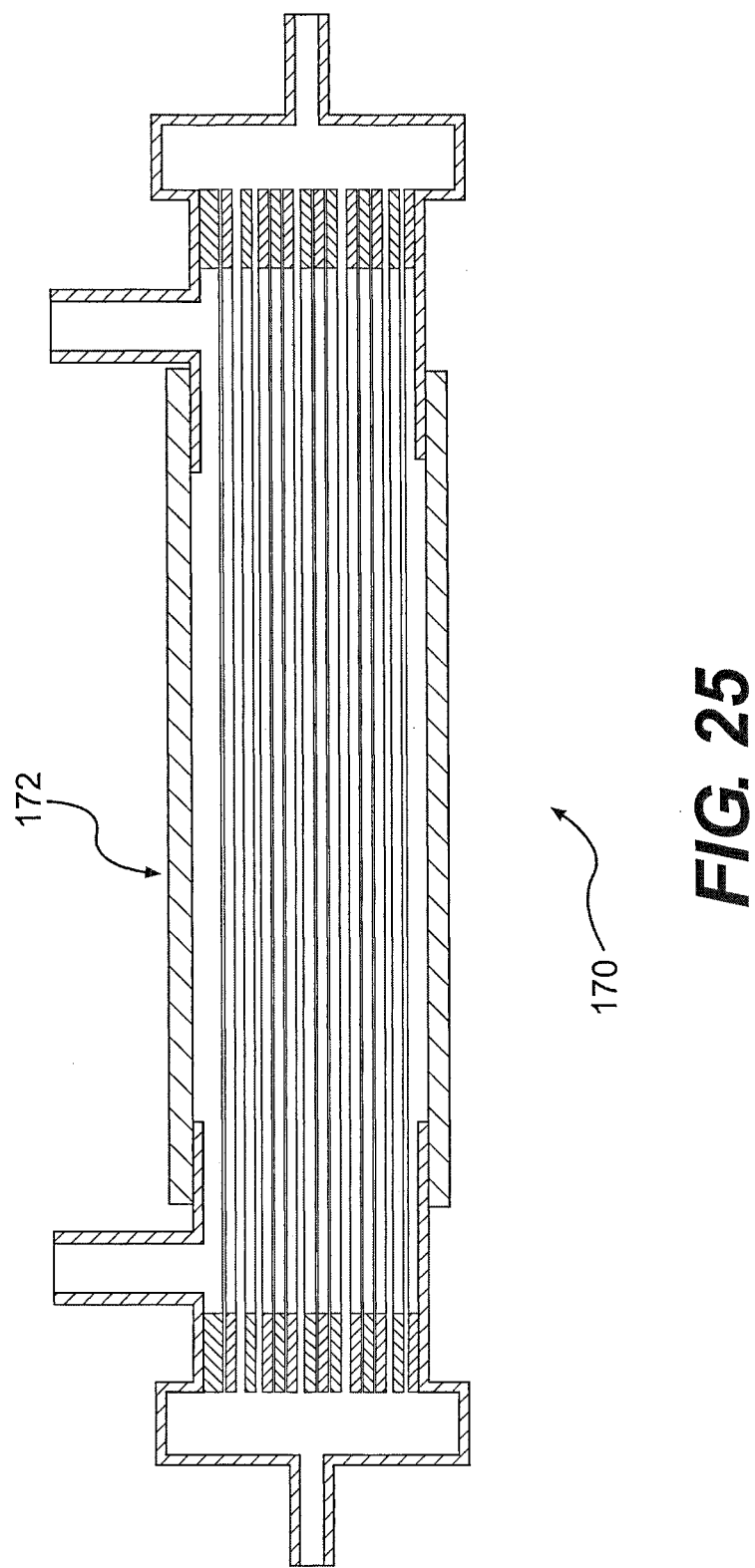
FIG. 25 is a cross-sectional view of a flexible hollow fiber bioreactor according to the present invention.

As shown in FIG. 25, a bioreactor 170 may have a flexible outer body 172 allowing for physical movement of the cell growth substratum (hollow fibers, membrane or other suitable matrix) when a resultant torqueing or bending moment is applied to the bioreactor ends. Flexible outer body 172 allows for the bioreactor case to be flexed causing fiber movement. This fiber movement enhances the release of cells that have attached to the side of the bioreactor matrix. The cells can then be harvested by flushing either after or during the manipulation. This method can provide increased efficiency of cell harvest at high cell viabilities without the use of chemical or enzymatic release additives.

A bioreactor can be constructed using an outer housing that incorporates a flexible center section. This center section is composed of a flexible, non-permeable tubing that allows each end of the bioreactor to be manipulated, thus causing movement of the growth matrix. The purpose of this movement is to release the attachment or clumping of cell products on the extra-capillary (EC) side of the fibers. The cell products can then be flushed from the EC via the access port at each end of the bioreactor.

Harvesting cells from a matrix-containing bioreactor such as a hollow fiber bioreactor has been difficult to accomplish. Typically, cells are sticky and attach themselves to the fibers or to other cells and form clusters. Rapid flushing of media through the EC to hydraulically force the cells free and into the harvest stream is the most basic method of harvesting cells from the EC space. Typically the quantity of cells harvested is low because the flushing media tends to shunt through the EC and flush cells only from the limited fluid path.

Another method is to physically shake or impact the outer housing to release the cells or clumps of cells. This practice may cause physical damage to the bioreactor or its associated components. Another method includes the use of chemicals to disrupt the adhesion of cells to the fibers or to disrupt the clumps of cells. Adding chemicals to a controlled process may cause adverse effects on cell viability and can introduce an unwanted agent in the down-stream processing.

Figure 26:
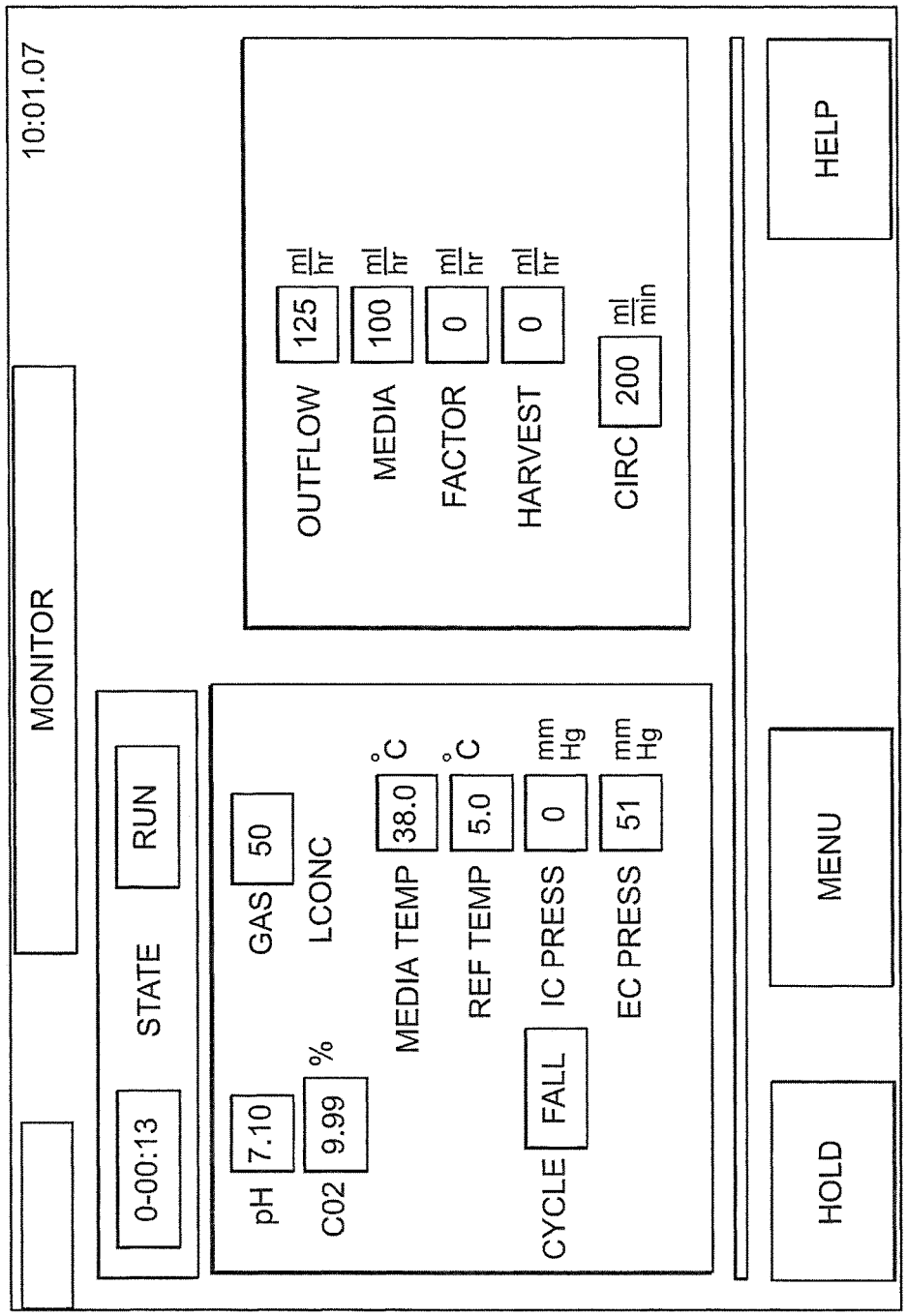
Figure 27:
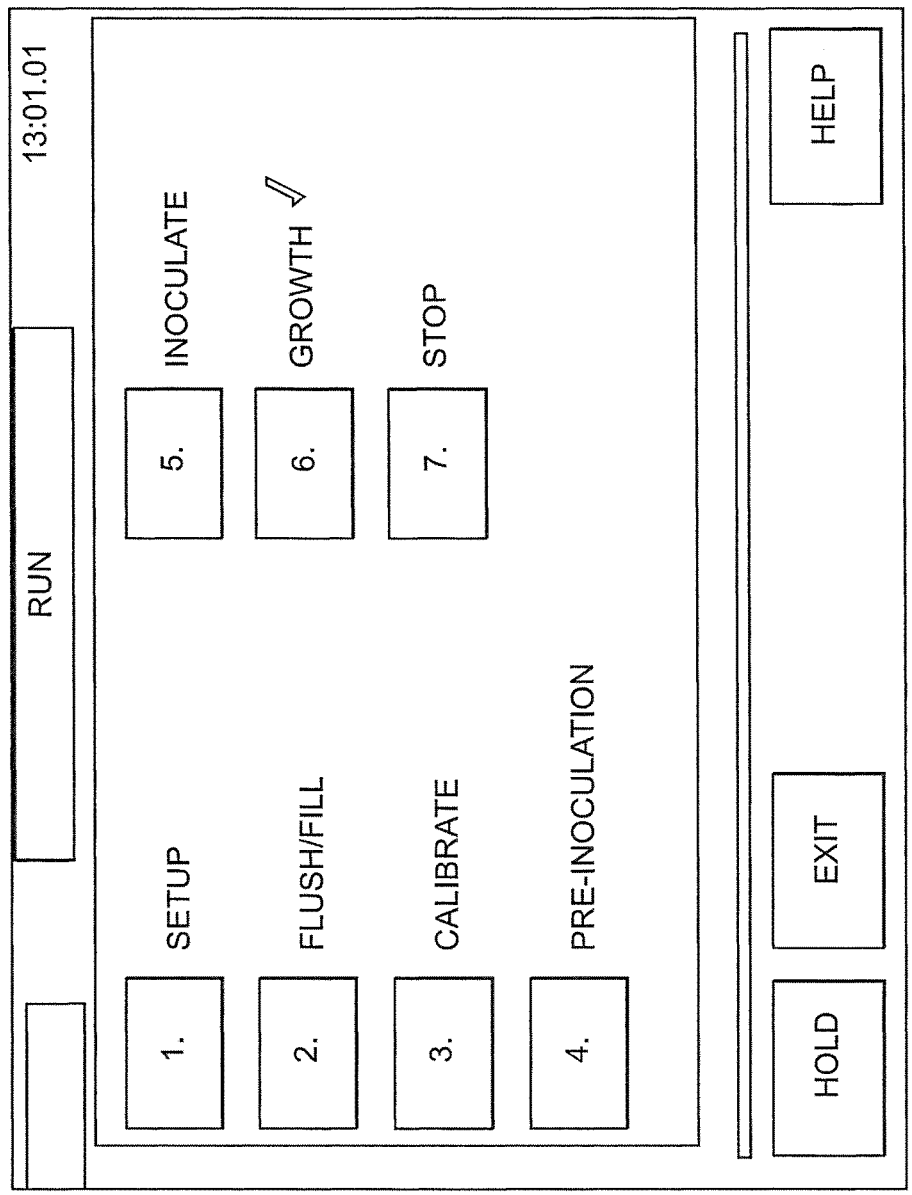
Figure 29:
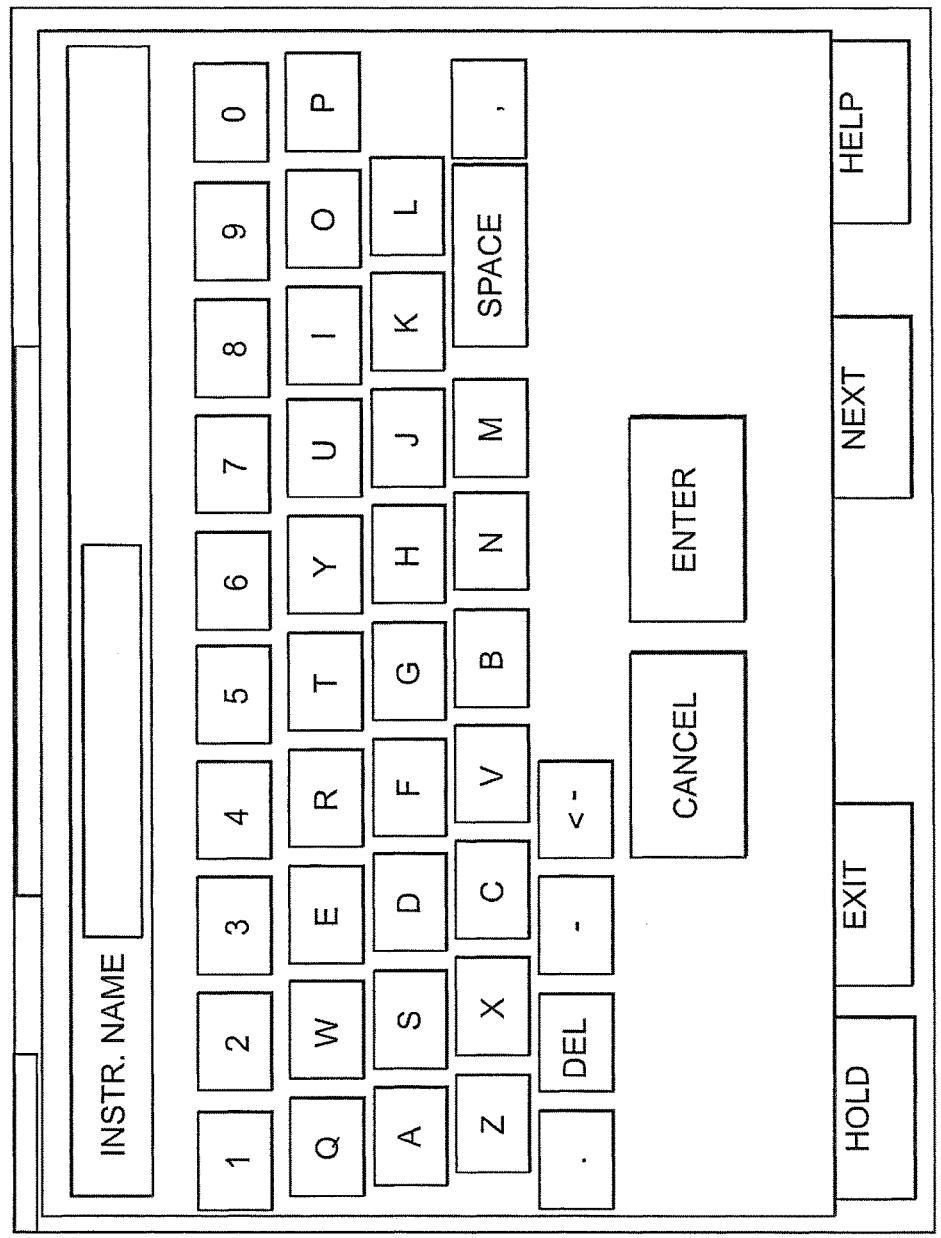
Figure 30:
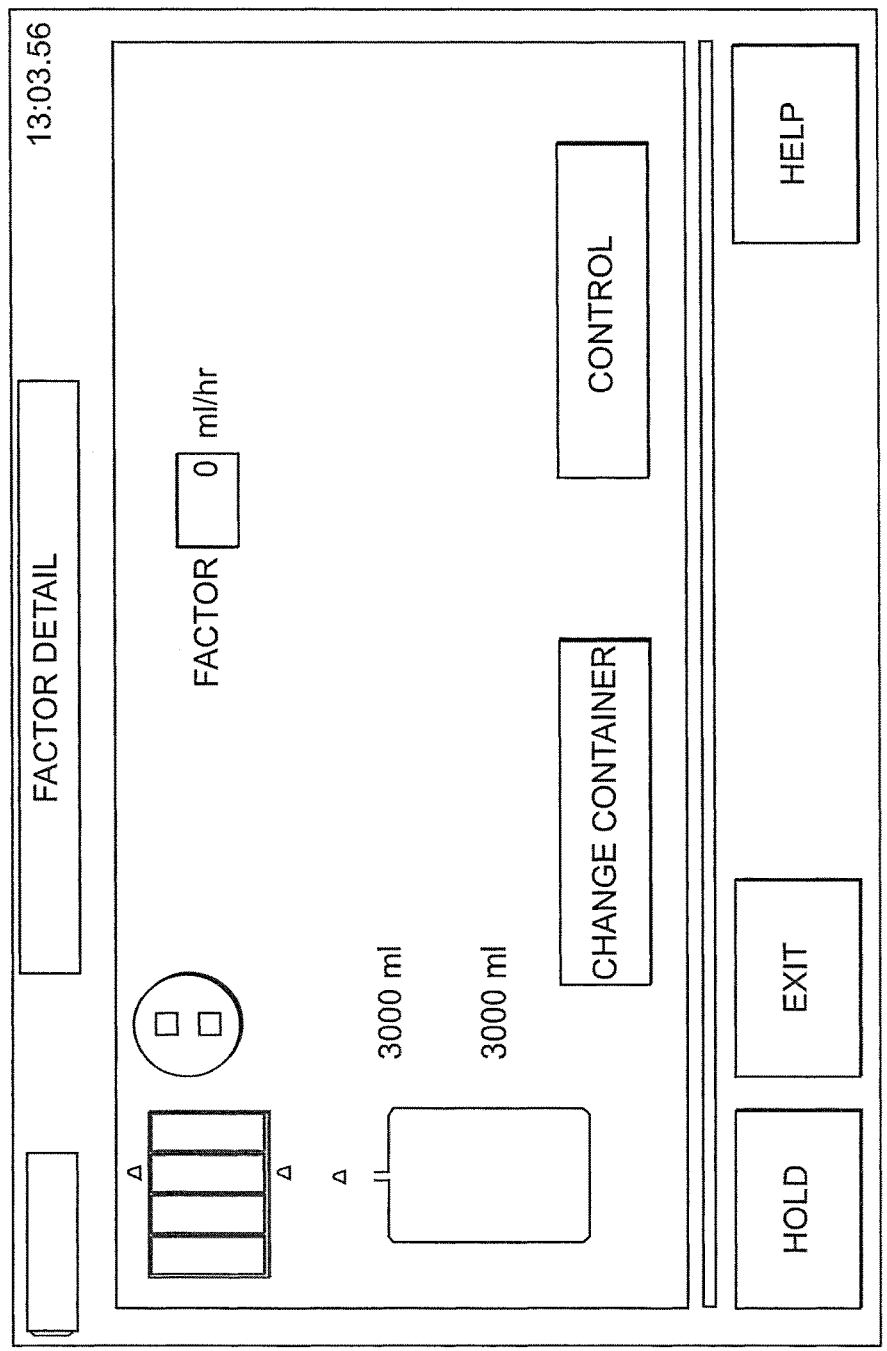
Figure 31:
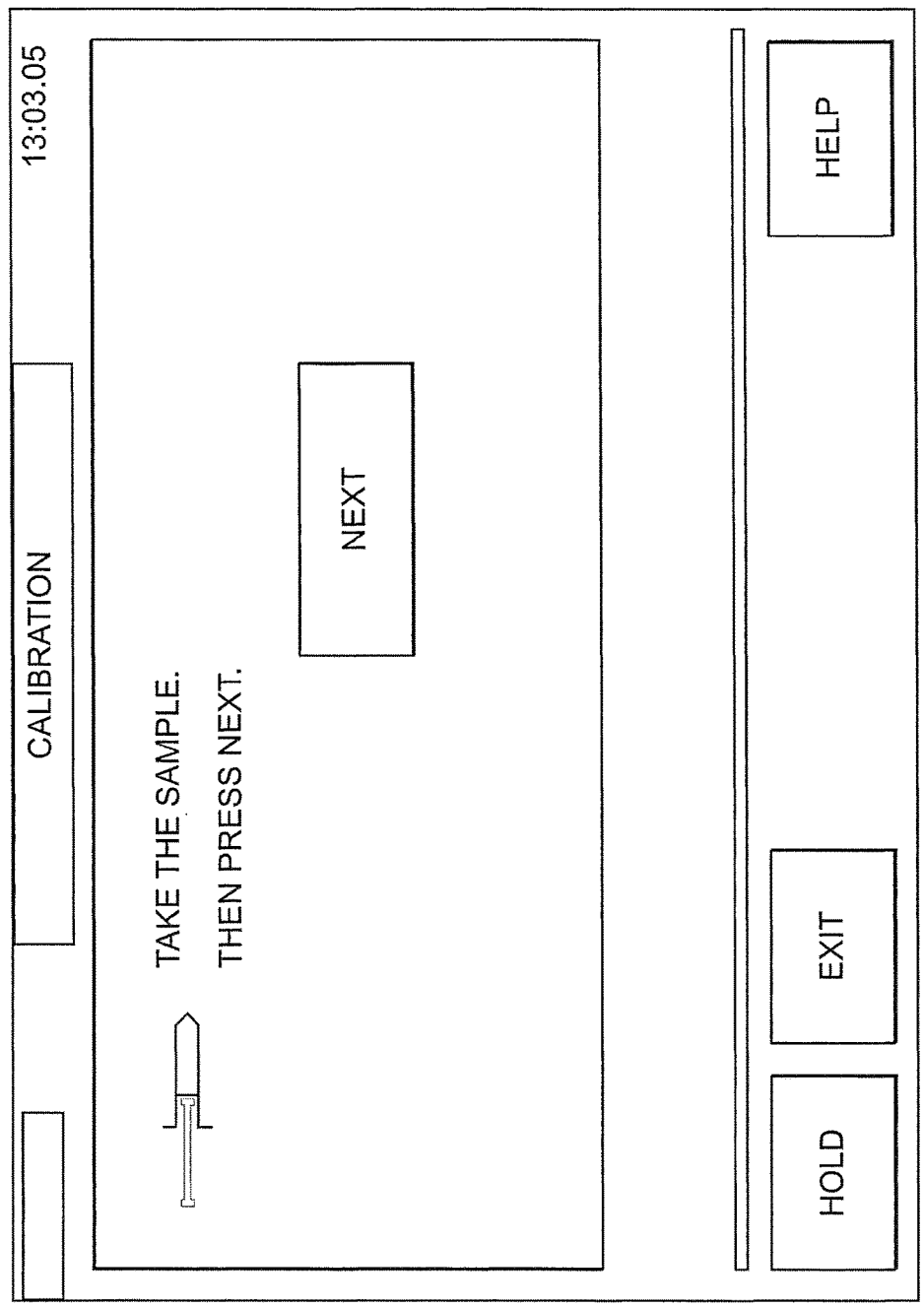

Referring to FIGS. 26-31, various views of the touch display screen illustrate the different interactive steps during control process of the apparatus of the present invention. FIG. 26 shows a system overview screen which highlights current conditions. FIG. 27 illustrates a run sequence screen which directs the operator through the culture process. FIG. 28 illustrates log data which the operator can review and which is available to build the batch record. FIG. 29 shows a method for inputting alpha-numeric data. FIGS. 30 and 31 show operator interaction screens to assist in operations (factor addition and pH probe calibration). On line help screens aid the operator for correct operation.

The apparatus of the present invention fully integrates the concept of disposable cultureware into automated process control for maintaining and expanding specialized (autologous or other) cell lines for a duration of any time needed. To accomplish this, the apparatus of the present invention was designed for EC space fluid flow that enhances cell growth in high density perfusion culture, yet remains completely closed and disposable. The integrated pre-assembled cultureware, which consists of all tubing, bioreactor, oxygenator, pH probe, is enclosed in a single unit that easily snaps into the apparatus. In addition to this error-proof, quick-load design, the entire cultureware unit enclosed by the casing becomes the cell culture incubator with temperature control regulated through automated process control of the instrument. Pumps and fluid control valves facilitate disposability and error-proof installation, eliminating the possibility of technician mistakes. Finally, during the course of any culture, as a closed system, restricted access is facilitated, except for trained and authorized personnel. Manipulations or sampling, outside of program parameters, can require password and identification code (e.g., bar code radio frequency identification (RFID) tag, bokode, or quick response (QR) code) access before they can be implemented.

Purification Unit

The purification unit of the integrated apparatus is an automated apparatus for obtaining a purified biological product such as protein (e.g., a purified antibody), from a biological product-containing aqueous medium (e.g., protein-containing aqueous medium). The purification unit includes two individual parts: a reusable instrumentation base device (also referred to herein as a "second" reusable instrumentation base device, to distinguish it from the reusable instrumentation base device of the cell culture unit), and at least one disposable cell cultureware module that is used for a single production run and is disposable (also referred to herein as a "second" disposable cell cultureware module, to distinguish it from the at least one disposable cultureware of the cell culture unit).

The instrumentation base device of the purification unit provides the hardware to extract the fluid with the cell product from the cell culture unit and process it. An air detector checks the cultureware line which carries the fluid from the cell culture module to determine when fluid is available to run through the column and when no more fluid is available. Drives for a plurality of switching valves (e.g., three switching valves) control the disposable valve portions to route fluids to complete the processes. A peristaltic pump is used to move the fluids to accomplish the process. A cooler could be used to lower the disposable column temperature to minimize product degradation. An optical density detector is used in the process to determine when final product should be collected. The purification unit relies on the cell culture unit for user interface and communications with the facilities data management system. The purification apparatus and method described in International Publication No. WO 2005/090403, "Method and Apparatus for Protein Purification" (Gramer M. et al.), is hereby incorporated by reference in its entirety.

As is the case with the cultureware of the cell culture unit, the cultureware of the purification unit is for one-time use. The selection device (e.g., a purification column) and diafiltration module are loaded into the cultureware just before use. The reservoirs are filled at that time with the correct buffers for the cell product type. That information is tied to the cultureware's identifying code (e.g., bar code, radio frequency identification (RFID) tag, bokode, or quick response (QR) code) in the facilities data management system when the operation is done and is used to verify the proper purification cultureware is loaded for the cell product that is to be purified. A plurality of disposable switch valves (e.g., seven disposable switch valves) are used to prepare the cultureware and route the fluids. Two easy-load peristaltic pump cassettes are provided. A flow cell for measuring optical density is provided on the outlet of the purification column. A removable container holds the finished product (e.g., cell-derived product, such as antibody). The pump cassette and cultureware body is unloaded from the instrumentation base device of the purification unit and placed in a biohazard container for disposal.

The purification unit utilizes pre-sanitized or pre-sterilized disposable cultureware, such as pre-sanitized or pre-sterilized disposable selection device, diafiltration module, liquid reservoirs, valves, tubing, and collection vessels, which can be packaged together for single use and then disposed of. Accordingly, the purification unit (also referred to as an Autovaxid Purification Module) is capable of purifying proteins, such as antibodies, in a highly efficient and contaminant-free manner. Specifically, the automated purification unit minimizes the need for operator intervention and provides a completely disposable flowpath to eliminate the need for cleaning and to eliminate the potential for cross-over contamination. Therefore, the purification unit is an automated apparatus for purifying proteins and other cell products in a less labor intensive manner compared to manual purification methods, thus, reducing purification time and increasing efficiency.

Figure 32:
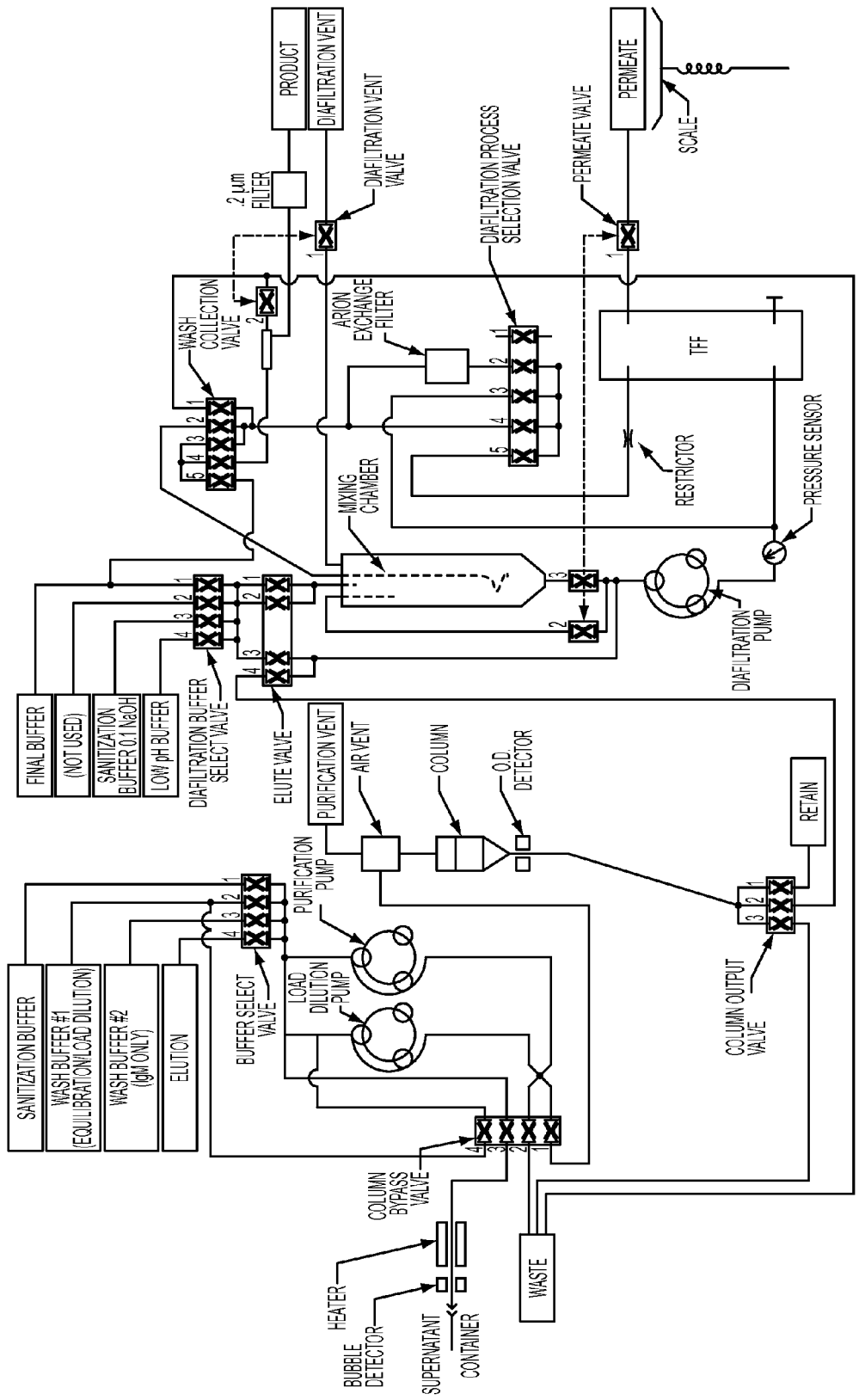
FIG. 32 shows a schematic representation of an embodiment of the purification unit, wherein the selection device, e.g., an affinity column, and the diafiltration module of the purification unit are connected to multiple liquid reservoirs. The reservoirs each contain liquid, such as a wash buffers and an elution buffer for delivery to the selection device and acidic, basic and final buffer solutions for delivery to the diafiltration module. Elution of the purified protein from the selection device can be aided by a photometer. The apparatus further includes a device for flowing liquid from the reservoirs into the selection device or into the diafiltration module, for example, valves and tubing which connect the reservoirs to the selection device or to the diafiltration module. The flow of the liquid is diverted by valves which transfers the eluted protein-containing solution from the selection device to the diafiltration module and then to the pre-sterilized removable collection vessel (also referred to herein as the second cultureware module).

In one embodiment, the purification unit has the configuration shown schematically in FIG. 32. The purification unit comprises a pre-sanitized or pre-sterilized, disposable cultureware module, as discussed above. With reference to FIG. 32, the cultureware module includes, for example, a selection device (e.g., a purification column), a diafiltration module, multiple liquid reservoirs, a device for flowing liquid from the reservoirs and into the selection device and the diafiltration module, a device for diverting the effluent from the selection device and the diafiltration module, e.g., at least two reservoirs. The cultureware module of the purification unit is capable of being installed into the instrumentation base device via a single motion or "snap-on" or "quick-load" technique and comprises mechanical and electrical interfaces for communicating with the instrumentation base device.

In the diafiltration loop (mixing chamber, pump, pressure guage and TFF cartridge), there is a volume of fluid. Because of the physical characteristics of the TFF cartridge, molecules above a certain size are retained in the loop, smaller molecules can flow (permeate) across the fiber and out the permeate port of the TFF device. Pressure on the loop side determines rate of flow across the membrane for a specific membrane. Pressure is generated by flowing fluid through the TFF and/or restricting the outlet tubing of the TFF device returning fluid to the mixing chamber. Because the TFF loop is a closed loop, permeating fluid causes a negative pressure in the head space of the mixing chamber. This provides the hydrostatic pressure needed to draw fluid from the selected buffer bag to make up the volume. Due to the small volume in the loop it is efficient at buffer exchange (it takes less fluid to get to a desired concentration or reduction than dialysis).

Permeate of diafiltration may be monitored by weighing collected permeate fluid. The permeate rate for a given pressure will change over the course of the diafiltration due to membrane fouling. With that in mind, by observing the amount of fluid that has permeated from the loop, an accurate prediction of the loop concentration can be made. Since it is easier to measure weight than volume aseptically and knowing 1 gram of fluid is approximately 1 ml, incorporating a scale system ("scale" in FIG. 32) which captures the permeate is a viable system for controlling the buffer exchange process. As an example, if a buffer exchange is desired that will reduce the current buffer to 2% of the original concentration with a different buffer in a 20 ml loop volume, permeating 100 ml while adding the new buffer would provide the desired result (exchanging 5 loop volumes).

With reference to FIG. 32, the apparatus may include two viral reduction devices: a virus filter and an anion exchange filter. The anion exchange is a host cell product and viral reduction device. For tangential flow (TFF), Millipore Pellicon XL Biomax 50 TFF cartridge may be used to provide buffer exchange. This cartridge contains a 50 $cm^2$ polyethersulfone (PES) membrane, with a molecular weight cut off of 50 kilodaltons (kD). This filter will retain molecules that are larger than 50 kD in size while allowing smaller molecules to pass through. This mechanism allows for control of the concentration of the product by increasing or decreasing the volume of the protein containing solution retained by the filter as well as providing a mechanism for exchanging the buffer components of the protein solution. For anion exchange, a Bio-Rad Bio-Scale Mini Unosphere Q Cartridge (#732-4101) may be used to provide anion exchange chromatography (AEX) capability. Anion exchange exploits differences in charge between the product and impurities. The neutrally charged product passes over the AEX cartridge in flow-through mode, while negatively charged impurities are retained.

For the virus filter, an Asahi Kasei Planova Viral Filter (EXZ-0010) may be used to filter the final product. The virus filter is specifically for removing viruses from solutions containing biological molecules. In this case, virus filtration works on the principle of size exclusion. Planova filters contain a bundle of straw-like hollow fibers. When a protein solution with possible viral contamination is introduced into these hollow fibers, the smaller proteins penetrate the fiber wall and works its way to the outside of the fiber while the larger virus particles are retained. This may be used for IgG production (IgM will not cross the fibers).

In a particular embodiment, the selection device, e.g., an affinity column, and the diafiltration module of the purification unit are connected to multiple liquid reservoirs. The reservoirs each contain liquid, such as a wash buffer, an elution buffer, or a neutralization solution, for delivery to the selection device or the diafiltration module. Accordingly, the purification unit further includes pre-sanitized or pre-sterilized device for flowing liquid from the reservoirs into the selection device, for example, pre-sterilized valves and tubing which connect the reservoirs to the selection device. The valves and tubing may allow liquid from only one reservoir at a time to pass through the selection device. Alternatively, the valves and tubing allow for liquid from more than one reservoir to pass through the selection device.

In a particular embodiment, the purification unit includes a pre-sanitized or pre-sterilized device for diverting the effluent from the selection device into the diafiltration module or into a waste container. Similarly, the purification unit includes a pre-sanitized or pre-sterilized device for diverting the effluent from the diafiltration module into the pre-sterilized collection vessel or into a waste container.

In one embodiment, the purification method of the invention begins with the automated step of loading a protein-containing aqueous medium, e.g., an antibody-containing aqueous medium, onto a pre-sanitized, preferably a pre-sterilized, disposable selection device to absorb the protein onto the selection device. The selection device for use in the present apparatus and method can include, for example, a column packed with an affinity resin, such as an anti-IgM resin, a Protein A, a Protein G, or an anti-IgG resin. In another embodiment, the protein-containing aqueous medium and the selection device can be pre-treated prior to loading. For example, the protein-containing aqueous medium can be automatically heated and degassed before loading. The selection device can be washed, pre-eluted, and/or pre-neutralized prior to loading.

After loading, the selection device is typically washed to remove residual contaminants contained within the aqueous medium, such as residual proteins from host cells used to produce the protein to be purified, e.g., host cell proteins, nucleic acids and endotoxins.

After washing, the bound protein is then eluted into an aqueous medium. The step of eluting can be accomplished, for example, by either changing the pH or the salt concentration of the solution which is loaded onto the selection device. For example, an acidic solution can be added to the selection device to produce a protein-containing acidic eluate. An example of an appropriate acidic solution for eluting includes a solution of approximately 0.05 to 0.5 M of an acid (such as, glycine or citrate) at a pH of about 2 to 5. Alternatively, the step of eluting can include adding a solution to the selection device which alters the salt concentration of the aqueous medium loaded onto the selection device. In one embodiment, the step of eluting the protein is facilitated by the use of a photometer.

Upon eluting the protein into an aqueous medium, the eluted purified protein can be automatically deposited into a pre-sterilized, disposable collection vessel and removed from the automated purification apparatus. Alternatively, the eluted purified protein can undergo further automated processing.

In one embodiment, the eluted purified protein, e.g., an antibody, is transferred to an acidic solution. This transfer to an acidic solution can be accomplished by using, for example, a diafiltration module contained within the automated apparatus. The diafiltration module is a membrane-based ultrafiltration module installed within the automated purification unit which utilizes the tangential flow filtration principle. Accordingly, the eluted protein is diafiltered against an acidic solution (e.g., a solution of approximately 0.1 M glycine at a pH of about 2.0 to 5).

The method of the invention can include the step of placing the eluted protein in contact with the acidic solution for approximately less than 16 hours to inactivate any susceptible virus that may be contained within the solution. For example, the protein is held in the acidic solution for approximately 15.5 hours, 15 hours, 14.5 hours, 14 hours, 13.5 hours, 13 hours, 12.5 hours, 12 hours, 11.5 hours, 11 hours, 10.5 hours, 10 hours, 9.5 hours, 9 hours, 8.5 hours, 8 hours, 7.5 hours, 7 hours, 6.5 hours, 6 hours, 5.5 hours, 5 hours, 4.5 hours, 4, hours, 3.5 hours, 3 hours, 2.5 hours, 2 hours, 1.5 hours, 1 hour or less. In another embodiment, the protein is held in the acidic solution for less than 1 hour, for example for approximately 55 minutes, 50 minutes, 45 minutes, 40 minutes, 35 minutes, 30 minutes, 29 minutes, 28 minutes, 27 minutes, 26 minutes, 25 minutes, 24 minutes, 23 minutes, 22 minutes, 21 minutes, 20 minutes or less, e.g., 19, 18, 17, 16, 15, 14, 13, 12, 11, 10, 9, 8, 7, 6, 5, 4, 3, 2 or 1 minute.

In another embodiment, the protein-containing acidic solution is then neutralized by transferring it to a basic solution, for example, by diafiltering against a basic solution (e.g., a solution of approximately 10 mM citrate at a pH of about 5 to 7).

In another embodiment, the protein-containing basic solution is transferred to a final buffer solution, for example, by diafiltering against a final buffer solution (e.g., a solution of approximately 0.2-0.9% saline (NaCl)).

In another embodiment, the protein-containing final buffer solution can be further purified, for example, by filtering the solution, for example, filtering it through a filter having a pore size of approximately 0.22 μm.

In another embodiment, the method of the invention further includes the step of conjugating the purified protein (e.g., antibody) to an adjuvant, such as Keyhole limpet hemocyanin (KLH). Accordingly, the present invention can be used to produce a variety of vaccines. In a particular embodiment, the invention provides a method for producing an antibody vaccine, particularly an antibody against a tumor cell, such as a B cell for the treatment of lymphoma.

The purification unit is an automated apparatus for purifying a protein or other cell product from a cell product-containing aqueous medium, comprising at least one pre-sanitized or pre-sterilized, disposable cultureware module attached to an automated instrumentation base device for controlling liquid flow through the cultureware module. For example, the pre-sanitized or pre-sterilized, disposable cultureware module includes a selection device; multiple, liquid reservoirs; a device for flowing liquid from the reservoirs and into the selection device; a device for diverting the effluent from the selection device; and a device for collecting effluent from the selection device. The pre-sanitized or pre-sterilized, disposable cultureware module can further include a diafiltration module; a device for flowing liquid from the reservoirs and into the diafiltration module; a device for flowing liquid between the selection device and the diafiltration module; a device for diverting the effluent from the diafiltration module; and a device such as a container for collecting effluent from the diafiltration module, e.g., at least two disposable reservoirs.

In a particular embodiment, the device for flowing liquid (such as, wash buffer, elution buffer, or neutralization solution) into the selection device or diafiltration module includes a series of pre-sanitized or pre-sterilized, disposable valves and tubing which connect the reservoirs to the selection device or diafiltration module and which allow liquid from only one reservoir at a time to pass through the selection device or diafiltration module. Alternatively, the valves and tubing which connect the reservoirs to the selection device and diafiltration module allow liquid from more than one reservoir at a time to pass through the selection device.

In one embodiment, the valve includes a disposable outer body through which flexible tubing is threaded. A cammed shaft is mated with the body and a motor drives the shaft to open and close the tubing. Multiple tubing lines can be controlled by one motor/shaft. The pre-sanitized or pre-sterilized tubing lines contain the fluid and maintain sterility. The tubing and outer body housing are disposed of at the end of use.

In another embodiment, the purification unit includes a device for monitoring the effluent from the selection device or diafiltration module, such as a probe or sensor for measuring the pH, absorbance at a particular wavelength, or conductivity of the effluent. One or more pressure sensors may be included for monitoring fluid pressure for excessive pressures, or for control of peristaltic pump speed, e.g., to maintain the pump speed at a desired pressure (a feedback mechanism). In some embodiments, the pressure sensor is placed in the purification flow path, on the output of the pumps.

The pre-sanitized or pre-sterilized, disposable selection device is chosen according to the particular type of purification method used, such as immuno-affinity chromatography, affinity chromatography, ionic exchange chromatography (e.g., anion or cation), hydrophobic interaction chromatography, or size exclusion chromatography (SEC). Suitable selection devices for these types of purification processes are well known in the art including, for example, an affinity column packed with an anti-IgM resin, a Protein A, a Protein G, or an anti-IgG resin, an ion exchange column containing a charged particle (matrix) which binds reversibly to particular proteins (e.g., a Vydac VHP-Series Protein Ion-Exchange column with a polystyrene-divinylbenzene copolymer bead and a chemically attached hydrophilic surface), a column packed with a hydrophobic absorbent, such as cellulose, cross-linked dextrose (Sephadex), or a column containing cross-linked polystyrene with pores of varying sizes. The selection device can include a combination of purification columns. For example, an affinity chromatography column can be used, followed by an SEC column to remove any unwanted aggregate. Furthermore, ion exchange chromatography can be used as a "polishing step" to capture and remove contaminants following affinity chromatography.

In those embodiments in which the selection device is a chromatography device, any chromatrography media having surface chemistries capable of capturing the cell product may be used. Traditional chromatography methods use columns packed with porous particles, which may be used in the invention; however, the architecture of the chromatography is not critical. For example, the chromatography media may be a membrane, monolith, or porous particles.

In some embodiments, the selection device is a chromatography column or filter having a natural or synthetic hydroxyapatite matrix (e.g., ceramic hydroxyapatite). Hydroxyapatite is a naturally occurring mineral form of calcium apatite. Hydroxyapatite is the hydroxyl end member of the complex apatite group. The OH— ion can be replaced by fluoride, chloride or carbonate. It crystallizes in the hexagonal crystal system. Hydroxyapatite can be used in chromatography for purification. The mechanism of hydroxyapatite chromatography is somewhat complicated and has been described as "mixed-mode" ion exchange. It involves nonspecific interactions between positively charged calcium ions and negatively charged phosphate ions on the stationary phase hydroxyapatite resin with protein negatively charged carboxyl groups and positively charged amino groups. For elution, a buffer with increasing phosphate concentration is typically used. Hydroxyapatite that can be used to pack columns and filters for chromatography includes natural hydroxyapatite and synthetic hydroxyapatite (e.g., crystalline hydroxyapatite, ceramic hydroxyapatite). Thus, in some embodiments of the purification method of the present invention, solution containing desired immunoglobulin or other cell product can be purified by a hydroxyapatite column or filter, wherein the hydroxyapatite column or filter is packed with natural hydroxyapatite or synthetic hydroxyapatite. In some embodiments, the synthetic hydroxyapatite is crystalline hydroxyapatite or ceramic hydroxyapatite.

In a particular embodiment, the selection device comprises a pre-sterilized affinity purification column, e.g., a column approximately 1.5 to 2.5×10 cm in length which is pre-packed with approximately 4 to 10 ml of resin, such as an affinity ligand (binding substance), such as Protein A, Protein A analogs, Protein G, anti-IgG or anti-IgM resin. Affinity chromatography (AC) is a technique enabling purification of a biomolecule with respect to biological function or individual chemical structure. The substance to be purified is specifically and reversibly adsorbed to a ligand which is immobilized by a covalent bond to a chromatographic bed material (matrix). Samples are applied under favorable conditions for their specific binding to the ligand. Substances of interest are consequently bound to the ligand while unbound substances are washed away. Recovery of molecules of interest can be achieved by changing experimental conditions to favor desorption.

The ligand, Protein A, is a group specific ligand which binds to the Fc region of most IgG. It is synthesized by some strains of *staphylococcus aureus* and can be isolated from culture supernatants then insolubilised by coupling to agarose beads or silica. An alternative method is to use whole bacteria of a strain which carries large amounts of Protein A on the bacterial cell surface. Both types of gel preparation are available commercially (Pharmacia; Calbiochem). Alternatively, a recombinant form of Protein-A can be used (ProSep-rA, Millipore).

An alternative to Protein A is Protein G (Anal. Chem. (1989) 61(13):1317). Protein G is a cell surface-associated protein from *streptococcus* that binds to IgG with high affinity. It has three highly homologous IgG-binding domains.

Anti-IgM antibody can also be used as part of the selection device of the present invention to purify antibodies. In a particular embodiment, the anti-IgM antibody includes a mouse anti-human IgM monoclonal antibody attached to sepharose by cyanogen bromide (CNBr).

In one embodiment, the ligand, e.g., the affinity resin, is immobilized on a solid phase. The solid phase may be a purification column or a discontinuous phase of discrete particles. In a particular embodiment, the solid phase is a controlled pore glass column or a silicic acid column. Optionally, the solid phase is coated with a reagent (such as glycerol) which prevents nonspecific adherence of contaminants to the solid phase.

Proteins which can be purified by the present invention include various forms of proteins, such as tumor antigens and antibodies. An epitope of the tumor antigen can be any site on the antigen that is reactive with an antibody or T cell receptor. Other examples of tumor antigens include, but are not limited to human epithelial cell mucin (Muc-1; a 20 amino acid core repeat for Muc-1 glycoprotein, present on breast cancer cells and pancreatic cancer cells), the Ha-ras oncogene product, p53, carcino-embryonic antigen (CEA), the raf oncogene product, GD2, GD3, GM2, TF, sTn, MAGE-1, MAGE-3, tyrosinase, gp75, Melan-A/Mart-1, gp100, HER2/neu, EBV-LMP 1 & 2, HPV-F4, 6, 7, prostatic serum antigen (PSA), alpha-fetoprotein (AFP), CO17-1A, GA733, gp72, p53, the ras oncogene product, HPV E7 and melanoma gangliosides, as well as any other tumor antigens now known or identified in the future. In some embodiments, the tumor antigen is the idiotype of a B-cell derived lymphoma (e.g., IgM or IgG isotype).

Various antibody isotypes are also encompassed by the invention, including IgG, IgM, IgA, IgD, and IgE. The antibodies of this invention can be isolated from a number of sources, including without limitation, serum of immunized animals, ascites fluid, hybridoma or myeloma supernatants, conditioned media derived from culturing a recombinant cell line that expresses the immunoglobulin molecule and from all cell extracts of immunoglobulin producing cells.

A purified protein, e.g., antibody, of the present invention is substantially free from host cell contaminants such as host cell proteins, nucleic acids and endotoxins.

In a particular embodiment of the invention, the automated method involves purifying a protein using the steps outlined in Example 1 and the purification unit as represented schematically in FIG. 32. Specifically, prior to loading the protein-containing aqueous medium, the selection device, e.g., an affinity column of approximately 1.5 to 2.5.×10 cm in length packed with approximately 4 to 10 ml of resin, is washed. The selection device can be washed with liquid stored in the liquid reservoirs which are connected to the selection device with pre-sanitized valves and tubing. For example, the selection device can be washed with phosphate buffer saline (PBS) or a neutral buffer at a pH of about 7.2 to remove impurities, such as preservatives found in the pre-packed, pre-sterilized, disposable column. The size of the column may vary based on the type of protein being purified. For example, methods for purifying IgM antibodies use a column about 2.5 cm in diameter, while methods for purifying IgG antibodies use a column about 1.5 cm in diameter.

Optionally, if the cell product to be purified is a membrane-associated protein, such as a membrane-bound receptor, the method can further comprise freeing the membrane-associated cell product from the membrane material using, for example, proteolytic enzymes, prior to loading the culture medium containing the cell products onto the selection device.

In addition, before loading, the column can be pre-eluted with an elution buffer stored in the liquid reservoirs, such as a buffer at a low pH of about 2.4 to 3.0. The column can then be equilibrated to neutralize or increase the pH using, e.g., PBS, and is ready for loading.

The protein-containing aqueous medium or supernatant is then loaded onto the pre-sterilized, disposable selection device. This can be done after adjusting the supernatant or, more preferably, is done without adjusting the supernatant. The appropriate rate for loading can be determined as is known in the art and generally involves loading at a rate of at least 0.5 to 2.5 ml/min, preferably about 5.0 ml/min.

In a particular embodiment, the medium is heated and/or degassed prior to loading to reduce or eliminate the amount of dissolved gas which can accumulate in the separation device and hinder its ability to bind cell product (e.g., protein). For example, the protein-containing aqueous medium is heated to about room temperature and degassed.

Once loaded, the selection device can be washed with a wash solution that is stored in a liquid reservoir to remove any residual contaminants contained in the aqueous medium, such as residual proteins from the host cells which were used to produce the protein to be purified, e.g., contaminants such as host cell proteins, nucleic acids and endotoxins. The appropriate volume and solution for removing contaminants can be determined as is known in the art. In a particular embodiment, the column is washed using a buffer, such as PBS, until the ultraviolet (UV) absorbance of the effluent is about zero as measured using standard photometric procedures.

The protein is then eluted, for example, by using an acidic solution, thereby producing a protein-containing acidic eluate. In another embodiment, the salt concentration of the loaded column is changed. To elute by changing the pH of the loaded column, an acidic elution buffer can be added, such as an elution buffer containing approximately 0.05 to 0.5 M of an acid and at a pH of about 2.0 to 5.0. The appropriate volume and rate of the elution buffer can be determined by one of ordinary skill in the art. In a particular embodiment, the elution buffer is added to the column at approximately 1.0 to 2.0 ml/min for a total of about four (4) column volumes. Further, the type of elution buffer depends on the type of protein to be purified and can also be determined based on the techniques known in the art. For example, for purification of an IgM antibody, the elution buffer may comprise approximately 0.1 M glycine at about pH 2.4. For purification of an IgG antibody, the elution buffer may comprise approximately 0.1 M citrate at approximately pH 3.0. Those of ordinary skill in the art can determine the optimum molarity and pH based on the ranges and teachings provided herein.

In a particular embodiment, the elution of the purified protein from the selection device can be aided by a monitoring device. For example, the absorbance at a particular wavelength of the eluate can be monitored using a photometer to determine the appropriate concentration of the eluate. Methods for eluting proteins by using a photometer are well known in the art. Generally, collection of the peaks containing the purified protein begins when the ultraviolet (UV) absorbance of the eluate begins to increase from baseline (zero). Collection continues until the UV absorbance returns to its baseline. In a particular embodiment, the volume of the peak fractions collected is about 10 to 25 ml and the peaks are collected in a pre-sanitized or pre-sterilized, reservoir contained within the purification apparatus.

The purification unit and method of the invention can further include a viral clearance step to remove virus from the culture medium containing the cell product (e.g., by filtration).

Following elution, the purified biological product (e.g., protein such as antibody) can be collected in a pre-sterilized, disposable collection vessel and removed from the purification unit. In another embodiment, the eluted biological product (e.g., antibody) can undergo further processing by the automated purification unit. For example, the eluted biological product can be transferred to an acidic solution, e.g., an acidic solution containing approximately 0.1 M glycine at a pH of approximately 2.4, to ensure that the previous buffer that the biological product was solubilized in has been replaced by the acidic solution. Enough volume is used so that the buffer exchange efficiency is theoretically greater than or equal to about 99.5%. Once in the acidic solution (e.g., 0.1 M glycine at pH 2.4), the protein-containing solution is treated (held) for less than approximately 16 hours at these conditions in order to inactivate any susceptible virus that may be present. However, holding the protein-containing solution for longer than 16 hours may result in degradation of the protein. Protein degradation is caused directly by the low pH which unfolds the protein irreversibly or by proteases which are more active at low pH. Degradation of proteins can be measured by using assays which characterize the structure of the proteins, such as gel electrophoresis and high performance liquid chromatography (HPLC). Degradation of proteins can also be measured by protein activity, such as potency, toxicity, or content, in a biological assay, such as in vitro cell receptor binding assays or in vitro antigen content assays. Accordingly, in one embodiment, the protein is held in the acidic solution for approximately 15.5 hours, 15 hours, 14.5 hours, 14 hours, 13.5 hours, 13 hours, 12.5 hours, 12 hours, 11.5 hours, 11 hours, 10.5 hours, 10 hours, 9.5 hours, 9 hours, 8.5 hours, 8 hours, 7.5 hours, 7 hours, 6.5 hours, 6 hours, 5.5 hours, 5 hours, 4.5 hours, 4, hours, 3.5 hours, 3 hours, 2.5 hours, 2 hours, 1.5 hours, 1 hour or less. In another embodiment, the protein is held in the acidic solution for less than 1 hour, for example for approximately 55 minutes, 50 minutes, 45 minutes, 40 minutes, 35 minutes, 30 minutes, 29 minutes, 28 minutes, 27 minutes, 26 minutes, 25 minutes, 24 minutes, 23 minutes, 22 minutes, 21 minutes, 20 minutes or less, e.g., 19, 18, 17, 16, 15, 14, 13, 12, 11, 10, 9, 8, 7, 6, 5, 4, 3, 2 or 1 minute.

The protein-containing acidic solution can further be neutralized by transferring it to a neutral or basic solution to neutralize the effects of the previous low pH treatment, for example, a solution containing approximately 10 mM citrate at a pH of about 5.3. During this step, a continual and gradual rise in pH occurs over the course of less than approximately 16 hours, e.g., approximately 30 minutes. In a particular embodiment, neutralization is completed within about 29-30 minutes, preferably within about 28-29 minutes, and more preferably within about 25-28 minutes of transferring the protein from the acidic solution.

In another embodiment, the purified biological product (e.g., protein, such as antibody) is transferred into an appropriate buffer, such as a saline buffer having approximately 0.2-0.9% saline (NaCl). In a particular embodiment, enough volume is used so that the buffer exchange efficiency is theoretically greater than or equal to about 99.5%.

In an additional embodiment, the biological product (e.g., protein, such as antibody) contained in the final buffer solution is filtered through a filter, for example, a filter having a pore size of approximately 0.22 µm. The purified protein is automatically deposited into a pre-sterilized collection vessel and removed from the automated purification apparatus. In a particular embodiment, the purified biological product (e.g., protein, such as antibody) is stored in a solution containing approximately 0.2-0.9% saline or further processed.

In another embodiment, the step of transferring the eluted antibody to different solutions occurs automatically using a pre-sterilized diafiltration module. Diafiltration is the fractionation process that washes smaller molecules through a membrane and keeps molecules of interest in the retentate. Diafiltration can be used to remove salts or exchange buffers. In discontinuous diafiltration, the solution is concentrated, and the lost volume is replaced by new buffer. Concentrating a sample to half its volume and adding new buffer four times can remove over 96% of the salt. In continuous diafiltration, the sample volume is maintained by the inflow of new buffer while the salt and old buffer are removed. Greater than 99% of the salt can be removed by adding up to seven volumes of new buffer during continuous diafiltration. In a particular embodiment, the diafiltration module contains a filtration membrane of approximately 50 $cm^2$ areas having a normal molecular weight limit or cutoff of 50,000 daltons. Specifically, the diafiltration module is used to further purify the protein (e.g., the antibody) and uses the tangential flow filtration principle whereby molecules over 50,000 daltons (e.g., the antibodies, such as IgG and IgM) cannot pass through the membrane but small molecules, such as buffers, can pass through. Accordingly, the diafiltration module can be used to exchange one buffer for another and is a more efficient substitute for dialysis. Diafiltration can be used to neutralize pH and as a concentration step (to concentrate the cell product).

In a particular embodiment, the diafiltration module is sanitized using a solution containing approximately 0.1 N Sodium Hydroxide at a crossflow or feed rate of approximately 20-40 mL/min. This crossflow rate is maintained throughout the process. The 0.1 N Sodium Hydroxide is flushed out of the system using a solution containing approximately 0.1 M Glycine at a pH of about 2.4. After sanitization is complete, the protein-containing solution which was eluted from the selection device is introduced into the diafiltration module.

In a particular embodiment, the present invention provides an automated method of producing a vaccine by purifying a protein and conjugating the protein to an adjuvant. More particularly, the invention provides a method for producing an autologous vaccine, i.e., a vaccine, such as an antibody vaccine, against a self-protein or idiotype (ID) antigen, such as a tumor antigen. In a particular embodiment, the antigen is a B cell antigen, such as an antibody expressed on B cell tumors (e.g., lymphomas). Accordingly, the vaccine is used to target one specific molecule which is expressed by B-cell lymphoma cells. Moreover, since each vaccine produced is patient-specific, the one time, disposable use of the cultureware used in the invention is particularly advantageous.

Examples of adjuvants include, for example, keyhole limpet hemocyanin (KLH), bovine serum albumin, (BSA), and $\beta_2$-glycoprotein I. Other albumins such as ovalbumin, mouse serum albumin or rabbit serum albumin can also be used as adjuvants, as well as bovine gamma globulin or diphtheria toxoid.

KLH is a respiratory protein found in mollusks. Its large size (M.W. $8-9 \times 10^6$ Da) makes it very immunogenic and the large number of lysine residues available for conjugation make it very useful as a carrier for haptens. The phylogenic separation between mammals and mollusks increases the immunogenicity and reduces the risk of cross-reactivity between antibodies against the KLH carrier and naturally occurring proteins in mammalian samples. KLH is obtainable both in its native form, for conjugation via amines, and succinylated, for conjugation via carboxyl groups. Succinylated KLH may be conjugated to a hapten containing amine groups (such as a peptide) via cross-linking with carbodiimide between the newly introduced carboxyl groups of KLH and the amine groups of the hapten. Protocols for conjugating haptens to carrier proteins may be found in *Antibodies: A Laboratory Manual*, E. Harlow and D. Lane, ed., Cold Spring Harbor Laboratory (Cold Spring Harbor, N.Y., 1988) pp. 78-87.

Accordingly, in one embodiment, the invention provides an automated method of producing a vaccine by purifying an antibody and conjugating the antibody to KLH. Methods for conjugating proteins (e.g., antibodies) to adjuvants (e.g., KLH) are known in the art. In general, conjugation is achieved by mixing the purified protein and the adjuvant with an appropriate catalyst under the appropriate conditions. In a particular embodiment, it may be necessary to take a sample of the purified protein (e.g., antibody) for off-line determination of the antibody concentration before the adjuvant (e.g., KLH) is added. In another particular embodiment, gluteraldehyde is added to begin the conjugation. Since gluteraldehyde is unstable, it may be added manually and can be added in concentrated form or a more dilute form. Adding gluteraldehyde in dilute form may require a diafiltration or dialysis step. After several hours, the conjugation is quenched. In a particular embodiment, the conjugation is quenched by adding glycine. The conjugated protein (e.g., antibody) can be purified further using techniques known in the art, such as dialysis. In a particular embodiment, the conjugated protein is dialyzed using saline for injection (SFI) and the product is recovered.

The purification method and apparatus of the present invention can be used in conjunction to provide a fully automated method for purifying proteins.

Conventionally, each unique cell line must be cultured, cell secretions harvested and purified separately. In order to manage a large number of unique cell lines, as for example might be required for the production of large numbers of autologous cell therapeutic products or large numbers of unique monoclonal antibodies, a considerable number of instruments would be needed. Compactness of the design and the amount of ancillary support resources needed become an important facilities issue. Small stirred tank systems require a device of steam generation and distribution (for steam-in-place sterilization) or autoclaves to sterilize the vessels and supporting plumbing. To support a large number of units becomes a logistics problem for the facility. The apparatus of the present invention has no such requirement. Larger scale cell culture is historically done in segregated steps that often require separate types of equipment. Manual handling, storage and tracking is needed for all these steps as the culture expands and product is harvested. The method of the present invention integrates these steps into a continuous, fully integrated sequential process. This eliminates the handling risk and facilitates the data gathering required for thorough documentation of the entire process.

EXEMPLIFIED EMBODIMENTS

Embodiment 1

An automated cell culture and purification apparatus for the production of cells and cell derived products, comprising:
(a) a cell culture unit comprising:
   a first reusable instrumentation base device incorporating hardware to support cell culture growth; and
   at least one first disposable cell cultureware module removably attachable to said first instrumentation base device, said first cultureware module including a cell growth chamber; and
(b) a purification unit linked to said cell culture unit, said purification unit comprising:
   a second reusable instrumentation base device incorporating hardware to receive fluid from said cell growth chamber of said cell culture unit; and
   at least one second disposable cell cultureware module removably attachable to said second instrumentation base device of said purification unit, said second cultureware module including a selection device (such as a purification column).

Embodiment 2

The cell culture and purification apparatus of embodiment 1, wherein said first instrumentation device of said cell culture unit includes a pump for circulating cell culture medium through the at least one cultureware module.

Embodiment 3

The cell culture and purification apparatus of embodiment 2, wherein the pump of said cell culture unit moves growth factor or other supplements into the cell growth chamber and removes product harvest from the cell growth chamber.

Embodiment 4

The cell culture and purification apparatus of embodiment 2, wherein said first instrumentation device of said cell culture unit includes a plurality of rotary selection valves to control the medium flow through the at least one first cultureware module of said cell culture unit.

Embodiment 5

The cell culture and purification apparatus of embodiment 1, wherein said first instrumentation device of said cell culture unit includes a cool storage area for storing growth factor or other supplements and product harvest.

Embodiment 6

The cell culture and purification apparatus of embodiment 1, wherein said first instrumentation device of said cell culture unit includes a heating mechanism for heating the cell growth chamber to promote growth and production.

Embodiment 7

The cell culture and purification apparatus of embodiment 6, wherein said at least one first cultureware module of said cell culture unit includes an inlet and outlet port, said inlet and outlet ports being constructed and arranged to align with air ports of said instrument device of said cell culture unit such that the heat exchange mechanism forces heated air into said at least one first cultureware module from said first instrument device of said cell culture unit.

Embodiment 8

The cell culture and purification apparatus of embodiment 2, further comprising a pump cassette having attached tubing, the pump cassette and tubing being insertable into the multi-channel pump.

Embodiment 9

The cell culture and purification apparatus of embodiment 2, wherein said at least one first cultureware module includes a gas blending mechanism in communication with the cell growth chamber.

Embodiment 10

The cell culture and purification apparatus of embodiment 9, further comprising a pH sensor disposed in said at least one first cultureware module to control the pH of the cell culture medium.

Embodiment 11

The cell culture and purification apparatus of embodiment 10, wherein the gas blending mechanism includes a gas exchange cartridge that provides oxygen and adds or removes carbon dioxide to the medium to support cell metabolism.

Embodiment 12

The cell culture and purification apparatus of embodiment 11, wherein the gas exchange cartridge has an inlet end and a discharge end.

Embodiment 13

The cell culture and purification apparatus of embodiment 12, further comprising a carbon dioxide sensor in fluid communication with the discharge end of the gas exchange cartridge for measuring the carbon dioxide level of the cell culture medium.

Embodiment 14

The cell culture and purification apparatus of embodiment 1, wherein said at least one first cultureware module of said cell culture unit is pre-sterilized, and wherein said at least one second cultureware module of said purification unit is pre-sterilized.

Embodiment 15

The cell culture and purification apparatus of embodiment 1, wherein said at least one first cultureware module of said cell culture module includes a plurality of interface features integrated into said first cultureware module that mate with instrument interface features in said first instrumentation device.

Embodiment 16

The cell culture and purification apparatus of embodiment 2, wherein said at least one first cultureware module of said cell culture unit includes sensors for sensing fluid circulation rate, temperature and pH of the cell culture medium.

Embodiment 17

The cell culture and purification apparatus of embodiment 1, wherein the cell growth chamber comprises a bioreactor that provides cell space and medium component exchange.

Embodiment 18

The cell culture and purification apparatus of embodiment 1, wherein the selection device is selected from the group consisting of affinity chromatography, immuno-affinity chromatography, ionic exchange chromatography, hydrophobic interaction chromatography, and size selection chromatography (SEC), or a combination of two or more of the foregoing chromatography devices.

Embodiment 19

The cell culture and purification apparatus of embodiment 1, wherein said at least one first cultureware module includes a fluid cycling unit disposed therein to cycle and maintain fluid volumes within the cell growth chamber.

Embodiment 20

The cell culture and purification apparatus of embodiment 19, wherein the fluid cycling unit includes a non-rigid reservoir and a second flexible reservoir in fluid communication with the first reservoir to cause elevated pressure in the first reservoir.

Embodiment 21

The cell culture and purification apparatus of embodiment 1, further comprising a plurality of disposable containers for harvest collection and flushing removably connected to said at least one first cultureware module.

Embodiment 22

The cell culture and purification apparatus of embodiment 1, wherein said selection device comprises an affinity resin.

Embodiment 23

The cell culture and purification apparatus of embodiment 22, wherein said affinity resin is selected from the group consisting of anti-IgM resin, Protein A, Protein G, and anti-IgG resin.

Embodiment 24

The cell culture and purification apparatus of embodiment 1, wherein said selection device comprises a chromatography device comprising hydroxyapatite resin.

Embodiment 25

The cell culture and purification apparatus of embodiment 1, wherein said second disposable cultureware module further comprises: multiple, liquid reservoirs, device for flowing liquid from the reservoirs and into the selection device, device for diverting the effluent form the selection device, and device for collecting effluent from the selection device.

Embodiment 26

The cell culture and purification apparatus of embodiment 25, wherein the device for flowing liquid into the selection device comprises a series of pre-sterilized, disposable valves and tubing which connect the reservoirs to the selection device and which allow liquid from only one reservoir at a time to pass through the selection device.

Embodiment 27

The cell culture and purification apparatus of embodiment 25 or 26, wherein the device for flowing liquid into the selection device comprises a series of pre-sterilized, disposable valves and tubing which connect the reservoirs to the selection device and which allow liquid from more than one reservoir at a time to pass through the selection device.

Embodiment 28

The cell culture and purification apparatus of embodiment 1, wherein said second cultureware module of said purification unit further comprises a device for diafiltering the purified product.

Embodiment 29

The cell culture and purification apparatus of embodiment 1, wherein said purification unit further comprises a device for monitoring the effluent from the selection device.

Embodiment 30

The cell culture and purification apparatus of embodiment 29, wherein the device for monitoring involves measuring the pH, absorbance at a particular wavelength, or conductivity of the effluent.

Embodiment 31

The cell culture and purification apparatus of embodiment 25, wherein the multiple liquid reservoirs each contain a wash buffer, an elution buffer, or a neutralization solution.

Embodiment 32

The cell culture and purification apparatus of embodiment 31, wherein the multiple liquid reservoir comprises two reservoirs, and wherein each of the two reservoirs contains a wash buffer.

Embodiment 33

The cell culture and purification apparatus of embodiment 25, wherein the pre-sterilized, disposable device for collecting effluent from the selection device includes at least two disposable reservoirs.

Embodiment 34

An automated method for the production of cells and cell products and purification thereof in a contaminant-free environment, comprising the steps of:

providing at least one first disposable cultureware module, said first module including a cell growth chamber;

providing a first reusable instrumentation base device incorporating hardware to support cell culture growth, said base device including a microprocessor control and a pump for circulating cell culture medium through the cell growth chamber;

providing at least one second disposable cultureware module, said second cultureware module including a selection device (such as a purification column);

providing a second reusable instrumentation base device incorporating hardware to receive fluid from the cell growth chamber;

removably attaching said at least one first cultureware module to said first instrumentation base device;

introducing cells into the cell growth chamber;

fluidly attaching a source of cell culture medium to said at least one first cultureware module;

programming operating parameters into the microprocessor control;

operating the pump to circulate the cell culture medium through the cell growth chamber to grow cells or cell products therein;

loading the culture medium containing the cell products onto the selection device to absorb a cell product onto the selection device;

eluting the absorbed cell product into an aqueous medium; and collecting the cell product in a pre-sterilized disposable collection vessel to form a purified cell product.

Embodiment 35

The method of embodiment 34, wherein the selection device is selected from the group consisting of affinity chromatography, immuno-affinity chromatography, ionic exchange chromatography, hydrophobic interaction chromatography, and size selection chromatography (SEC), or a combination of two or more of the foregoing.

Embodiment 36

The method of embodiment 34, wherein the selection device comprises a chromatography device comprising hydroxyapatite resin.

Embodiment 37

The method of embodiment 34, further comprising disposing of said at least one first cultureware module and said at least one second cultureware module.

Embodiment 38

The method of embodiment 34, wherein said at least one first cultureware module includes a gas exchange unit and further comprising the step of providing oxygen and adding or removing carbon dioxide to the cell culture medium to support cell metabolism.

Embodiment 39

The method of embodiment 34, wherein said at least one first cultureware module includes a pH sensor disposed therein and further comprising the step of controlling the pH of the cell culture medium.

Embodiment 40

The method of embodiment 38, further comprising the step of regulating the cell culture medium feed rate control of the medium.

Embodiment 41

The method of embodiment 40, wherein the step of regulating the cell culture medium feed rate control includes monitoring carbon dioxide levels in the cell growth chamber to calculate lactate concentration of the cell culture medium.

Embodiment 42

The method of embodiment 41, wherein the step of regulating includes calculating an initial bicarbonate level of the cell culture medium and utilizing the measured pH and carbon dioxide level of the cell culture medium to calculate the lactate concentration.

Embodiment 43

The method of embodiment 34, further comprising the step of heating the at least one first cultureware module to promote cell growth.

Embodiment 44

The method of embodiment 34, further comprising the step of pumping high molecular weight factor into the cell growth chamber.

Embodiment 45

The method of embodiment 44, wherein said first instrumentation base device includes a cool storage area, and said method further comprises the step of storing the high molecular weight factor and product harvest in the cool storage area.

Embodiment 46

The method of embodiment 34, wherein said cultureware module has an identifying code and further comprising the step of scanning the identifying code information into the microprocessor control.

Embodiment 47

The method of embodiment 34, further comprising the step of pre-sterilizing said at least one cultureware module.

Embodiment 48

The method of embodiment 34, wherein said at least one cultureware module includes a plurality of interface features integrated into the module and said step of attaching said at least one cultureware module to said instrumentation base device includes mating the module interface features with interface features on said instrumentation base device.

Embodiment 49

The method of embodiment 34, wherein said at least one cultureware module includes a plurality of sensors and further comprising the step of sensing fluid circulation rate, temperature and pH of the cell culture medium.

Embodiment 50

The method of embodiment 34, wherein said at least one cultureware module includes a fluid cycling unit disposed therein and further comprising the step of cycling and mixing fluid of the cell culture medium within the cell growth chamber.

Embodiment 51

The method of embodiment 50, wherein cycling is achieved by utilizing a sealed flexible reservoir for the EC reservoir and the step of cycling comprises cycling the cell culture medium in and out of the flexible reservoir.

Embodiment 52

The method of embodiment 51, wherein the step of cycling further comprises using a second flexible reservoir is used to apply indirect pressure to the EC reservoir to effect cycling of the cell culture medium.

Embodiment 53

The method of embodiment 34, further comprising the step of attaching another disposable cultureware module after the step of disposing of said at least one cultureware module.

Embodiment 54

The method of embodiment 34, further comprising the step of directing an operator through a sequenced run of the cell culture process with the microprocessor control.

Embodiment 55

The method of embodiment 34, further comprising the step of transferring the product into an acidic solution.

Embodiment 56

The method of embodiment 55, wherein the transfer is achieved by diafiltration.

Embodiment 57

The method of embodiment 55, wherein the product is held in the acidic solution.

Embodiment 58

The method of embodiment 34, further comprising the step of transferring the product (antibody) to a basic solution.

Embodiment 59

The method of embodiment 58, wherein transfer is achieved by diafiltration.

Embodiment 60

The method of embodiment 59, further comprising the step of transferring the product to a final buffer solution.

Embodiment 61

The method of embodiment 60, wherein the transfer is achieved by diafiltration.

Embodiment 62

The method of embodiment 34, further comprising the step of washing the selection device with at least one solution prior to loading the medium.

Embodiment 63

The method of embodiment 34, further comprising the step of washing the selection device with at least one solution prior to eluting the product.

Embodiment 64

The method of embodiment 63, wherein the at least one solution comprises the use of PBS, glycine, and/or citrate.

Embodiment 65

The method of embodiment 34, further comprising the step of warming and/or degassing the medium prior to loading the medium onto the selection device.

Embodiment 66

The method of embodiment 34, wherein the step of eluting the product comprises the use of a solution containing glycine or citrate.

Embodiment 67

The method of embodiment 66, wherein the solution comprises approximately 0.1 M glycine at a pH of about 2.4 or approximately 0.1 M citrate at a pH of about 3.0.

Embodiment 68

The method of embodiment 34, wherein the step of eluting the product comprises the use of a photometer.

Embodiment 69

The method of embodiment 55, wherein the step of transferring the product into an acidic solution comprises the use of a solution containing glycine.

Embodiment 70

The method of embodiment 69, wherein the solution comprises approximately 0.1 M glycine at a pH of about 2.4.

Embodiment 71

The method of embodiment 58, wherein the step of transferring the product to a basic solution comprises the use of a solution containing citrate.

Embodiment 72

The method of embodiment 69, wherein the basic solution comprises approximately 10 mM citrate at a pH of about 5.3.

Embodiment 73

The method of embodiment 60, wherein the step of transferring the product to a final buffer solution comprises the use of solution containing saline.

Embodiment 74

The method of embodiment 73, wherein the final buffer solution comprises approximately 0.2-0.9% saline.

Embodiment 75

The method of embodiment 60, further comprising the step of filtering the product contained in the final buffer solution prior to collecting the product in a pre-sterilized, disposable collection vessel.

Embodiment 76

The method of embodiment 34, wherein the selection device comprises a column packed with an affinity resin.

Embodiment 77

The method of embodiment 76, wherein the affinity resin is anti-IgM resin.

Embodiment 78

The method of embodiment 76, wherein the affinity resin is selected from the group consisting of a Protein A, Protein G, and anti-IgG resin.

Embodiment 79

The method of embodiment 34, wherein the product is an antibody.

Embodiment 80

The method of embodiment 79, wherein the antibody comprises IgM, IgG, IgD, IgE, or IgA.

Embodiment 81

The method of embodiment 79, wherein the antibody comprises IgM.

Embodiment 82

The method of embodiment 79, wherein the antibody targets an idiotype antigen expressed on B cell tumors.

Embodiment 83

An automated method for producing an immunogenic composition such as a vaccine, comprising:
purifying an antibody from an antibody-containing aqueous medium using the method according to any of embodiments 34-82; and
conjugating the purified antibody to an adjuvant.

Embodiment 84

The method of embodiment 83, wherein the adjuvant comprises keyhole limpet hemocyanin (KLH).

The present invention is further illustrated by the following examples which should not be construed as further limiting.

All patents, patent applications, provisional applications, and publications referred to or cited herein, supra or infra, are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

Example 1—Automated Purification Technique for Immunoglobulins

In a particular embodiment of the invention, the automated method involves purifying an antibody (e.g., IgM or IgG) using the steps outlined below and using the purification unit shown schematically in FIG. 32.

Supernatant Source:

Filtered supernatant containing the unpurified antibody (IgM, IgG, or other immunoglobulin isotype) is produced in an automated cell culture device (e.g., the AUTOVAXID™ cell culture module). Once the desired quantity of antibody has been produced (e.g., approximately 100 mg of antibody) the automated purification module is connected to the cell culture device. The filtered supernatant is transferred to the automated purification unit by a pump.

Column Set-Up:

For IgM, a pre-sterilized, disposable, glass 2.5×10 cm column is packed with anti-IgM chromatography resin and snapped into the automated unit which also includes a UV monitor and electronic data recorder. Using the automated purification unit as shown in FIG. 32, PBS is flowed through the column at a pump rate of 5 mL/min. This same pump rate is used throughout the process. The column is pre-eluted with 0.1 M glycine at pH 2.4. The column is then equilibrated with PBS.

For IgG, a pre-sterilized, disposable 1.5×10 cm column is packed with Protein A chromatography resin and snapped into the automated apparatus which also includes a UV monitor and chart recorder. Using the automated purification unit as shown in FIG. 32, the system is primed with PBS at a pump rate of 5 mL/min. The column is pre-eluted with 0.1 M citrate at a pH of 3.0. The column is then equilibrated with PBS.

Purification:

For IgM, the filtered supernatant is passed through a heater to warm it to ambient temperature prior to entering the column. Once all of the supernatant has entered the column, the column is washed with PBS to remove unbound impurities. The column is then further washed with PBS at a pH of 5. The purified IgM is eluted from the column using 0.1 M glycine at a pH of 2.4. The UV absorbing peak containing the purified IgM is collected and sent to a mixing chamber for further processing.

For IgG, the filtered supernatant is passed through a heater to warm it to ambient temperature prior to entering the column. Once all of the supernatant has entered the column, the column is washed with PBS to remove unbound impurities. The purified IgM is eluted from the column using 0.1 M citrate at a pH of 3.0. The UV absorbing peak containing the purified IgG is collected and sent to a mixing chamber for further processing.

Sanitization of Diafiltration Apparatus:

A membrane based ultrafiltration device is installed in the automated purification module. This cassette or device contains a membrane of 50 cm$^2$ area having a normal molecular weight limit or cutoff of 50,000 daltons. This device works on the tangential flow filtration principle whereby molecules over 50,000 daltons, such as the IgG and IgM, cannot pass through the membrane but small molecules, such as buffers can pass through. The tangential flow filtration cassette is used to exchange one buffer for another and is a more efficient substitute for dialysis. After installation, the tangential flow filter (TFF) cassette and system is sanitized using 0.1N Sodium Hydroxide at a crossflow or feed rate of 20-40 mL/min. This crossflow rate is maintained throughout the process. After sanitization is complete the 0.1N Sodium Hydroxide is flushed out of the system using 0.1M Glycine at a pH of 2.4. The antibody is then introduced into the system.

Low pH Treatment:

The remaining steps are the same for either IgM or IgG. The antibody is diafiltered against enough volume of 0.1M Glycine pH 2.4 to ensure that the previous buffer that the antibody was solubilized in has been replaced by the 0.1M Glycine pH 2.4. Enough volume is used so that the buffer exchange efficiency is theoretically greater than or equal to 99.5%. Once in 0.1M Glycine pH 2.4, the antibody is treated (held) for 30 minutes at these conditions in order to inactivate any susceptible virus that may be present.

Neutralization:

After the 30 minute treatment the antibody is diafiltered against 10 mM Citrate at a pH of 5.3. The antibody is diafiltered against sufficient 10 mM Citrate at a pH of 5.3 to neutralize the effects of the previous low pH treatment.

Final Buffer Exchange:

After neutralization, the antibody is diafiltered into 0.2-0.9% Saline (NaCl). Again, enough volume is used so that the buffer exchange efficiency is theoretically greater than or equal to 99.5%. Once in the final buffer the antibody is filtered through a 0.22 μm filter and removed from the automated purification unit. This filtered purified antibody can be stored in 0.2-0.9% Saline or further processed.

The foregoing particular embodiment is summarized below.

Purification Module
1) Prosep a Column Used for IgG Purification
4 mL Prosep-rA Column 1.5 cm diam 5 mL/min
Sanitization: 0.3% HCl pH 1.5
Pre-Equilibration: PBS pH 7.2
Pre-Elution: 0.1M Citrate pH 3.0
Equilibration: PBS pH 7.2
Load: Undiluted Culture Harvest
Post Load Wash: PBS pH 7.2
Elution: 0.1M Citrate pH 3.0
Discard after one use
2) 1D12-CL4B (Anti-IgM Antibody) Column Used for IgM Purification
9 mL 1D12-Sepharose 4B Column 2.5 cm diam 5 mL/min
Pre-Equilibrate: PBS pH 7.2
Pre-Elution: 0.1M Glycine pH 2.4
Equilibration: PBS pH 7.2
Load: Undiluted Culture Harvest
Post Load Wash 1: PBS pH 7.2
Wash 2: PBS pH 5
Elution: 0.1M Glycine pH 2.4
Discard after one use
3) Material coming from 1 and 2 enters diafiltration module of the cultureware. Diafiltration using Pellicon XL Biomax 50 screen channel A. This would also include the 30 minute low pH hold to inactivate susceptible virus.
Pellicon XL Biomax 50 membrane area=50 cm$^2$ 20-40 mL/min cross flowrate
Sanitize: 0.1N NaOH
Hold: 30 minutes at pH 2.4
Flush: 0.1M Glycine pH 2.4
Fill Mix Chamber with Glycine pH 2.4
Precondition: 0.1M Glycine pH 2.4
Fill Mix Chamber with Ab
Diafilter against: 0.1M Glycine pH 2.4
Hold:
Diafilter Antibody against 10 mM Citrate pH 5.3
Diafilter Antibody against 0.2% to 0.9% Saline
Remove Antibody from system through 0.22 μm Filter 10 mL/min
Discard Pellicon after one use Example 2—Verification of the IgM Purification Process for the Automated Downstream Processing Instrument The purpose of this experiment was to verify the IgM purification process using the purification unit of the invention. The experiment successfully verified the suitability of the human IgM purification platform and verified that the process can achieve satisfactory product quality and process performance by purifying three different IgM molecules from cell culture supernatant to final product.

Figure 35:
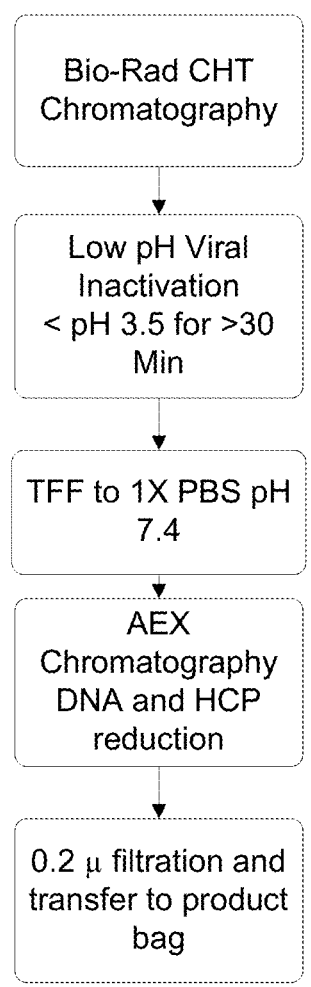
FIG. 35 is a flow diagram of an embodiment of the immunoglobulin purification process.

IgM was purified from cell culture batches (crude supernatant) using a combination of filtration and chromatography-based unit operations. Briefly, the cell free harvest is loaded onto a ceramic hydroxyapatite (CHT) chromatography column where IgM is bound to the resin via a metal affinity mode. The bound antibody was released from the resin using a step change in the phosphate concentration of the mobile phase. The CHT process step removes a significant amount of process-related impurities. Following this initial purification step, the protein containing solution was virally inactivated using low pH for greater than 35 minutes, followed by neutralization and buffer exchange using 50 KD cassettes (Millipore) operated in tangential filtration mode. The product was then loaded onto a flow through (non-binding) Anion Exchange (AEX) chromatography step using Bio-Rad's UNOspere Q to remove negatively charged impurities such as DNA, and Host Cell Protein (HCP). The product was then aseptically recovered though a sterilizing grade 0.2 micron final filter. The human IgM purification process is summarized in FIG. 35.

The results of this study demonstrate that the purification unit can rapidly execute the process steps in a highly automated fashion and deliver product yield of 25 to 52%, host cell protein clearance of 1.8-2.1 logs and expected product quality.

The purification unit is a self-contained device that incorporates single-use cultureware to purify monoclonal antibodies and other biological molecules. Development and evaluation of the prototype instrument confirmed the suitability for a generic human IgM purification platform and verified that the process will result in satisfactory product quality and process performance. The following describes the verification testing with three human IgMs purified using the purification platform.

Materials and Methods

Purification Unit.

Purification was performed using an automated purification unit manufactured by Biovest International, Inc. The instrument includes of two parts; a reusable chassis that contains pumps, valve actuators, a pressure sensor and a UV spectrophotometer; and a disposable set of "cultureware" that consists of all product contact surfaces such as tubing, valves, columns, filters, etc. The cultureware is intended to be used once and then discarded.

Cell Culture Supernatant.

Cell culture supernatant was collected from 3 separate hollow fiber cell culture runs and stored at −20° C. until purification. The material was thawed at 2-8° C. prior to further processing. The material was retained from previous work performed by Biovest and the batches were identified as P92-0349, P92-0375 and P92-0073.

Buffers and Solutions.

Buffers and solutions (USP grade) were prepared by combining acidic and basic components such that additional pH adjustment is reduced. All buffers and solutions were sterile filtered prior to use. Recipes for the buffers and solutions used in the process may be found below under "Buffer and Solution Preparation Recipes".

Chromatography.

Capture chromatography was performed using Ceramic Hydroxyapatite Type II chromatography resin (Bio-Rad). A 2.5 cm 8.5 cm column (CV=41.7 mL) was packed in a Sigma-Aldrich column and adaptor (Catalog Number C4669). The column was sanitized for 30 minutes in 0.1M NaOH and then pre-equilibrated in 3 CV of 125 mM Phosphate, 25 mM NaCl pH 7.0 and then equilibrated in 10 mM Phosphate, 25 mM NaCl, pH 7.0. After equilibration, the column was loaded with room temperature cell culture supernatant to a maximum capacity of 12 mg/ml. The cell culture supernatant was mixed 1:2 with 10 mM Phosphate, 25 mM NaCl, pH 7.0 during load via in-line dilution. After loading the column was washed in 5 CV of 10 mM Phosphate, 500 mM NaCl and then further washed with an additional 5 CV of 10 mM Phosphate, 25 mM NaCl, pH 7.0. The product was eluted with a step change in phosphate using 125 mM Phosphate, 25 mM NaCl, pH 7.0. The UV was monitored and the eluate was collected from 0.5 O.D. rising to 0.5 O.D. descending. All operations of this process step were performed at 5 mL/min (55 cm/hr). As product eluted from the column, it was continuously transferred to the tangential flow (TFF) loop for subsequent processing.

Low pH Tangential Flow.

Prior to product elution from the CHT column, the TFF loop was sanitized for 60 minutes in 0.1M NaOH, followed by equilibration with 80 L/M$^2$ of 20 mM citrate pH 3.5. After product was collected from the CHT column, a constant 50 mL volume was maintained in the mix chamber during TFF operations. The diluted pool was then diafiltered against approximately 3 diavolumes (DV) of 20 mM citrate, pH 3.5, to reduce the pH to 3.5+/−0.2. Once the Diafiltration was complete the product was held for at least 35 minutes to inactivate endogenous retroviral-like particles or adventitious viruses. All operations during this process step were performed under constant pressure with a maximum cross flow rate of 40 mL/min and a maximum inlet pressure of 20 PSIG.

TFF to Final Buffer.

At the end of the 35 minute viral inactivation hold, diafiltration resumed with phosphate buffered saline (PBS), pH 7.4. Diafiltration in PBS continued for 9 DV to neutralize the product and ensure complete diafiltration into the buffer required for subsequent processing and product storage. All operations during this process step were performed under constant pressure with a maximum cross flow rate of 40 mL/min and a maximum inlet pressure of 20 PSIG.

Anion Exchange and Product Recovery.

After TFF was complete, the product was recovered from the TFF loop and processed over a Bio-Rad UNOspere Q anion exchange cartridge. The AEX cartridge was sanitized (at the same time as the TFF loop) and equilibrated in PBS, pH 7.4. Following AEX cartridge equilibration, the final filter was placed in line and equilibrated. The product was processed across these two steps in series. These process steps were performed at a maximum constant pressure of 25 PSIG. The product was passed through a 0.2 micron filter and collected aseptically in a 250 mL Stedim flexboy bag. Following product collection, an additional 20 mL of PBS was introduced into the TFF loop and passed through the AEX cartridge and 0.2 micron filter to recover any product held up in the system. This flush was collected in the same bag with the product.

Analytical.

All analytical work in support of this study was performed by Biovest's analytical development group. Yield was determined by comparing total milligrams of IgM loaded with the total milligrams recovered. IgM concentration was determined by human IgM ELISA. Impurity clearance was quantified by total log reduction of HCP across the entire purification process. HCP concentrations are determined by HCP ELISA and product quality is illustrated by a Coomassie stained, reduced SDS-PAGE of the load material and final product.

Results and Discussion

Process Performance

The purification unit demonstrated a product recovery of 46.7-51.9%. Product volume ranged from 67.5-71.8 mL. The concentration of the final product was directly proportional to the amount of protein loaded and ranged from 0.238-1.09 mg/mL as determined by human IgM ELISA. Processing times ranged from 7.5-11.0 hours start to finish depending on the initial supernatant volume (Table 1).

TABLE 1

Purification Process Performance

| Batch ID | Load Sample # RD2010-005- | Load Vol. (mL) | Load IgM Concentration (mg/mL) | mg loaded | Prod. Sample # RD2010-005- | Product Vol. (mL) | Prod. IgM Concentration (mg/mL) | Total IgM Recovered (mg) | Yield % |
|---|---|---|---|---|---|---|---|---|---|
| P92-0349 | 010 | 353.5 | 0.238 | 84.1 | 007 | 67.5 | 0.582 | 39.3 | 46.7 |
| P92-0375 | 004 | 785.1 | 0.166 | 130.3 | 008 | 71.8 | 0.450 | 32.3 | 24.7 |
| P92-0073 | 005 | 272.2 | 1.09 | 296.5 | 009 | 70.3 | 2.01 | 141.3 | 51.9 |

Impurity Clearance

The purification process, as described above, demonstrated the ability to clear approximately XX Logs of HCP. All of the product pools had less than 29,800 ng/ml of HCP (Table 2). HCP clearance appears to correlate with load volume.

TABLE 2

HCP Clearance across Purification Process

| Batch ID | Load Sample Number RD2010-005- | Load HCP Concentration (ng/mL) | Product Sample Number RD2010-005- | Product HCP Concentration (ng/mL) | HCP Log Clearance |
|---|---|---|---|---|---|
| P92-0349 | 010 | 1670000 | 007 | 23000 | 1.8 |
| P92-0375 | 004 | 847000 | 008 | 29800 | 1.4 |
| P92-0073 | 005 | 829000 | 009 | 7310 | 2.1 |

Product Quality

Figure 36:
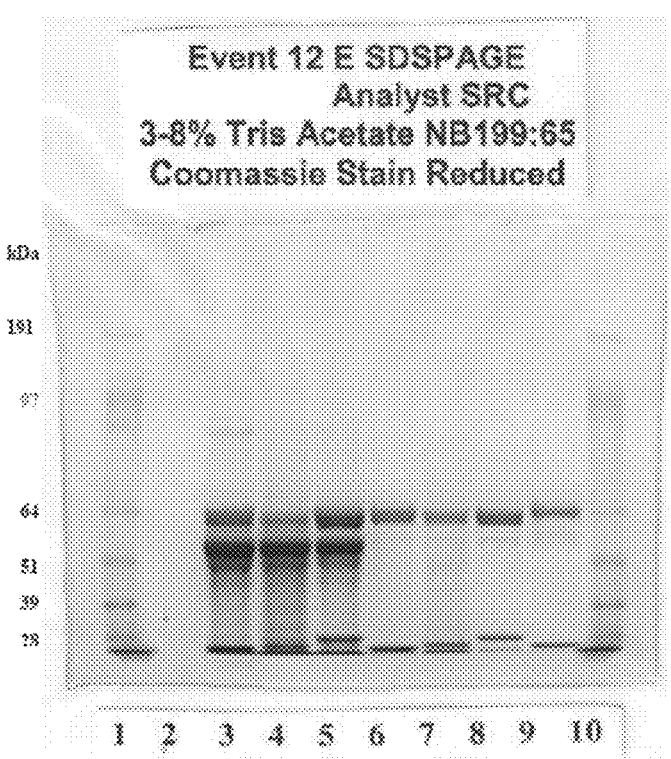
FIG. 36 is an SDS-PAGE gel of cell free harvest (load) and final product. Gel lane descriptions are listed in Table 3.

SDS-PAGE analysis shows that the purification process reduces the levels of high and low molecular weight impurities such as host cell proteins and aggregated and fragmented IgM. The product samples primarily display the characteristic heavy and light chain bands of reduced IgM. Batches P92-0375 and P92-0073 displays doublets in the light chain region, but this pattern is evident in the load material as well. This extra band may the J-chain found in pentameric IgM or it is possible that the IgM in these load materials degraded during storage, but this pattern does not appear to be an artifact of the purification process. See FIG. 36 and Table 3 for details.

TABLE 3

SDS-PAGE Gel Lane Descriptions

| Lane | Description |
|---|---|
| 1 | See Blue Plus 2 MWM |
| 2 | Blank |
| 3 | RD2010-002-087 P92-0349 Supernatant 5 μg load |
| 4 | RD2010-005-004 P92-0375 Supernatant 5 μg load |
| 5 | RD2010-005-005 P92-0073 Supernatant 5 μg load |
| 6 | RD2010-005-007 P92-0349 Product 5 μg load |
| 7 | RD2010-005-008 P92-0375 Product 5 μg load |
| 8 | RD2010-005-009 P92-0073 Product 5 μg load |
| 9 | IgM Standard (commercial) 5 μg load |
| 10 | See Blue Plus 2 MWM |

The platform human IgM purification process is suitable for implementation on the purification unit. Using an automated combination of integrated chromatography and filtration process steps, the instrument is capable of generating purified human IgM in less than eight hours. The implemented process demonstrates acceptable yield of greater than 25% and impurity clearance of greater than 1.5 Logs across a variety of IgM molecules and product loading.

Critical Process Filters and Chromatography Resins

TABLE 4

Process Filters and Chromatography Resins

| Resin/Filter Name | Purpose | Vendor Catalog Number |
|---|---|---|
| Bio-Rad Ceramic Hydroxyapatite Type II | Metal Affinity Capture Chromatography | 157-2000 |
| Millipore Biomax 50 - 50 cm² | Ultrafiltration/Diafiltration | PXB050A50 |
| Bio-Scale Mini UNOspere Q Cartridge | Anion Exchange Chromatography | 732-4102 |
| Sartolab P20 Plus | Sterile Product Filtration | 18058D |

Buffer and Solution Preparation Recipes

TABLE 5

0.1M NaOH - Chromatography Column and System Sanitization Solution

| Component | Molarity (mM) | g/L |
|---|---|---|
| Sodium Hydroxide | 100 | 4.0 |
| pH | ≥12 | |
| Conductivity (mS/cm at 24-26° C.) | 19-24 | |

TABLE 6

10 mM Phosphate 25 mM NaCl, pH 7.0 - CHT Equilibration and Wash 2 Buffer

| Component | Molarity (mM) | g/L |
|---|---|---|
| Sodium Phosphate (monobasic) | 4.7 | 0.635 |
| Sodium phosphate (dibasic-12 hydrate) | 5.3 | 1.90 |
| Sodium Chloride | 25 | 1.46 |
| pH | 6.8-7.2 | |
| Conductivity (mS/cm at 24-26° C.) | 3-7 | |

TABLE 7

125 mM Phosphate 25 mM NaCl, pH 7.0 - CHT Pre-equilibration and Elution Buffer

| Component | Molarity (mM) | g/L |
|---|---|---|
| Sodium Phosphate (monobasic) | 57.5 | 7.94 |
| Sodium phosphate (dibasic-12 hydrate) | 67.5 | 24.2 |
| Sodium Chloride | 25 | 1.46 |
| pH | 6.8-7.2 | |
| Conductivity (mS/cm at 24-26° C.) | 15-20 | |

TABLE 8

10 mM Phosphate 500 mM NaCl, pH 7.0 - CHT Wash 1 Buffer

| Component | Molarity (mM) | g/L |
|---|---|---|
| Sodium Phosphate (monobasic) | 3.0 | 5.82 |
| Sodium phosphate (dibasic-12 hydrate) | 7.0 | 0.04 |
| Sodium Chloride | 500 | 29.2 |
| pH | 6.8-7.2 | |
| Conductivity (mS/cm at 24-26° C.) | 43-53 | |

TABLE 9

| 10 mM Citrate, pH 3.5 - Low pH VI Hold Buffer | | |
| --- | --- | --- |
| Component | Molarity (mM) | g/L |
| Sodium Citrate Dihydrate | 15 | 1.50 |
| Anhydrous Citric Acid | 5.0 | 2.83 |
| pH | 3.4-3.6 | |
| Conductivity (mS/cm at 24-26° C.) | 1.0-3.0 | |

TABLE 10

| 1X Phosphate Buffered Saline, pH 7.4 - Final TFF Buffer | | |
| --- | --- | --- |
| Component | Molarity (mM) | g/L |
| Disodium Hydrogen Phosphate | 10.0 | 1.44 |
| Potassium Dihydrogen Phosphate | 2.0 | 0.24 |
| Sodium Chloride | 137 | 8.00 |
| Potassium Chloride | 2.7 | 0.20 |
| pH | 7.2-7.6 | |
| Conductivity (mS/cm at 24-26° C.) | 13-17 | |

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

We claim:

1. An automated cell culture and purification apparatus for the production of cells and cell derived products, comprising:
    (a) a cell culture unit comprising:
        a first reusable instrumentation base device incorporating hardware comprising a pump; and
        at least one first disposable cell cultureware module removably attachable to said first instrumentation base device, wherein said first cultureware module includes a cell growth chamber having ports for movement of cell culture medium through said cell growth chamber, wherein said pump circulates cell culture medium into and out of said cell growth chamber through said ports of said cell growth chamber; and
    (b) a purification unit connected to said cell culture unit by a fluid flow path there between, said purification unit comprising:
        a second reusable instrumentation base device incorporating hardware to receive fluid from said cell growth chamber of said cell culture unit through said fluid flow path, wherein said hardware comprises dual pumps for chromatography, comprising a first pump and a second pump, and a plurality of valves; and
        at least one second disposable cell cultureware module removably attachable to said second instrumentation base device of said purification unit, said at least one second cultureware module including a chromatography device, a diafiltration module that utilizes tangential flow filtration, an anion exchange filter, and a size-exclusion virus filter, wherein each of said first and second pumps pump fluid to said chromatography device, wherein said chromatography device, said diafiltration module, said size-exclusion virus filter, and said anion exchange filter are connected to said cell growth chamber of said cell culture unit by said fluid flow path, wherein said chromatography device separates a component from fluid received from said cell growth chamber, wherein said diafiltration module separates a component from fluid received from said chromatography device, wherein said anion exchange filter separates a component from fluid received from said diafiltration module or said chromatography device, and wherein said size-exclusion virus filter separates virus from fluid received from said chromatography device, said diafiltration module, or said anion exchange filter.

2. The cell culture and purification apparatus of claim 1, wherein said first instrumentation device of said cell culture unit includes a heating mechanism for heating said cell growth chamber to promote growth and production.

3. The cell culture and purification apparatus of claim 2, wherein said at least one first cultureware module of said cell culture unit includes an inlet and outlet port, said inlet and outlet ports being constructed and arranged to align with air ports of said instrument device of said cell culture unit such that said heating mechanism forces heated air into said at least one first cultureware module from said first instrument device of said cell culture unit.

4. The cell culture and purification apparatus of claim 1, wherein said chromatography device comprises an affinity resin.

5. The cell culture and purification apparatus of claim 4, wherein said affinity resin is selected from the group consisting of anti-IgM resin, Protein A, Protein G, and anti-IgG resin.

6. The cell culture and purification apparatus of claim 1, wherein said chromatography device comprises hydroxyapatite resin.

7. The cell culture and purification apparatus of claim 1, wherein said second disposable cultureware module further comprises: multiple, liquid reservoirs, a device for flowing liquid from said reservoirs and into said chromatography device, a device for diverting effluent from said chromatography device, and a pre-sterilized, disposable device for collecting effluent from said chromatography device.

8. The cell culture and purification apparatus of claim 7, wherein said device for flowing liquid into said chromatography device comprises a series of pre-sterilized, disposable valves and tubing which connect said reservoirs to said chromatography device and which allow liquid from only one reservoir at a time to pass through said chromatography device.

9. The cell culture and purification apparatus of claim 7, wherein said device for flowing liquid into said chromatography device comprises a series of pre-sterilized, disposable valves and tubing which connect said reservoirs to said chromatography device and which allow liquid from more than one reservoir at a time to pass through said chromatography device.

10. The cell culture and purification apparatus of claim 1, wherein said purification unit further comprises a device for monitoring effluent from said chromatography device.

11. The cell culture and purification apparatus of claim 10, wherein said device for monitoring effluent measures pH of effluent, measures absorbance of effluent at a particular wavelength, or measures conductivity of effluent.

12. The cell culture and purification apparatus of claim 7, wherein said pre-sterilized, disposable device for collecting effluent from said chromatography device includes at least two disposable reservoirs.

13. The cell culture and purification apparatus of claim 1, wherein said fluid flow path comprises tubing.

14. The cell culture and purification apparatus of claim 1, wherein said chromatography device comprises a chromatography column.

15. The cell culture and purification apparatus of claim 1, wherein said chromatography device comprises a chromatography membrane.

16. The cell culture and purification apparatus of claim 1, wherein said cell growth chamber of said at least one first disposable cell culture module of said cell culture unit comprises a hollow fiber bioreactor.

* * * * *

UNITED STATES PATENT AND TRADEMARK OFFICE
CERTIFICATE OF CORRECTION

PATENT NO. : 10,093,956 B2
APPLICATION NO. : 14/516868
DATED : October 9, 2018
INVENTOR(S) : Hirschel et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 117 days.

Signed and Sealed this
Twenty-third Day of April, 2019

Andrei Iancu
*Director of the United States Patent and Trademark Office*